(12) United States Patent
Kitamura et al.

(10) Patent No.: US 6,380,378 B1
(45) Date of Patent: Apr. 30, 2002

(54) NUCLEOTIDE COMPOUND, NUCLEOTIDE BLOCK OLIGONUCLEOTIDE, AND METHOD FOR PRODUCING THEM

(75) Inventors: Akinori Kitamura; Yoji Horie; Takayoshi Uchida; Tadao Yoshida, all of Tsukuba (JP)

(73) Assignee: Toagosei Company, Ltd., Tokyo (JP)

( * ) Notice: Subject to any disclaimer, the term of this patent is extended or adjusted under 35 U.S.C. 154(b) by 0 days.

(21) Appl. No.: 09/471,802

(22) Filed: Dec. 23, 1999

(30) Foreign Application Priority Data

| Dec. 24, 1998 | (JP) | 10-367384 |
| Dec. 28, 1998 | (JP) | 10-372949 |
| May 20, 1999 | (JP) | 11-139878 |
| May 20, 1999 | (JP) | 11-139882 |
| May 20, 1999 | (JP) | 11-139883 |
| Jun. 7, 1999 | (JP) | 11-159367 |

(51) Int. Cl.[7] .................. C07H 21/00; C07H 19/00

(52) U.S. Cl. .................. 536/25.3; 536/22.1; 536/25.31; 536/25.33; 536/25.34; 536/25.4; 536/26.7; 536/26.8

(58) Field of Search ............... 536/22.1, 25.33, 536/25.34, 25.4, 25.3, 25.31, 26.7, 26.8

(56) References Cited

U.S. PATENT DOCUMENTS

| 4,415,723 A | * 11/1983 | Caruthers et al. |
| 4,415,732 A | 11/1983 | Caruthers et al. |
| 4,725,677 A | 2/1988 | Koster et al. |

FOREIGN PATENT DOCUMENTS

| WO | 94/15946 | 7/1994 |
| WO | 97/42202 | 11/1997 |

OTHER PUBLICATIONS

Bonora, "Polyethylene Glycol: A High–Efficiency Liquid Phase (Help) for the Large–Scale Synthesis of the Oligonucleotides", Applied Biochemistry and Biotechnology, vol. 54, 1995, pp. 3–17.
Letsinger et al., "Some Developments in the Phosphitetriester Method for Synthesis of Oligonucleotides", Tetrahedron, vol., 40, 1964, No. 1, pp. 137–143.
Letsinger et al., "Use of Trichlorodimethylethyl as a Protecting Group and Tributylphosphine as a Deprotecting Agent in Oligonucleotide Synthesis", J. Am. Chem. Soc., vol. 104, pp. 6805–6806, 1982.

(List continued on next page.)

*Primary Examiner*—James O. Wilson
(74) *Attorney, Agent, or Firm*—Fitch, Even, Tabin & Flannery

(57) ABSTRACT

Novel nucleotide compounds represented by the formula (I)

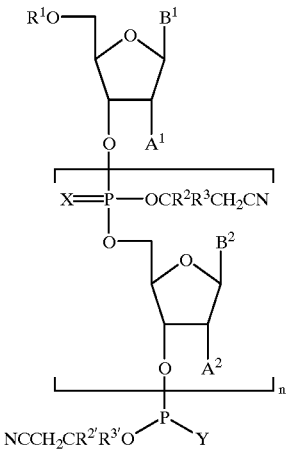

(I)

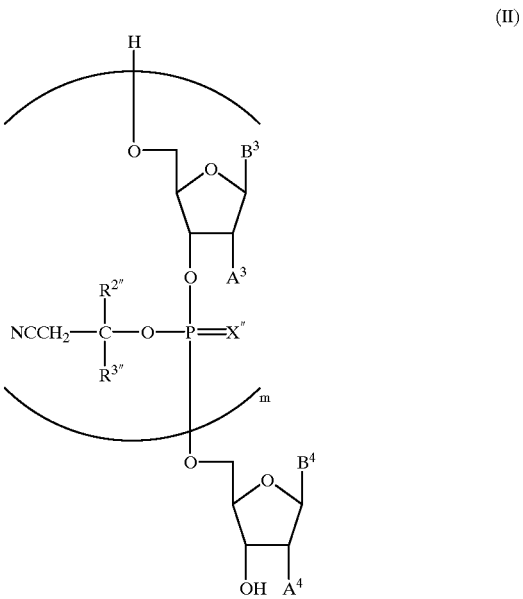

(II)

wherein $R^1$ represents a protective group or a PEG bearing organic group; $R^2$, $R^{2'}$, $R^{2''}$, $R^3$, $R^{3'}$ and $R^{3''}$ each represents a hydrogen atom or an alkyl, cycloalkyl, aryl or aralkyl group which may contain a hetero-atom; $B^1$, $B^2$, $B^3$ and $B^4$ each represents a base, if necessary, protected by a protective group common in nucleotide chemistry or by a PEG bearing organic group; X, X' and X" each represents an oxygen atom or a sulfur atom; Y represents an azolyl group, a mono- or di-alkylamino group or a saturated nitrogenous heterocyclic ring; $A^1$, $A^2$, $A^3$ and $A^4$ each represents a hydrogen atom, a hydroxyl group, an alkoxy group or a trialkylsilyloxy group; and m and n each represents 0 or an integer of 1 to 100. The nucleotide of the formula (I) can be used as it is in a reaction mixture for further reaction with 3'-O- and 5'-O-unprotected nucleoside or nucleotide of the formula (II) to yield a nucleotide block or oligonucleotide, and thus is useful as in situ DNA synthesis reagents.

21 Claims, No Drawings

OTHER PUBLICATIONS

Lee et al., "Bis–(N, N–Dialkylamino)—Alkoxyphosphines as a New Class of Phosphite Coupling Agent for the Synthesis of Oligonucleotides", The Chemical Society of Japan, pp. 1229–1232, 1984.

Moore et al., "Conceptual Basis of the Selective Activation of Bis(Dialkylamino) Methoxyphosphines by Weak Acids and Its Application Toward the Preparation of Deoxynucleoside Phosphoramidites in Situ", J. Org. Chem., vol. 50, pp. 2019–2025, 1985.

Krotz et al., "Phosphorothioate Oligonucleotides: Largely Reduced (N–1)–Mer and Phosphodiester Content Through the Use of Dimeric Phosphoramidite Synthons", Bioorganic & Medicinal Chemistry Letters, vol. 7, No. 1, pp. 73–78, 1997.

Sinha et al., "β–Cyanoethyl N, N–Dialkylamino/N–Morpholinomonochloro Phosphoamidites, New Phosphitylating Agents Facilitating Ease of Deprotection and Work–Up of Synthesized Oligonucleotides", Tetrahedron Letters, vol. 24, No. 52, pp. 5843–5846, 1983.

"Chemistry of Nucleic Adic and Molecular Biology–Elements of Chemistry 46", edited by Japan Chemical Association, and published by Gakkai Shuppan Center, 1985, pp. 217–225).

* cited by examiner

NUCLEOTIDE COMPOUND, NUCLEOTIDE BLOCK OLIGONUCLEOTIDE, AND METHOD FOR PRODUCING THEM

The present invention relates to a novel nucleotide, nucleotide block and oligonucleotide, and a method for producing the nucleotide block and oligonucleotide. These compounds and production method thereof according to the present invention are useful in synthetic organic chemistry, biochemistry and pharmaceutical industries, for example, as intermediates for the production of oligonucleotides and a method for producing the oligonucleotides.

Hitherto, a solid phase preparation method has been employed for preparation of oligodeoxyribonucleotides and oligoribonucleotides. According to this method, DNA chain or RNA chain is sequentially extended on a solid phase carrier insoluble in various organic solvents. More specifically, in general, using a starting material of a nucleoside whose 3'-hydroxyl group is fixed on an insoluble carrier such as a porous glass, an oligonucleotide chain is extended from 3' terminal to the direction of 5' terminal by one base at a time, and according to this method, oligonucleotides of desired sequences can be synthesized (Koester et al, JP-B-62-50479 corresponding to PCT/WO85/00816 and U.S. Pat. No. 4,725,677, and Caruthers et al, JP-B-63-28439 corresponding to U.S. Pat. No. 4,415,732). The above solid phase synthesis method has the merit that the excessively used reagents or solvents can be readily removed at the time of extension of the chain, and each elementary reaction is allowed to proceed by using excess reagents as required, whereby oligodeoxyribonucleotides and oligoribonucleotides having the desired sequence can be produced.

Generally, β-cyanophosphoramidite developed by Koester et al is used as a nucleotide reagent for extension of DNA chain or RNA chain, and a porous glass is used as a solid phase carrier. See H. Koester et al, "Tetrahedron Lett.", 52, 5843 (1983) and PCT/WO97/42202.

Furthermore, as the similar nucleotide reagents, there are also known phosphoramidite compounds of the following formula (I-1) where $R^{2'}$ and $R^{3'}$ are both hydrogen atom and Y is a dialkylamino group. See H. Koester et al, "Tetrahedron Lett.", 52, 5843 (1983) supra and PCT WO97/42202 supra.

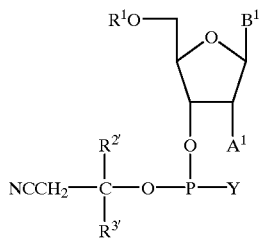

(I-1)

When the above phosphoramidite compounds are used as intermediates for DNA oligomers, generally, a 2-cyanoethoxydialkylaminophosphine derivative is reacted with a 5'-O- and base-protected nucleoside to make a DNA synthesis reagent.

According to this method, starting materials for chemical synthesis of DNA can be stably obtained, but in order to obtain the desired products in a high purity, by-products and impurities must be removed and this causes complexity in operation and increase of cost.

Therefore, in situ DNA synthesis reagents are needed, which do not require any steps of isolation and purification in preparation, and can be used as they are in a form of reacted solution for further reaction of synthesis of DNA oligomers.

Furthermore, the above conventional method has severe restrictions. One of them is that since accurate control of reaction on the solid phase is very difficult, particularly when the method is designed on a desired reaction scale, it is very difficult to set conditions therefor. Moreover, the porous glass is very expensive. Furthermore, since it is fundamental to use the reagents in excess amounts, this method is economically very disadvantageous when oligodeoxyribonucleotides are to be obtained in large amounts.

Specifically, it is technically not easy and requires much cost to design and practice the reaction in such a scale as exceeding 1 mmol utilizing a porous glass. These problems mean that if oligodeoxyribonucleotides were utilized for the pharmaceutical use, supply of them would be actually difficult.

In the production of oligodeoxyribonucleotides and oligoribonucleotides, there are demanded novel nucleoside compounds which can be utilized as starting materials for obtaining oligonucleotide in large amounts or as building blocks for extension of chains by use of easily available solid phase carriers, thereby facilitating separation and purification of intermediate products.

Furthermore, all of the steps in the above-mentioned conventional synthesis method are constructed of consecutive reactions and, hence, oligonucleotides having the desired sequences cannot be obtained unless all of the steps proceed with reaction yields of 100% or extremely close to 100%. Especially, the phosphorylation reaction step (condensation reaction) which is a step of extension of nucleotide chains gives a yield of 98.5–99.5 for each extension reation even in the present highest level, and this reaction yield determines the total yield of oligonucleotides having a desired sequence.

Recently, there is a report that a synthesis method in which a dimer nucleotide is used as a building block in building nucleotide chains thereby reducing the number of condensation is effective for improving the total yield (Krots et al, "Bioorg. Med. Chem. Lett.", 1997, 7, 73–78). Furthermore, there are many chemical synthesis methods for oligonucleotides using dimers or higher as building blocks (for example, "Chemistry of Nucleic Acid and Molecular Biology-Elements of Chemistry 46" edited by Japan Chemical Association, and published by Gakkai Shuppan Center, 1985, pp.209–240). However, in the case of these building blocks, a series of the steps of protection-deprotection and phosphorylation are very complex and furthermore the operations such as extraction and chromatography are necessary in each step for the removal of by-products and impurities. These cause not only complexity of operation, but also increase the cost for the synthesis of building blocks.

Hitherto, the compound (V') in the following formula (X) has been known as a nucleotide block which is an intermediate starting material for DNA oligomers, and as a method for synthesizing this compound, there is known a method which comprises the steps of reacting phosphoramidite compound (I') with a nucleoside derivative (IX), oxidizing the nucleotide bond of the resulting nucleotide, and removing the protective group for 3'-position hydroxyl group from the resulting nucleotide derivative as shown in the following formula (X) (Refer to Japanese Patent Kohyo No.08-507752 corresponding to PCT/WO94/15946).

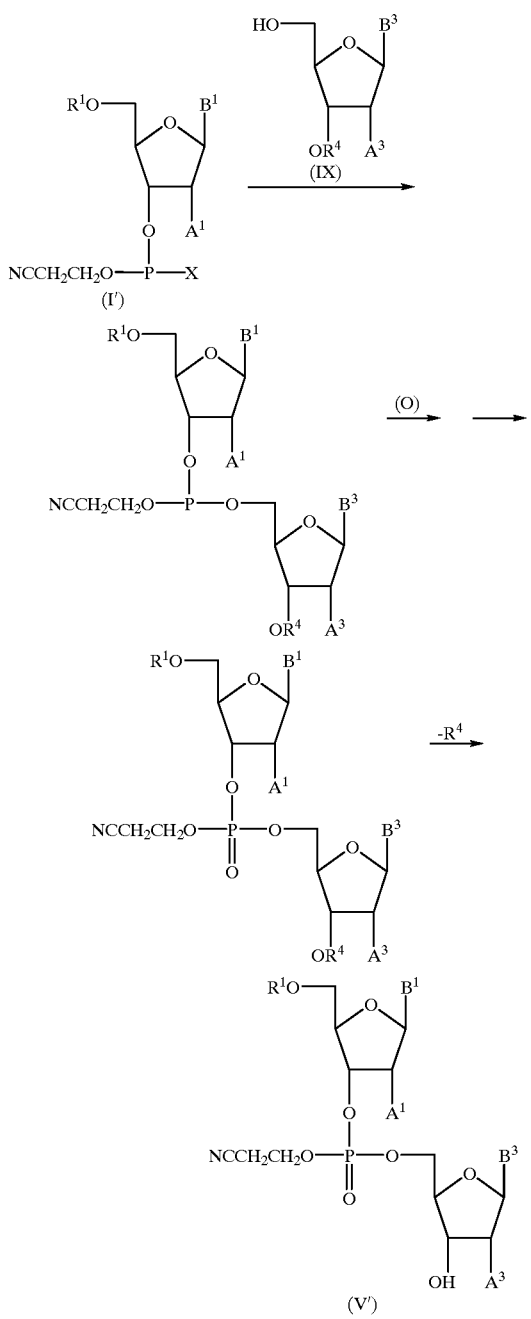

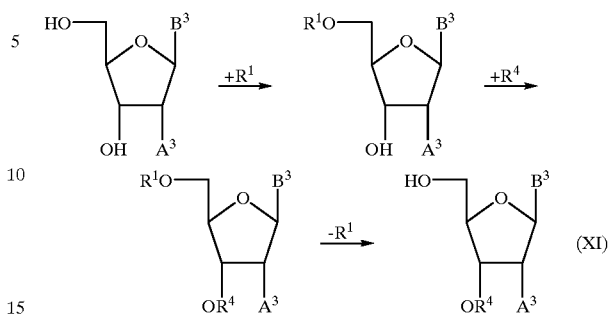

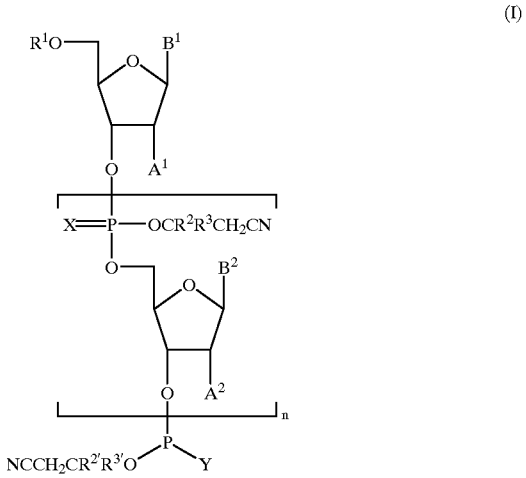

In the above formula (X), $B^1$ and $B^3$ are bases protected with protective groups common in nucleotide chemistry, $A^1$ and $A^3$ each represents a hydrogen atom, a hydroxyl group, an alkoxy group or a trialkylsilyloxy group, $R^1$ and $R^4$ each represents a protective group common in nucleotide chemistry, and X represents a dialkylamino group.

According to the above method, the nucleoside derivative represented by the formula (IX) which is a starting material must be produced in accordance with the reaction in the following formula (XI), and, in addition, the protective group $R^4$ must be removed from the nucleotide block derivative after dimerization reaction of nucleotide.

Therefore, in order to obtain a desired nucleotide block at high purity, the synthesis steps need many stages, and furthermore by-products or impurities must be removed thereby causing complexity of operation and increase of the cost.

In the above formula (XI), $B^3$, $R^1$, $R^4$ and $A^3$ are the same as defined in the formula (X).

Therefore, there are demanded a novel nucleotide compound and nucleotide block from which a nucleotide block useful for preparation of DNA oligomers can be simply produced without complex synthesis step and isolation and purification steps, as well as a method for producing an oligonucleotide using the same.

The object of the present invention is to provide nucleotide compounds and nucleotide blocks which meet the above-mentioned various demand, and a method for producing the same, and a method for producing an oligonucleotide using the nucleotide block.

As a result of intensive research conducted by the inventors in an attempt to solve the above problems, it has been found that when a nucleotide derivative represented by the following formula (I) is used, the above problems can be solved. Thus, the present invention has been accomplished.

That is, the present invention is a nucleotide compound represented by the following formula (I).

In the above formula (I), $R^1$ represents a protective group or an organic group represented by the formula —C(=O)-A'—(OCH$_2$CH$_2$)$_k$OCH$_3$ (in which k represents an integer of 3 or more, and A' is a divalent organic group; $R^2$, $R^{2'}$, $R^3$ and $R^{3'}$ each represents a hydrogen atom or an alkyl, cycloalkyl, aryl or aralkyl group which may contain a hetero-atom and $R^2$, $R^{2'}$, $R^3$ and $R^{3'}$ may be the same or different; $B^1$ and $B^2$ each represents a base, if necessary, protected by a protective group common in nucleotide chemistry or B' (B'=B$^{1'}$—C(=O)-A-(OCH$_2$CH$_2$)$_k$OCH$_3$ in which B$^{1'}$ represents one of the groups represented by the following formula (1), k represents an. integer of 3 or more, A is a divalent group and represents an arylene group or an alkylene group having a straight or branched chain which may contain a hetero-atom); X represents an oxygen atom or a sulfur atom; Y represents an azolyl group, a monoalkylamino group represented by HNR$^5$ (in which R$^5$ is an alkyl group or a cycloalkyl group), a dialkylamino group or a saturated nitrogenous heterocyclic ring; $A^1$ and $^2$ each represents a hydrogen atom, a hydroxyl group, an alkoxy group or a trialkylsilyloxy group; and n represents 0 or an integer of 1 to 100, with a proviso that the cases of the combinations ($R^2$ and $R^3$) and ($R^{2'}$ and $R^3$) being (hydrogen atom and hydrogen atom), (hydrogen atom and methyl group), (hydrogen atom and ethyl group), (methyl group and methyl group), (methyl group and ethyl group) or (ethyl group and ethyl group) are excluded.

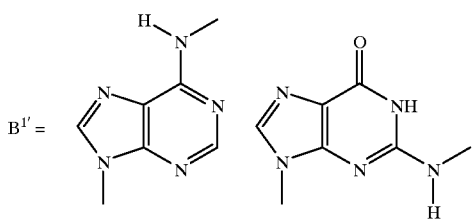

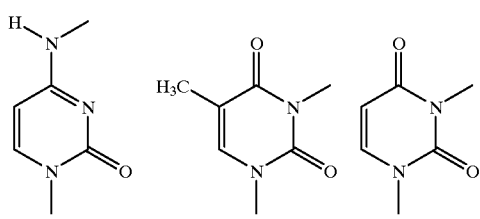

(1)

The inventors have further found that the above problems can be solved when the nucleotide compound represented by the above formula (I) is reacted with a 3'-O- and 5'-O-unprotected nucleoside derivative or nucleotide derivative represented by the following formula (II) to synthesize a novel nucleotide block or oligonucleotide having the structure represented by the following formula (IV) through a novel nucleotide having the structure represented by the following formula (III). Thus, the present invention has been accomplished.

That is, the present invention is a method for producing a nucleotide block or oligonucleotide represented by the following formula (IV), characterized in that a nucleotide compound represented by the following formula (I) is reacted with a 3'-O- and 5'-O-unprotected nucleoside derivative or nucleotide derivative represented by the following formula (II) and a trivalent phosphorus atom of the resulting nucleotide represented by the following formula (III) is oxidized or sulfurized to pentavalent phosphorus atom.

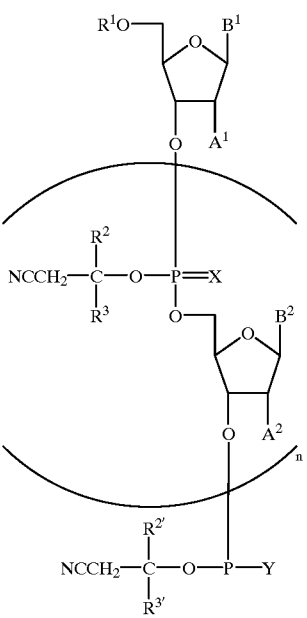

(I-4)

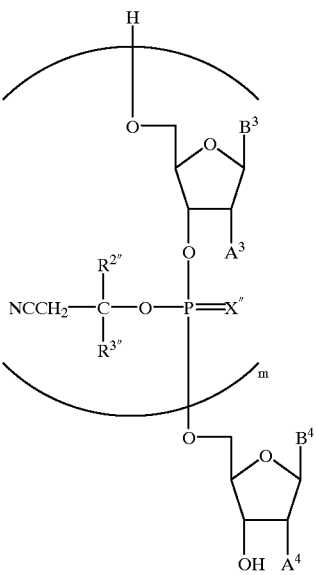

(II)

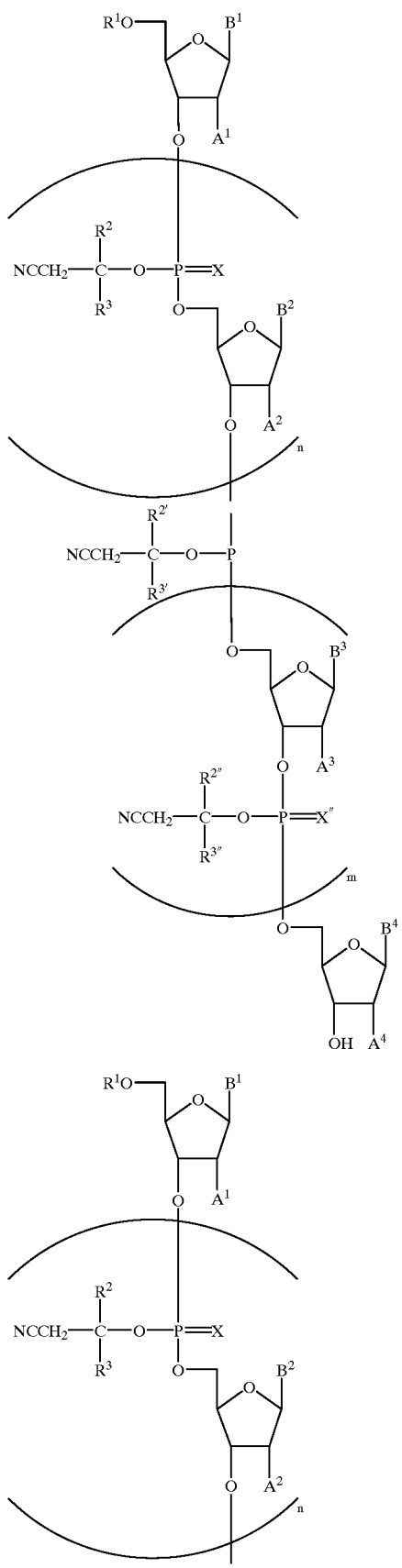

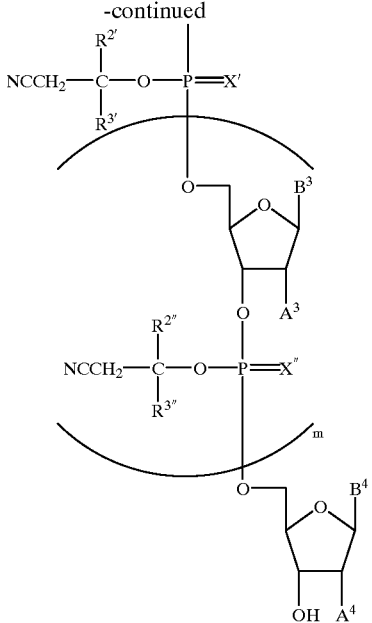

In the above formulas (I-4), (II), (III) and (IV), $R^1$ represents a protective group or an organic group represented by the formula $—C(=O)-A'-(OCH_2CH_2)_kOCH_3$ (in which k represents an integer of 3 or more, and A' is a divalent organic group); $R^2$, $R^{2'}$, $R^{2''}$, $R^3$, $R^{3''}$ and $R^{3'}$ each represents a hydrogen atom or an alkyl, cycloalkyl, aryl or aralkyl group which may contain a hetero-atom and $R^2$, $R^{2'}$, $R^{2''}$, $R^3$, $R^{3'}$ and $R^{3''}$ may be the same or different; $B^1$, $B^2$, $B^3$ and $B^4$ each represents a base, if necessary, protected by a protective group common in nucleotide chemistry or B' ($B'=B^{1'}—C(=O)-A-(OCH_2CH_2)_kOCH_3$ in which $B^{1'}$ represents one of the groups represented by the following formula (1), k represents an integer of 3 or more, A is a divalent group and represents an arylene group or an alkylene group having a straight or branched chain which may contain a hetero-atom); X, X' and X" each represents an oxygen atom or a sulfur atom; Y represents an azolyl group; $A^1$, $A^2_1$, $A^3$ and $A^4$ each represents a hydrogen atom, a hydroxyl group, an alkoxy group or a trialkylsilyloxy group; and m and n each represents 0 or an integer of 1 to 100, with a proviso that the cases of the combinations ($R^2$ and $R^3$), ($R^{2'}$ and $R^{3'}$) and ($R^{2''}$ and $R^{3''}$) being (hydrogen atom and hydrogen atom), (hydrogen atom and methyl group), (hydrogen atom and ethyl group), (methyl group and methyl group), (methyl group and ethyl group) or (ethyl group and ethyl group) are excluded.

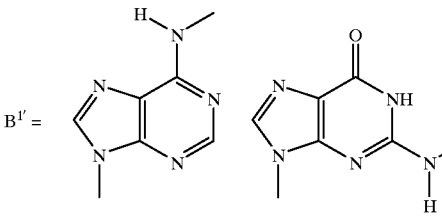

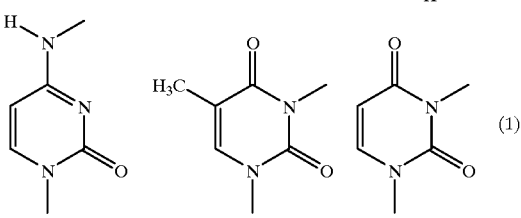

Furthermore, in the production method of the present invention, the compounds represented by the above formulas (III) and (IV) are novel nucleotide compounds.

(1) Among the nucleotide compounds represented by the above formula (I), the phosphorazolide compounds represented by the following formula (I-1) are suitable as in situ DNA synthesis reagents which can be used for further synthesis of DNA oligomers after synthesized without any isolation and purification step.

(I-1)

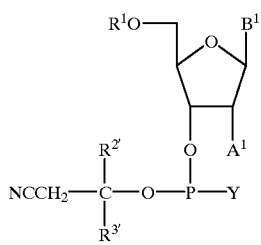

(wherein $B^1$ represents a base, if necessary, protected by a protective group common in nucleotide chemistry; $R^{2'}$ and $R^{3'}$ each represents a hydrogen atom or an alkyl, cycloalkyl, aryl or aralkyl group which may contain a hetero-atom; $R^1$ represents a protective group or an organic group defined in the above formula (I); $A^1$ represents a hydrogen atom, a hydroxyl group, an alkoxy group or a trialkylsilyloxy group; and Y represents an azolyl group; with a proviso that the cases of the combinations ($R^{2'}$ and $R^{3'}$) being (hydrogen atom and hydrogen atom), (hydrogen atom and methyl group), (hydrogen atom and ethyl group), (methyl group and methyl group), (methyl group and ethyl group) or (ethyl group and ethyl group) are excluded.)

In the compounds represented by the above formula (I-1), the bases represented by $B^1$ are known ones and as examples of the bases, mention may be made of purine derivatives such as derivatives of adenine, guanine and hypoxanthine and pyrimidine derivatives such as derivatives of cytosine, thymine and uracil. Specific examples are 1-thyminyl group, 1-(N-4-benzoylcytosinyl) group, 9-(N-6-benzoyladeninyl) group and 9-(N-2-isobutyrylguaninyl) group.

As $R^{2'}$ and $R^{3'}$ in the formula (I-1), mention may be made of hydrogen atom, methyl group, ethyl group, n-propyl group, isopropyl group, isobutyl group, sec-butyl group, tert-butyl group, n-pentyl group, 1-methylbutyl group, 1-ethylpropyl group, cyclohexyl group, n-nonyl group, 2-phenylethyl group, 2-(methylthio)ethyl group, phenyl group, 1,1-diethyl-3-butenyl group and 1,1-dimethyl-2-phenylethyl group, excluding the cases of the combinations ($R^{2'}$ and $R^{3'}$) being (hydrogen atom and hydrogen atom), (hydrogen atom and methyl group), (hydrogen atom and ethyl group), (methyl group and methyl group), (methyl group and ethyl group) or (ethyl group and ethyl group).

$R^1$ includes, for example, trityl group, 4-methoxytrityl group, and 4,4'-dimethoxytrityl group, and, besides, succinyl group having polyethylene glycol methyl ether residue at one end, and A' includes, for example, 1,4-phenylene group, methylene group and 1,1-dimethylethylene group, and Y includes, for example, imidazolyl group, 2-methylimidazolyl group, 4-methylimidazolyl group, and 2,4-dimethylimidazolyl group.

$A^1$ is hydrogen atom, hydroxyl group, alkoxy group and trialkylsilyloxy group, and alkoxy group includes, for example, methoxy group and ethoxy group, and trialkylsilyloxy group includes, for example, tert-butyldimethylsilyloxy group.

The phosphorazolide compound in the present invention can be easily produced by the reaction of a 5'-O- and base-protected nucleoside represented by the following formula (1-3) with an organooxybisazolylphosphine represented by the following formula (1-4) See the following formula (1-5).

(1-3)

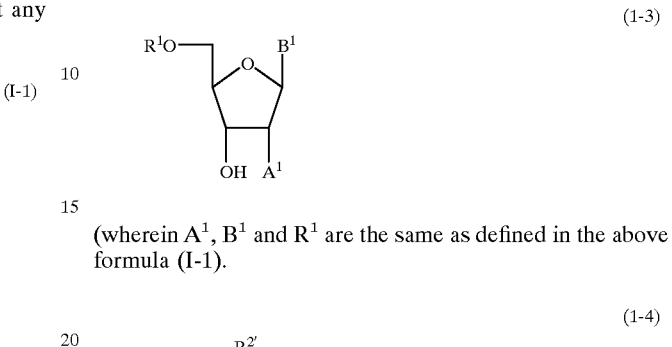

(wherein $A^1$, $B^1$ and $R^1$ are the same as defined in the above formula (I-1).

(1-4)

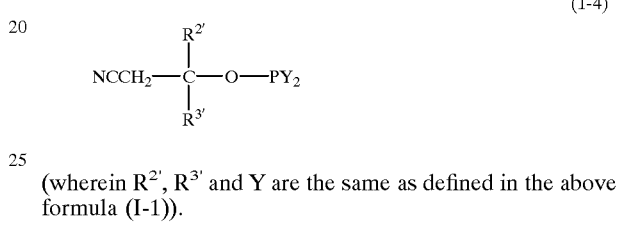

(wherein $R^{2'}$, $R^{3'}$ and Y are the same as defined in the above formula (I-1)).

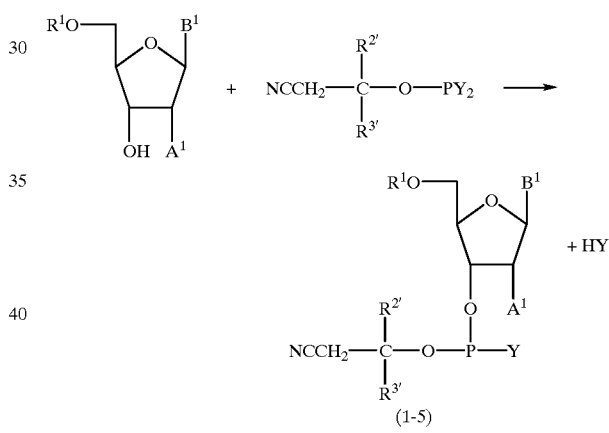

(1-5)

(wherein $A^1$, $B^1$, $R^{2'}$, $R^{3'}$, $R^1$ and Y are the same as defined in the above formula (I-1)).

The above reaction is carried out in the following manner. 5'-O- and base-protected nucleoside is vacuum dried or is dissolved in an organic solvent such as pyridine or 1,4-dioxane, followed subjecting to azeotropic dehydration, and then it is mixed with an organooxybisazolylphosphine in an amount of 0.9–1.2 equivalent to the 5'-O- and base-protected nucleoside in an organic solvent such as toluene, pyridine, tetrahydrofuran, chloroform or acetonitrile under the condition of −80° C. to room temperature. The reaction at lower temperature gives a higher yield of the phosphorazolide compound. Preferably, the organic solvent is one which has previously been dried with a drying agent and purified by distillation.

The completion of the reaction can be confirmed by measuring $^{31}$P-NMR spectrum of the reaction mixture. This reaction mixture can be used as it is as an in situ DNA synthesis reagent for synthesis of oligonucleotide.

On the other hand, the organooxybisazolylphosphine represented by the above formula (1-4) can be easily produced by the reaction of an organooxydichlorophosphine represented by the following formula (1-6) with an N-trimethylsilylazole compound represented by the following formula (1-7). See the following formula (1-8).

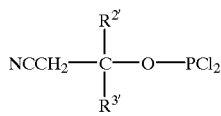
(1-6)

(wherein $R^{2'}$ and $R^{3'}$ are the same as defined in the above formula (I-1)).

(1-7)

(wherein Y is the same as defined in the above formula (I-1)).

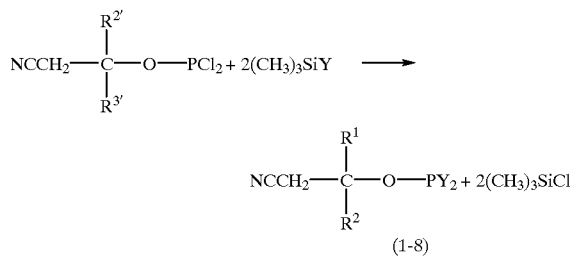
(1-8)

(wherein $R^{2'}$, $R^{3'}$ and Y are the same as defined in the above formula (I-1)).

The reaction represented by the above formula (1-8) is carried out by mixing an organooxydichlorophosphine with N-trimethylsilylazole compound in an amount of 2–3 equivalents to the organooxydichlorophosphine in toluene or a halogen organic solvent such as chloroform under the condition of room temperature. The reaction mixture is subjected to measurement of $^1$H-NMR spectrum to confirm completion of the reaction, and thereafter, the by-product chlorotrimethylsilane, the reaction solvent, the excess N-trimethylsilylazole compound and others are removed under reduced pressure to obtain the desired organooxybisazolylphosphine. Preferably the organic solvent is one which has previously been dried with a drying agent and purified by distillation.

The organooxydichlorophosphine represented by the above formula (1-6) can be easily produced by the reaction of the organooxytrimethylsilane represented by the following formula (1-9) with phosphorus trichloride. See the following formula (1-10) and Tsujiaki Hata et al, "Nucleic Acids Res.", 17, 8581 (1989)

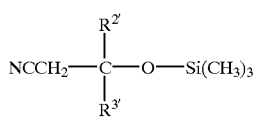
(1-9)

(wherein $R^{2'}$ and $R^{3'}$ are the same as defined in the above formula (I-1)).

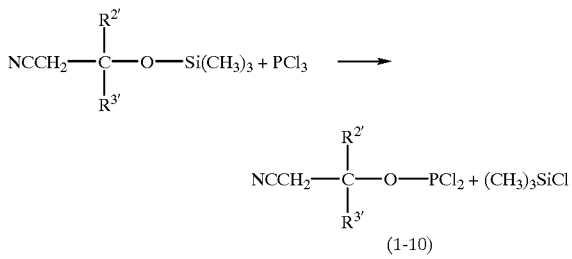
(1-10)

(wherein $R^{2'}$ and $R^{3'}$ are the same as defined in the above formula AE (I-1)).

The above reaction can be performed, for example, by mixing the above organooxytrimethylsilane with phosphorus trichloride in an amount of 2–5 equivalents to the organooxytrimethylsilane under the condition of 0° C., and leaving the product at room temperature for 1 hour to 10 days. The resulting product is subjected to conventional distillation under reduced pressure to obtain the above organooxydichlorophosphine.

The above organooxytrimethylsilane represented by the above formula (1-9) can be easily produced by the reaction of a 2-cyanoethanol derivative represented by the following formula (1-11) with 1,1,1,3,3,3-hexamethyldisilazane (the following formula (1-12)) or by the reaction of chlorotrimethylsilane with a reaction product of an aldehyde or ketone represented by the following formula (1-13) with a cyanomethyl alkali metal compound such as cyanomethyl lithium (the following formula (1-14)). The cyanomethyl alkali metal compound can be easily produced by alkali metallization of active hydrogen adjacent to cyano group of acetonitrile with n-butyl lithium or the like. See the following formula (1-15).

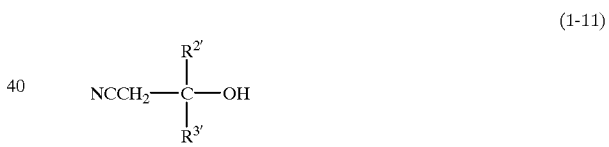
(1-11)

(wherein $R^{2'}$ and $R^{3'}$ are the same as defined in the above formula (I-1)) .

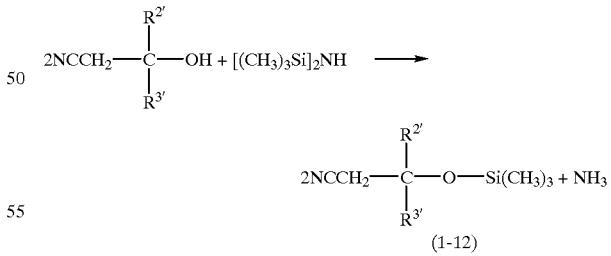
(1-12)

(wherein $R^{2'}$ and $R^{3'}$ are the same as defined in the above formula (I-1)).

The reaction represented by the above formula (1-12) can be performed by mixing a 2-cyanoethanol derivative with 1,1,1,3,3,3-hexamethyldisilazane in an amount of 1–2 equivalents to the 2-cyanoethanol derivative and imidazole in an amount of 0.005–0.1 equivalent to the 2-cyanoethanol derivative, followed by refluxing under heating with stirring for 1–5 hours. The resulting product is subjected to conven tional distillation under reduced pressure to obtain the desired above organooxytrimethylsilane.

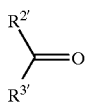

(1-13)

(wherein R$^{2'}$ and R$^{3'}$ are the same as defined in the above formula (I-1))

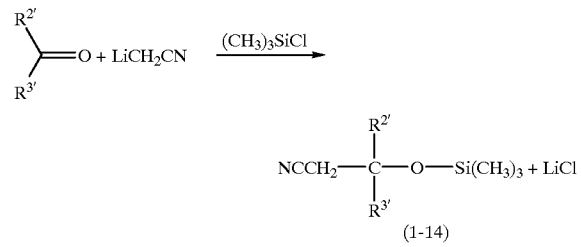

(wherein R$^{2'}$ and R$^{3'}$ are the same as defined in the above formula (I-1))

$$CH_3CN+CH_3CH_2CH_2CH_2Li \rightarrow LiCH_2CN+CH_3CH_2CH_2CH_3 \quad (1\text{-}15)$$

The reactions of the above formulas (1-14) and (1-15) are carried out in the following manner. First, to a solution of n-butyl lithium in n-hexane/tetrahydrofuran (ratio being 1/2) is added acetonitrile in an amount of 1.0–1.2 equivalents at the condition of −80° C. to −60° C., followed by stirring for 0.5–2 hours to carry out the reaction to obtain a solution of cyanomethyl lithium in n-hexane/tetrahydrofuran. Thereto is added the above aldehyde or ketone in an amount of 1.0–1.2 equivalents at the condition of −80° C. to −60° C., and the reaction temperature is returned to room temperature over a period of 0.5–1 hour, followed by stirring with addition of 1.2–1.5 equivalents of chlorotrimethylsilane. Preferably the organic solvent is one which has previously been dried with a drying agent and purified by distillation. Furthermore, the resulting product is subjected to conventional distillation under reduced pressure to obtain the desired organooxytrimethylsilane.

The N-trimethylsilylazole compound represented by the above formula (1-7) can be easily produced by the reaction of an azole represented by the following formula (1-16) with 1,1,1,3,3,3-hexamethyldisilazane. See the following formula (1-17).

HY (1-16)

(wherein Y is the same as defined in the above formula (I-1)).

$$2HY+[(CH_3)_3Si]_2NH \rightarrow 2(CH_3)_3SiY+NH_3 \quad (1\text{-}17)$$

(wherein Y is the same as defined in the above formula (I-1)).

The above reaction can be performed by mixing an azole represented by the formula (1-16) with 1,1,1,3,3,3-hexamethyldisilazane in an amount of 1–2 equivalents to the azole, followed by refluxing under heating with stirring for 3–24 hours. The resulting product is subjected to conventional distillation under reduced pressure to obtain the N-trimethylsilylazole compound.

The phosphorazolide compound represented by the formula (I-1) is useful as an intermediate starting material in chemical synthesis of oligonucleotide, and, for example, DNA oligomers can be obtained in a high yield by using a reaction mixture of 3'-O-4-methylimidazolylphosphine derivative obtained by reacting 2-cyano-1-(1,1-diethyl-3-butenyl)ethoxybis(4-methylimidazolyl)phosphine with 5'-O-(4,4'-dimethoxytrityl) thymidine, for solid phase synthesis on a DNA automatic synthesizer in situ.

Yield of this reaction has a correlation with sum of van der Waals volumes of R$^{2'}$ and R$^{3'}$ of the above formula (I-1), and for the reason of high reaction yields, compounds of 49(angstrom)$^3$ or larger in the sum of van der Waals volumes of R$^{2'}$ and R$^{3'}$ of the above formula (I-1) calculated under the following conditions are preferred. Examples of such compounds are those of R$^{2'}$ being hydrogen atom and R$^{3'}$ being n-propyl group.

Method for Calculation of the Van der Waals Volumes

In organooxybis(4-methylimidazolyl)phosphine represented by the following formula (2), first, three-dimensional molecular structure is determined by SPARTAN™ Version 4.1.1 (Wavefunction, Inc.) and steric energy is optimized using MM force field, and, thereafter, steric structure is established by semiempirical molecular orbital method (AM1) . Then, the van der Waals volumes of R$^{2'}$ and R$^{3'}$ are obtained by the molecular volume calculation program of TSAR™3.0 (Oxford Molecular Group) on the basis of the steric structure obtained by the AM1.

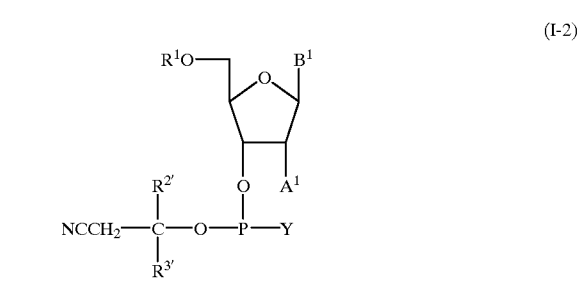

(2)

(wherein R$^{2'}$ and R$^{3'}$ are the same as defined in the above formula (I-1)).

(2) Like the compounds represented by the above formula (I-1), among the nucleotide compounds represented by the above formula (I), the monoalkylamino and dialkylamino type phosphoramidite compounds represented by the following formula (I-2) are suitable as in situ DNA synthesis reagents which can be used as they are in the reacted state for further synthesis of DNA oligomers without any isolation and purification step.

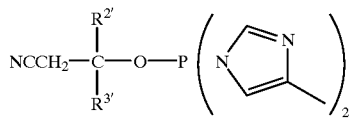

(I-2)

(wherein B$^1$ represents a base, if necessary, protected by a protective group common in nucleotide chemistry; R$^{2'}$ and R$^{3'}$ each represents a hydrogen atom or an alkyl, cycloalkyl, aryl or aralkyl group which may contain a hetero-atom; R$^1$ represents a protective group or an organic group defined in the above formula (I); A$^1$ represents a hydrogen atom, a hydroxyl group, an alkoxy group or a trialkylsilyloxy group; and Y represents a monoalkylamino group represented by HNR$^5$ (R$^5$ represents an alkyl group or a cycloalkyl group) or dialkylamino group; with a proviso that the cases of the combinations (R$^{2'}$ and R$^{3'}$) being (hydrogen atom and hydrogen atom), (hydrogen atom and methyl group), (hydrogen atom and ethyl group), (methyl group and methyl group), (methyl group and ethyl group) or (ethyl group and ethyl group) are excluded.)

In the compounds represented by the formula (I-2), as examples of $A^{1'}$, $B^{1'}$, $R^{2'}$, $R^{3'}$ and $R^{1'}$, mention may be made of those of the formula (I-1), and as examples of Y, mention may be made of isopropylamino group, n-butylamino group, isobutylamino group, tert-butylamino group, neopentylamino group, cyclohexylamino group, dimethylamino group and diisopropylamino group.

The monoalkylamino type and dialkylamino type phosphoramidite compounds as represented by the above formula (I-2) can be easily produced by the reaction of nucleotide derivatives represented by the following formula (I-1') with monoalkylamines or dialkylamine represented by the following formula (2-4). See the following formula (2-5).

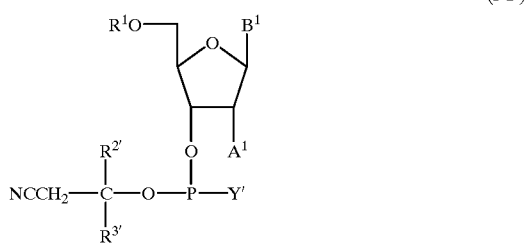

(wherein $A^1$, $B^1$, $R^{2'}$, $R^{3'}$ and $R^{1'}$ are the same as defined in the above formula (I-2), and Y' represents an azolyl group such as imidazolyl group, 2-methylimidazolyl group or 4-methylimidazolyl group).

(wherein Y is the same as defined in the above formula (I-2)).

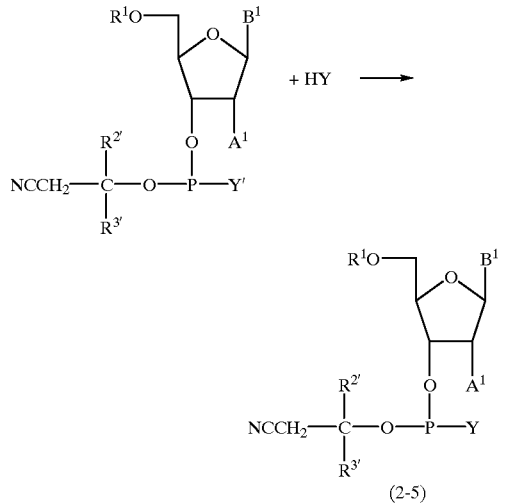

(wherein $A^1$, $B^1$, $R^{2'}$, $R^{3'}$, $R^{1'}$ and Y are the same as defined in the above formula (I-2), and Y' is the same as defined in the above formula (I-1')).

The nucleotide derivatives represented by the above formula (I-1') can be produced by the same method as for the compounds represented by the above formula (I-1). See the above formula (1-5).

The reaction represented by the above formula (2-5) is performed by adding to a reaction mixture resulting from the above mentioned preparation of the compound (I-1') a monoalkylamine or dialkylamine in an amount of 0.9–1.2 equivalent to the compound (I-1'). The resulting monoalkylamino type and dialkylamine type phosphoramidite compounds in the form of a reaction mixture can be used as it is without isolation and purification as an in situ DNA synthesis reagent for synthesis of oligonucleotide.

The monoalkylamino type and dialkylamino type phosphoramidite compound represented by the formula (I-2) is useful as an intermediate starting material in chemical synthesis of oligonucleotide, and, for example, a reaction of 2-cyano-1-tert-butylethoxybis(4-methylimidazolyl) phosphine with 5'-O-(4,4'-dimethoxytrityl)thymidine provides 3'-O-4-methylimidazolylphosphine derivative of the nucleoside in a high yield. When isopropylamine is added to the above obtained reaction mixture, 3'-O-isopropylamino type phosphoramidite derivative of the nucleoside can be quantitatively obtained. Furthermore, when the reaction mixture is used as it is in situ for solid phase synthesis on a DNA automatic synthesizer using tetrazole as a catalyst, DNA oligomers can be obtained in a high yield.

Among the monoalkylamino type and dialkylamino type phosphoramidite compounds of the formula (I-2), from the point of the yield of DNA oligomers, preferred are those of 49(angstrom)$^3$ or larger in the sum of van der Waals volumes of the substituents $R^{2'}$ and $R^{3'}$ of the formula (I-2). Examples are monoalkylamino type phosphoramidite compounds of $R^{2'}$ being hydrogen atom and $R^{3'}$ being n-propyl group. The van der Waals volumes are calculated by the calculation method mentioned above concerning the compound of the formula (I-1).

(3) Among the nucleotide compounds represented by the above formula (I), nucleotide compounds as represented by the following formula (I-3) in which polyethylene glycol (PEG) is introduced into the protective group of nucleic acid base can be separated and purified utilizing the properties of polyethylene glycol during the production of DNA synthesis reagents and are advantageous in that DNA oligomer products obtained therefrom are easy to handle as compared with those produced by conventional methods.

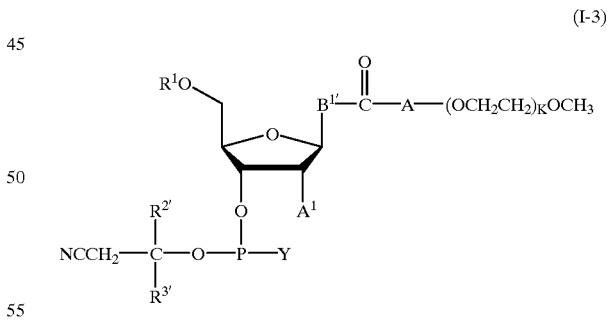

(wherein $B^{1'}$ represents a nucleic acid base commonly used in nucleotide chemistry; $R^{2'}$ and $R^{3'}$ each represents a hydrogen atom or an alkyl, cycloalkyl, aryl or aralkyl group which may contain a hetero-atom and $R^{2'}$ and $R^{3'}$ may be the same or different; $R^1$ represents a protective group or an organic group defined in the above formula (I); $A^1$ represents a hydrogen atom, a hydroxyl group, an alkoxy group or a trialkylsilyloxy group; and Y represents a monoalkylamino group, a dialkylamino group, an azolyl group or a saturated nitrogenous heterocyclic ring; k represents an integer of 3 or more; and A is a divalent group and represents an arylene group or an alkylene group having straight or branched chain which may contain a hetero-atom).

As can be seen from the above formula (I-3), the nucleotide compounds are compounds containing a polyethylene glycol chain as the protective group for amino group or imino group of nucleic acid base.

As $B^{1'}$ in the above formula (I-3), mention may be made of derivatives of adenine, guanine, cytosine, thymine and uracil represented by the following formula (1).

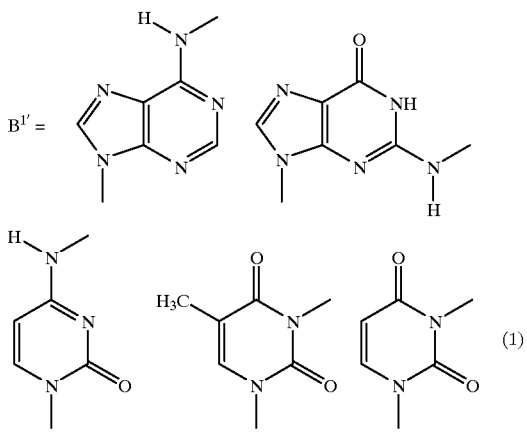

Examples of $R^1$, $R^{2'}$ and $R^{3'}$ and $A^1$ in the above formula (I-3) are the same as those in the above formula (I-1), examples of Y are the same as those in the above formulas (I-1) and (I-2), and examples of A and A' are 1,4-phenylene group, methylene group and dimethylethylene group.

Furthermore, the nucleoside compounds represented by the below-mentioned formula (I-3') which are precursors of the above formula (I-3) or synthesis intermediates are also novel compounds.

The nucleotide compounds represented by the formula (I-3) are obtained by reacting nucleosides represented by the following formula (3-3) which are those of $R^1$ being a protective group and $R^4$ being hydrogen atom in the below-mentioned formula (I-3') with a suitable phosphorylating agent.

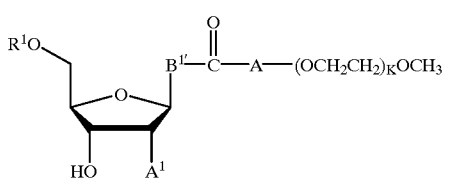

(3-3)

(wherein $B^{1'}$, $R^1$, $A^1$, A and k are the same as defined in the above formula (I-3)).

For the reaction with the phosphorylating agent, the reaction formula (1-5) shown before can be used, and, furthermore, in the case of the compounds where Y is a monoalkyl group or a dialkyl group, the reaction formula (2-5) can be used.

The nucleotide compound of the formula (I-3) obtained by the above reaction may be used for the subsequent reaction as it is without separation and purification. For example, under the condition of −80° C. to room temperature, the reaction mixture is mixed and reacted with a nucleoside compound at least only the base of which is suitably protected and which is subjected to vacuum drying or azeotropic dehydration and is in the form of a solution in an organic solvent such as toluene, pyridine, tetrahydrofuran, chloroform or acetonitrile, whereby dimerization reaction is performed. In this case, the 3' hydroxyl group of the nucleoside used in the above reaction is not necessarily protected.

The nucleotide compound of the formula (I-3) is soluble in acetonitrile, tetrahydrofuran, pyridine and organic chlorine solvents, and can be reacted with the 3'-O- and 5'-O-unprotected second nucleoside in an above mentioned solvent having good affinity with polyethylene glycol, whereby a dimer can be obtained. On the other hand, when to the solution containing the dimer component is added a non-solvent for polyethylene glycol, such as diethyl ether or diisopropyl ether in an amount of 5–20 times the volume of the solution, the dimer component is precipitated and can be easily recovered. Therefore, most of the separation-purification operations which have been needed for obtaining a dimer component from a conventional protected nucleotide with no polyethylene glycol moiety are eliminated. Besides, the present separation-purification method is sufficient for the subsequent building of nucleotide chains as well as for obtaining nucleotide dimer on a large scale. Accordingly, the present invention makes it possible to provide a very simple method for synthesis of building blocks of nucleotide dimers or oligomers and oligonucleotides.

(4) Moreover, the compounds of the formula (3-3) which are precursors for the compounds of the formula (I-3) can be easily synthesized through the compounds represented by the following formula (I-3').

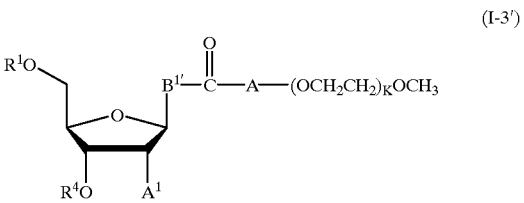

(I-3')

(wherein $R^1$ and $R^4$ each represents a hydrogen atom or a protective group commonly used in nucleotide chemistry; $A^1$ represents a hydrogen atom, a hydroxyl group, an alkoxy group or a trialkylsilyloxy group; A is a divalent group and represents an arylene group or an alkylene group having a straight or branched chain which may contain a hetero-atom; $B^{1'}$ represents one of the groups represented by the following formula (1); and k represents an integer of 3 or more).

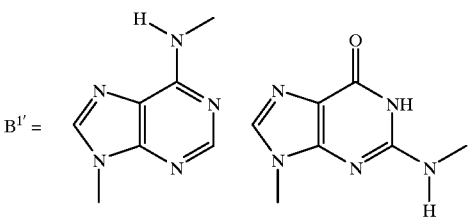

-continued

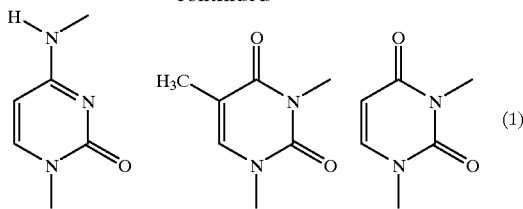

(1)

As can be seen from the above formula (I-3'), the nucleoside compound is a compound characterized by containing a polyethylene glycol chain at the protective group for amino group or imino group of nucleic acid base.

As $B^{1'}$ in the above formula (I-3'), mention may be made of derivatives of adenine, guanine, cytosine, thymine and uracil represented by the above formula (1). The protective groups commonly used in nucleotide chemistry for $R^1$ and $R^4$ include, for example, 4,4'-dimethoxytrityl group, trimethylsilyl group and t-butyldimethylsilyl group, and A includes, for example, 1,4-phenylene group, methylene group and dimethylethylene group.

The nucleoside compound in the above formula (I-3') can be produced, for example, from a nucleoside represented by the following formula (4-3) and a carboxylic acid derivative of polyethylene glycol represented by the following formula (4-4-4).

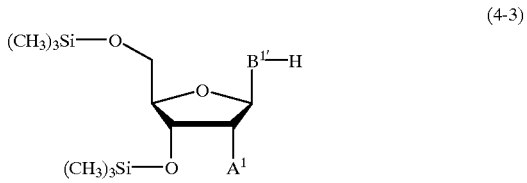

(4-3)

(wherein $B^{1'}$ and $A^1$ are the same as defined in the above formula (I-3')).

$$CH_3O(CH_2CH_2O)_KH \quad (4\text{-}4\text{-}1)$$

$$\rightarrow CH_3O(CH_2CH_2O)_KSO_2C_6H_4CH_3 \quad (4\text{-}4\text{-}2)$$

$$\rightarrow CH_3O(CH_2CH_2O)_K\rightarrow A\rightarrow COOH \quad (4\text{-}4\text{-}3)$$

$$\rightarrow CH_3O(CH_2CH_2O)_K\rightarrow A\rightarrow COZ \quad (4\text{-}4\text{-}4)$$

(wherein Z represents a halogen atom, an acyloxy group or an azolyl group, and A and k are the same as defined in the above formula (I-3')).

Furthermore, the nucleoside represented by the above formula (4-3) in which the hydroxyl groups are protected with trimethylsilyl groups can be produced by the following method. That is, nucleoside subjected to azeotropy with pyridine is suspended in pyridine in an inert gas atmosphere, followed by reacting with chlorotrimethylsilane in an amount of 3–5 equivalents under the condition of 0° C. to room temperature for 15–30 minutes. The reaction mixture can be used for the subsequent reaction without purification. See G. S. Ti et al, "J. Amer. Chem. Soc.", 104, 1316 (1982).

Moreover, the carboxylic acid derivative of polyethylene glycol which is represented by the above formula (4-4-4) can be produced by the following method. First, commercially available polyethylene glycol monomethyl ether (4-4-1) is reacted with tosyl chloride in the presence of sodium hydroxide to obtain a tosylated product (4-4-2) of polyethylene glycol monomethyl ether.

Then, in the presence of a base such as potassium carbonate, potassium-tert-butoxide and sodium hydride, the above tosylated product and an ester having an alcohol or a phenolic hydroxyl group such as methyl 4-hydroxybenzoate and methyl glucolate are refluxed under heating in acetonitrile or tetrahydrofuran to convert the tosylated product to an etherified product. The etherified product is subjected to alkali hydrolysis to obtain polyethylene glycol monomethyl ether having a carboxyl group at the end (4-4-3).

The resulting polyethylene glycol derivative is subjected to heat treatment with thionyl chloride to obtain an acid chloride, or is reacted with pivaloyl chloride in the presence of a tertiary amine to obtain a mixed acid anhydride, or is reacted with N,N'-carbodiimidazole to obtain an azole derivative (4-4-4).

The carboxylic acid derivative of polyethylene glycol which is represented by the above formula (4-4-4) is reacted with nucleoside having protected hydroxyl groups in an inert gas atmosphere at 0–40° C. for about 2–24 hours, whereby the polyethylene glycol derivative can be introduced as a protective group for amino group or imino group of the nuclei acid base. When deprotection of the hydroxyl groups is effected, there is obtained 3'-O- and 5'-O-unprotected nucleoside compound containing polyethylene glycol as a protective group for amino group or imino group of the nucleic acid base. When polyethylene glycol is introduced as a protective group for imino group, the presence of a tertiary amine such as diisopropylethylamine in this reaction results in rapid proceeding of the reaction. When 5'-hydroxyl group of the thus obtained 3'-O- and 5'-O-unprotected nucleoside is selectively protected, the compound of the above formula (3-3) is easily obtained.

The production of the nucleoside compound obtained above can be confirmed by thin layer chromatography and the like. Its structure can be identified by measuring $^1$H-nuclear magnetic resonance (NMR) spectrum.

The nucleoside compound represented by the formula (I-3') is a novel compound, and this compound is soluble in acetonitrile, tetrahydrofuran, pyridine, and organic chlorine solvents. When these solvents which have good affinity with polyethylene glycol are used, various reactions can completely be performed in a solution.

The nucleoside compound represented by the formula (I-3') changes in its solubility depending on properties of a polyethylene glycol chain introduced into the site of the nuclei acid base. Addition of a suitable amount of, for example, diethyl ether or diisopropyl ether to the solution of the nucleoside compound or a derivative thereof, makes it possible to precipitate and recover the compound or derivative. It is also effective to carry out recrystallization from 2-propanol to recover the nucleoside compound or derivatives thereof. In this case, recovered product is of high purity.

The nucleoside compound represented by the formula (I-3') can also be utilized as a starting material at a terminal site for synthesis of oligonucleotides or as a building block for building of nucleotide chain.

(5) Method for Producing Nucleotide Block and Oligonucleotide Using the Same

The method for producing nucleotide block and the method for producing oligonucleotide using the same according to the present invention is as follows. The nucleotide derivative represented by the above formula (I-4) is reacted with 3'-O- and 5'-O-unprotected nucleoside derivative or nucleotide derivative represented by the above formula (II) optionally in the presence of a suitably selected activating agent to obtain a nucleotide having the structure represented by the above formula (III), and the compound represented by the formula (IV) is synthesized via said nucleotide of the formula (III). See the following formula (5-7).

Specifically, the compound (III) can be obtained by reacting the compounds (I-4) and (II) as they are, but the compound (III) can be further smoothly obtained by allowing an activating agent such as benzimidazole or benzotriazole to be present in the reaction of the compounds (I-4) and (II).

Further characteristic of this production method is that a phosphorus atom of the compound (III) obtained by the reaction of the compounds (I-4) and (II) or the reaction in the presence of a suitably selected activating agent is oxidized or sulfurized to prepare the compound (IV), and then this is isolated and reacted with a phosphorylating agent (5-III) as shown later in the formula (5-14), whereby again the (I-4) type compound can be obtained. This is further reacted with the (II) type compound, whereby the oligonucleotide chain can be sequentially extended.

In this case, when $R^1$ of the compound (I-4) is a succinyl group having a polyethylene glycol methyl ether residue or at least one of the protective groups of bases has a polyethylene glycol methyl ether residue, the compound (III) resulting from the reaction of the compounds (I-4) and (II) can be recovered using a nonsolvent for polyethylene glycol, such as diethyl ether, then reacted with the phosphorylating agent (5-III), and further condensed with the compound (II). If this procedure is repeated, the (III) type compound of a desired chain length is obtained. If the trivalent phosphorus atom of the (III) type compound is converted to a pentavalent atom, the compound (IV) can also be obtained.

Moreover, in the above method for production of nucleotide block and oligonucleotide using the properties of the polyethylene glycol bearing protective group, 5'-hydroxyl group of the by-product that may result from the reaction with 3'-hydroxyl group of the compound (II) during the reaction of the compounds (I-4) and (II), may be masked with triethylsilyl group, triisopropylsilyl group or tert-butyldimethylsilyl group and the products may be recovered in a solvent such as diethyl ether, before the reaction with the phosphorylating agent (5-III) is effected.

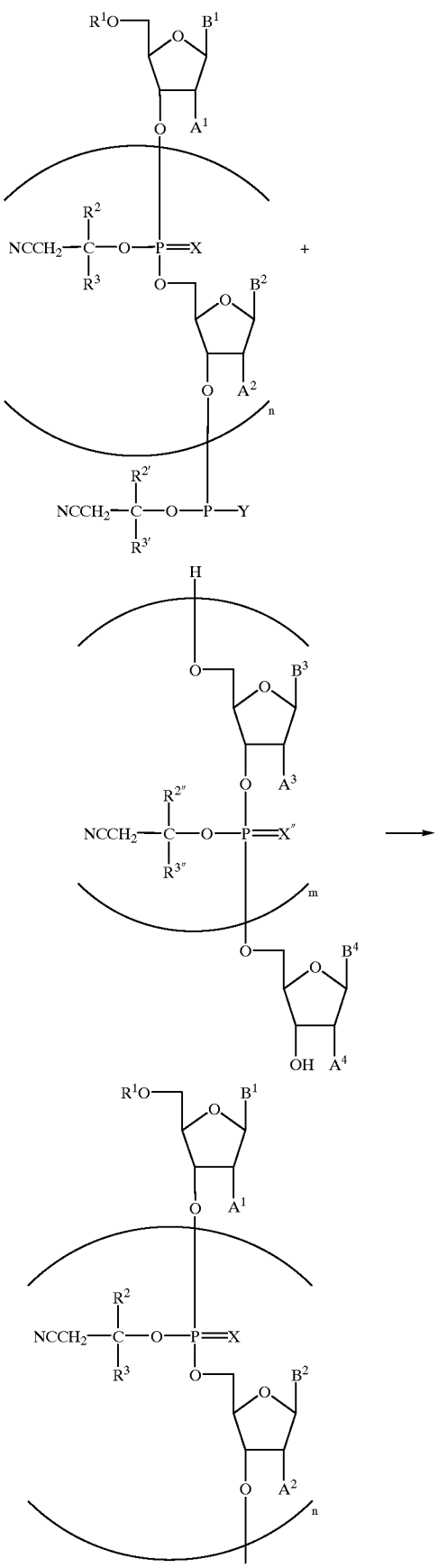

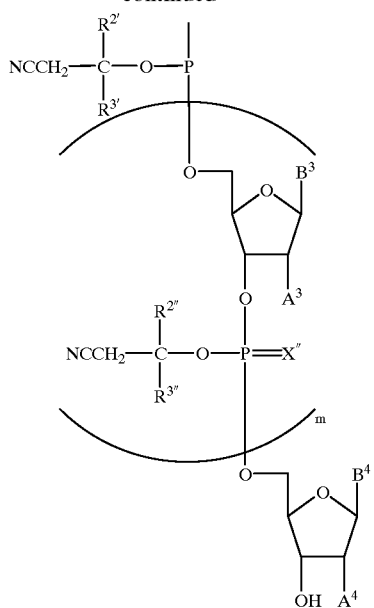

+ HY (5-7)

(in the above formula, $B^1$, $B^2$, $B^3$, $B^4$, $R^2$, $R^3$, $R^{2'}$, $R^{3'}$, $R^{2''}$, $R^{3''}$, $R^1$, $A^1$, $A^2$, $A^3$, $A^4$, X, X" and n and m are the same as defined in the above formula (IV), and Y is the same as defined in the above formula (I-4)).

The method for the production of nucleotide blocks or oligonucleotides in the present invention is characterized in that a nucleotide derivative represented by the above formula (I-4) is reacted with a 3'-O- and 5'-O-unprotected nucleoside derivative or nucleotide derivative represented by the above formula (II) to obtain the nucleotide represented by the above formula (III) and a trivalent phosphorus atom of the resulting nucleotide is oxidized or sulfurized to pentavalent phosphorus atom. The reaction formula is exemplified by the above formula (5-7). Furthermore, the present nucleotide block or oligonucleotide is a compound represented by the above formula (IV), and a precursor thereof is a nucleotide represented by the above formula (III).

As the bases represented by $B^1$ and $B^2$ in the above formula (I-4), mention may be made of purine derivatives such as derivatives of adenine, guanine and hypoxanthine, and pyrimidine derivatives such as derivatives of cytosine, thymine and uracil. Specific examples thereof are 1-thyminyl group, 1-(N-3-benzoylthyminyl) group, 1-(N-4-benzoylcytosinyl) group, 1-(N-4-anisoylcytosinyl) group, 9-(N-6-benzoyladeninyl) group, 9-(N-6, N-6-bisbenzoyladeninyl) group, and 9—(N-2-isobutyrylguaninyl) group, and B' represented by the following formula (4).

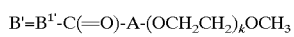  (4)

(in which $B^{1'}$ represents one of the groups represented by the following formula (1), k represents an integer of 3 or more, A is a divalent group and represents an arylene group or an alkylene group having a straight or branched chain which may contain a hetero-atom).

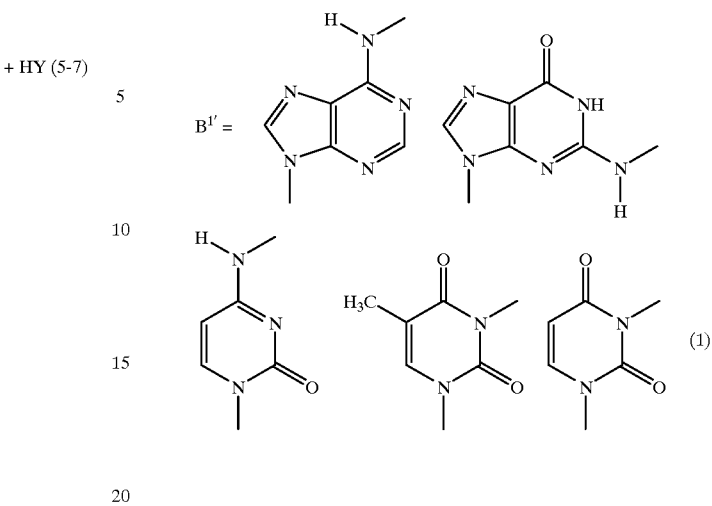

A and A' each includes, for example, 1,4-phenylene group, methylene group and dimethylethylene group.

As the bases represented by $B^3$ and $B^4$ in the above formula (II), mention may be made of purine derivatives such as derivatives of adenine, guanine and hypoxanthine, and pyrimidine derivatives such as derivatives of cytosine, thymine and uracil. Specific examples thereof are 1-thyminyl group, 1-(N-3-benzoylthyminyl) group, 1-(N-4-benzoylcytosinyl) group, 1-(N-4-anisoylcytosinly) group, 9-(N-6-benzoyladeninyl) group, 9-(N-6, N-6-bisbenzoyladeninyl) group and 9-(N-2-isobutyrylguaninyl) group.

Furthermore, as $R^2$, $R^3$, $R^{2'}$, $R^{3'}$, $R^{2''}$ and $R^{3''}$ in the above formulas (I-4) and (II), mention may be made of, for example, hydrogen atom, methyl group, ethyl group, n-propyl group, isopropyl group, isobutyl group, sec-butyl group, tert-butyl group, n-pentyl group, 1-ethylpropyl group, cyclohexyl group, n-nonyl group, 2-phenylethyl group, 2-(methylthio) ethyl group, phenyl group, 1,1-diethyl-3-butenyl group and/or 1,1-dimethyl-2-phenylethyl group. $R^1$ in the above formula (I-4) includes, for example, trityl group, 4-methoxytrityl group, and 4,4'-dimethoxytrityl group besides, succinyl group having polyethylene glycol methyl ether residue at one end.

Y in the above formula (I-4) includes, for example, imidazolyl group, 2-methylimidazolyl group, 4-methylimidazolyl group, 2,4-dimethylimidazolyl group, triazolyl group, and other azolyl groups.

The alkoxy group represented by $A^1$, $A^2$, $A^3$ and $A^4$ in the above formulas (I-4) and (II) includes, for example, methoxy group and ethoxy group, and the trialkylsilyloxy group including, for example, tert-butyldimethylsilyloxy group.

The present nucleotide block and oligonucleotide can be easily produced by oxidizing or sulfurizing the trivalent phosphorus atom of the nucleotide represented by the formula (III) to a pentavalent atom. See the following formula (5-12).

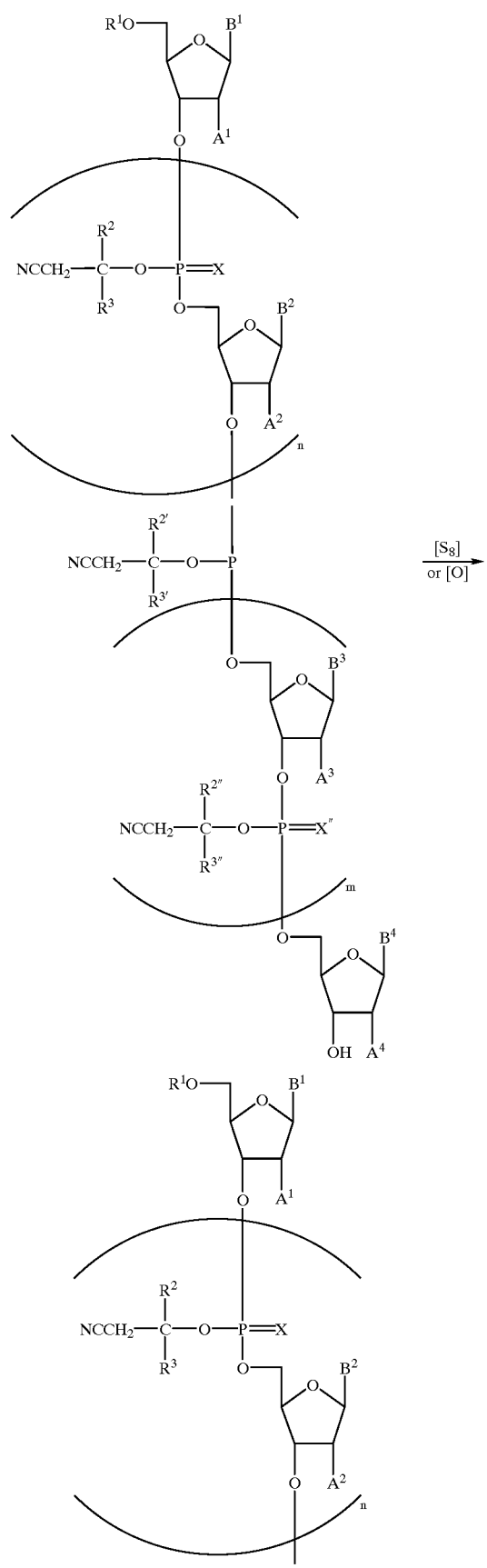
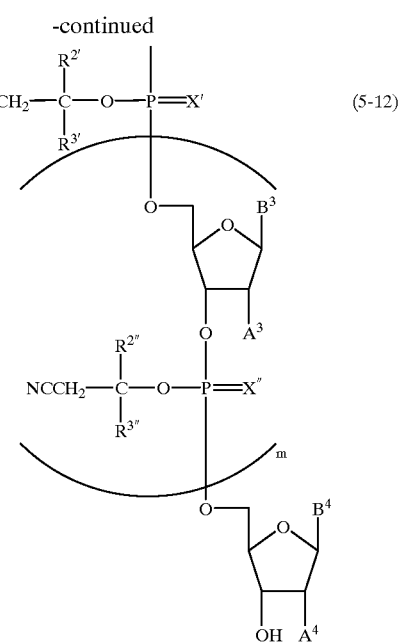
(in the above formula, $B^1, B^2, B^3, B^4, R^2, R^3, R^{2\prime}, R^{3\prime}, R^{2\prime\prime}, R^{3\prime\prime}, R^1, A^1, A^2, A^3, A^4, X, X^{\prime}, X^{\prime\prime}$ and n and m are the same as defined in the above formula (IV)).
Furthermore, the nucleotide represented by the above formula (I-4) can be easily produced in accordance with the reaction shown by the following formula (5-14).
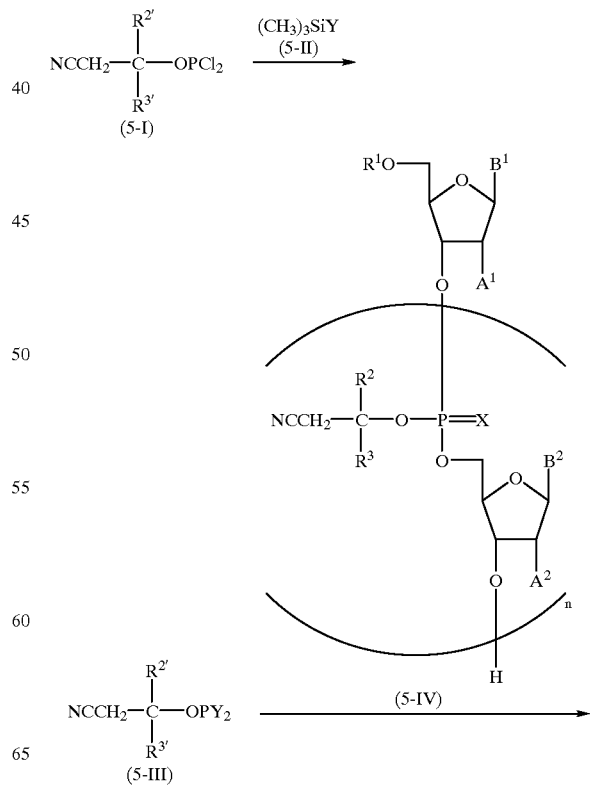

-continued

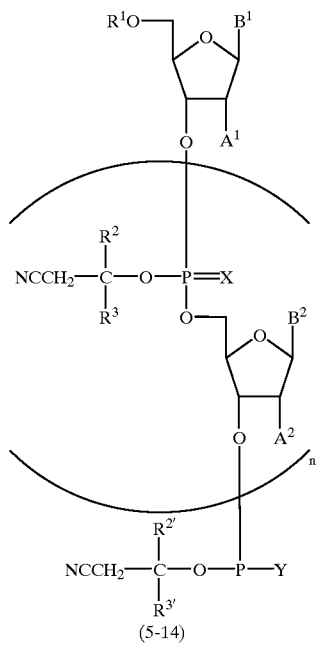

(5-14)

(in the above formula, $B^1$, $B^2$, $R^2$, $R^3$, $R^{2'}$, $R^{3'}$, $R^1$ $A^1$, $A^2$, X and n are the same as defined in the above formula (IV), and Y is the same as defined in the above formula (I-4)).

The above reaction is attained in the following manner. That is, organooxydichlorophosphine represented by the formula (5-I) in the above formula (5-14) which is a starting material is reacted with N-trimethylsilylazole compound represented by the formula (5-II) to obtain organooxybisazolylphosphine represented by the formula (5-III). Then, 5'-O- and base-protected nucleoside derivative or 5'-O- and base-protected nucleotide derivative represented by the formula (5-IV) in the formula (5-14) is vacuum dried or is dissolved in an organic solvent such as pyridine or 1,4-dioxane and subjected to azeotropic dehydration, and then the product is mixed and reacted with the above organooxy-bisazolylphosphine in an amount of 0.8–1.2 equivalent to the 5'-O- and base-protected nucleoside or 5'-O- and base-protected nucleotide derivative in an organic solvent solution such as in toluene, pyridine, tetrahydrofuran, chloroform or acetonitrile under the condition of –80° C. to room temperature. The reaction at lower temperature gives a higher yield of the nucleotide derivative represented by the above formula (I-4). Preferably, the organic solvent is one which has previously been dried with a drying agent and then purified by distillation. When chloroform is used as the organic solvent, the yield of the desired nucleotide is further improved. The completion of the reaction can be confirmed by measuring $^{31}$P-NMR spectrum of the reaction mixture. Since this reaction proceeds highly selectively from the starting organooxydichlorophosphine represented by the above formula (5-I) to the desired nucleotide, the synthesis can be performed in situ without isolation and purification, and the reaction mixture can be used in situ for the synthesis of nucleotide represented by the above formula (III).

The reaction of the above formula (5-7) can also be attained in the following manner. 3'-O- and 5'-O-unprotected nucleoside derivative or nucleotide derivative represented by the formula (II) in an amount of 1–2 equivalents to the nucleotide represented by the above formula (I-4) is vacuum dried or is dissolved in an organic solvent such as pyridine and subjected to azeotropic dehydration, and then the product is mixed and reacted with the above nucleotide derivative in an organic solvent solution such as in pyridine, chloroform or acetonitrile under the condition of –80° C. to room temperature, whereby the 5'-position hydroxyl group of the 3'-O- and 5'-O-unprotected-nucleoside derivative or nucleotide derivative is selectively reacted. Thus, the reaction is performed. Preferably, the organic solvent is one which has previously been dried with a drying agent and then purified by distillation. When pyridine is used as the organic solvent, the yield of the desired nucleotide represented by the above formula (III) is further improved. The completion of the reaction can be confirmed by measuring $^{31}$P-NMR spectrum of the reaction mixture. In this reaction, the higher the bulkiness of the substituents $R^{2'}$ and $R^{3'}$ in the formula (I-4) is, the higher the selectivity of coupling reaction with 5' hydroxyl group is, and especially, when the sums of the van der Waals volume of $R^{2'}$ and $R^{3'}$ is 49 (angstrom)$^3$ or more, the selectivity is excellent.

According to the method for producing the nucleotide block and the method for producing oligonucleotide using the same in the present invention, a nucleotide derivative represented by the above formula (I-4) is reacted with a 3'-O- and 5'-O-unprotected nucleoside or nucleotide derivative to synthesize a compound represented by the above formula (IV) via a nucleotide having the structure represented by the formula (III), and especially when Y of the compound (I-4) is an imidazolyl group or a 4-methylimidazolyl group in the step of the reaction of the compound (I-4) with (II), the reaction can further smoothly produce the compound (III) if a reaction accelerator is allowed to be present.

Examples of the reaction accelerator are imidazole compounds such as benzimidazole and 3-nitroimidazole, and triazole compounds such as benzotriazole, 3-methyltriazole, and 3-nitrotriazole. Solvents used for the reaction are preferably chloroform, acetonitrile, toluene and pyridine. The reaction can be carried out at –80° C. to 50° C. Addition amount of the reaction accelerator is preferably 1–10 equivalents to the compound (I-4).

In the present invention, in the case of having a polyethylene glycol methyl ether residue as the protective group for 5'-hydroxyl group or base of the compound (I-4), the compound (III) resulting from the reaction of the compound (I-4) and the compound (II) can be recovered using a poor solvent for polyethylene glycol, such as diethyl ether, then reacted with phosphorylation agent (5-III), and further condensed with the compound (II). This procedure can be repeated to obtain a (III) type compound of a desired chain length, and finally the trivalent phosphorus atom is converted to a pentavalent atom to give the compound (IV).

In this process, 5'-hydroxyl group of by-products that may be produced by the reaction with 3'-hydroxyl group of the compound (II) during the reaction of the compound (I-4) with the compound (II), can be masked with triisopropylsilyl group or the like.

As the masking agent, chlorotriisopropylsilane, chloro-tert-butyldimethylsilane, chloro-tert-butyldiphenylsilane, and the like can be used, but for accelerating this reaction, there may be used together imidazole compounds such as imidazole, 2-methylimidazole and 2-ethylimidazole. And, silylation agents such as triethylsilylimidazole, tert-butyldimethylsilylimidazole and the like can be used as the masking agent.

The reaction solvents are preferably dimethylformamide, dichloromethane, chloroform, acetonitrile and the like. The reaction can be carried out at 0–50° C. Amount of the solvent is preferably 0.1–0.5 equivalent to the compound (II).

The reaction of the above formula (5-12) can also be attained by mixing and reacting the nucleotide synthesized as above in the form of a reaction mixture without subjecting to isolation and purification with, for example, elemental sulfur in an amount of 1–3 equivalents to said nucleotide. The completion of the reaction can be confirmed by measuring $^{31}$P-NMR spectrum of the reaction mixture. The resulting nucleotide block can be readily isolated and purified by separation extraction and column chromatography at high purity.

Furthermore, the 3'-O- and 5'-O-unprotected nucleotide derivative represented by the above formula (II) which is another starting material in production of nucleotide can be easily produced by removing the protective group $R^1$ from the nucleotide block or oligonucleotide represented by the above formula (IV).

The nucleotide and nucleotide block produced by the above method are useful as an intermediate for chemical synthesis of oligonucleotide.

EXAMPLES

The compounds of the invention will now be explained in greater detail by way of the following examples which are in no way intended to limit the invention.

Example 1-1 a) Synthesis of DNA synthesis reagent represented by the following Formula (1-18), wherein $A^1$ is a hydrogen atom, $B^1$ is a 1-thyminyl group $R^{2'}$ is a hydrogen atom, $R^{3'}$ is an n-propyl group, $R^1$ is a 4,4'-dimethoxytrityl Group and Y is a 4-methylimidazolyl Group in the formula (I-1) Above.

(1-18)

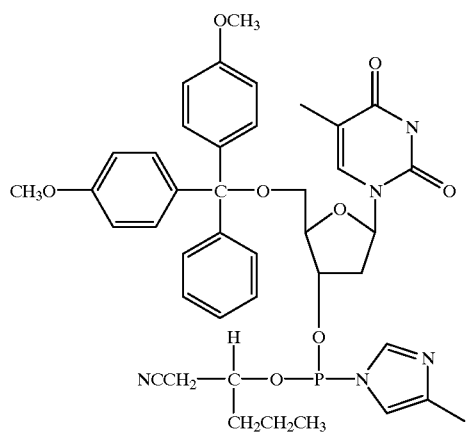

To toluene (5 ml) there were added 0.267 g (1.25 mmol) of 2-cyano-1-n-propylethoxydichlorophosphine and 0.425 g (2.75 mmol) of trimethylsilyl-4-methylimidazole under an argon atmosphere at room temperature, and reaction was conducted for 5 minutes. After by-product chlorotrimethylsilane and toluene were removed under reduced pressure for 10 minutes at room temperature, the residual toluene and excess trimethylsilyl-4-methylimidazole were removed under reduced pressure for 2 hours at 35° C. to obtain 2-cyano-1-n-propylethoxybis (4-methylimidazolyl) phosphine as a colorless transparent oil. This was dissolved in 2.5 ml of chloroform-d, and the solution (0.5 M) was added to 0.678 g (1.25 mmol) of 5'-O-(4,4'-dimethoxytrityl) thymidine that had been dried under reduced pressure for 2 hours, under an argon atmosphere at room temperature. Upon reaching homogeneity, the mixture was allowed to stand overnight for reaction to obtain a phosphorazolide compound represented by the formula (1-18) above.

The $^{31}$P NMR of the obtained compound (external standard: $(CH_3O)_3P$=140 ppm, $CDCl_3$) was δ; 123.0, 125.4 ppm (measuring the $^{31}$P NMR spectrum with a 161.7 MHz NMR measuring apparatus).

b) Reaction between phosphorazolide compound represented by the formula (1-18) (in situ DNA synthesis reagent) and Methanol Approximately 0.1 ml (about 2 mmol) of methanol was added to the $CDCl_3$ reaction solution of the phosphorazolide obtained above under an argon atmosphere at room temperature, to obtain a quantitative amount of a compound represented by the following formula (1-19). The $^{31}$P NMR of the, obtained compound (external standard: $(CH^3O)_3P$= 140 ppm, $CDCl_3$) was δ; 138.8, 138.9, 139.3, 139.5 ppm (measuring the $^{31}$P NMR spectrum with a 161.7 MHz NMR measuring apparatus).

(1-19)

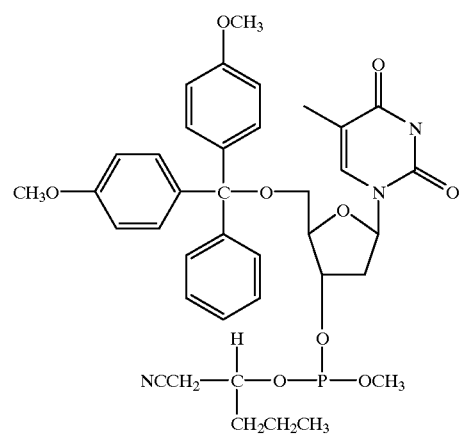

c) Monosubstitution selectivity of the reaction of organooxybisazolylphosphine with 5'-O- and base-protected Nucleoside.

When a phosphorazolide compound is produced according to a) above, the side reaction represented by the formula (1-20) below proceeds, giving a disubstituted by-product represented by the following formula (1-21). The $^{31}$P NMR spectrum of the reaction solution obtained by the reaction of b) above was measured, and the monosubstitution selectivity of the reaction was calculated by equation (F) below. As a result, the monosubstitution selectivity was found to be 92%.

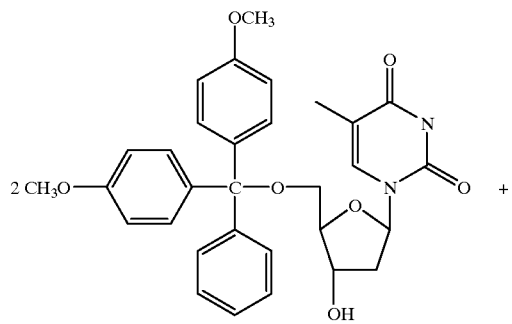
(1-20)

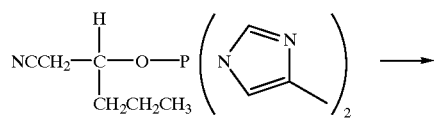

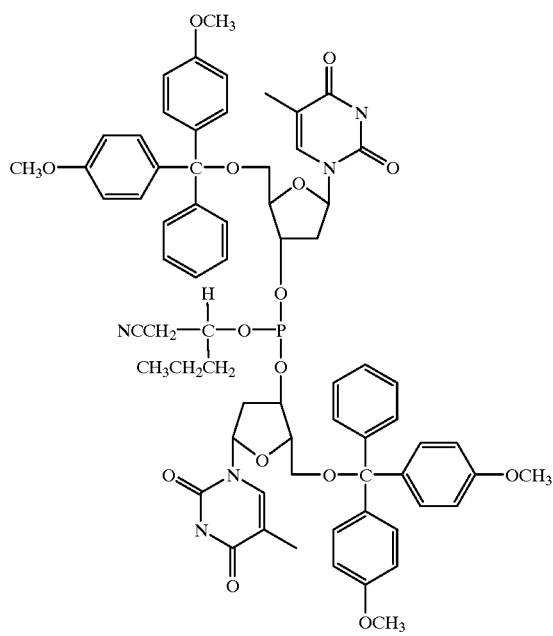

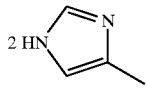

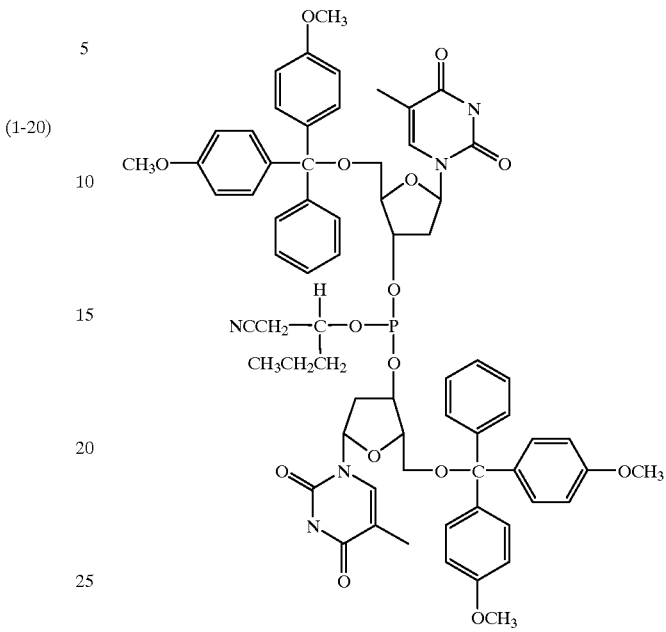
(1-21)

Monosubstitution selectivity (%)=[(19)/((19)+(21))]×100  (F)

where (19) and (21) represent the respective molar composition ratios of compounds (1–19) and (1–20) in the reaction solution as determined by the $^{31}$P NMR spectra.

Application Example 1-1

Synthesis of (Thymidine eicosamer) in a DNA automatic synthesizer by the solid phase method, using the phosphorazolide compound Obtained in Example 1-1 as the In situ DNA synthesis reagent.

The phosphorazolide compound represented by the formula (1-18) was produced in the same manner as Example 1-1 a) above, except that after dissolving 5'-O-(4,4'-dimethoxytrityl) thymidine in 1,4-dioxane, the solution was subjected to azeotropic dehydration and acetonitrile was used as the reaction solvent with 2-cyano-1-n-propylethoxybis(4-methylimidazolyl) phosphine, at a concentration of 0.1 M.

This 0.1 M acetonitrile reaction solution was used directly as the starting material to synthesize a thymidine eicosamer in a DNA automatic synthesizer by solid phase reaction according to the protocol of the amidite method. The resulting reaction product mixture was analyzed by reverse phase HPLC and found to have an average condensation yield of 97.5%.

Examples 1-2 to 1-14

Phosphorazolide compounds for Examples 1-2 to 1-14 shown in Tables 1-1 and 1-2 below were produced by the same procedure as Example 1-1. In Example 1-1 a), the residual toluene and excess trimethylsilyl-4-methylimidazole were distilled off under reduced pressure for 2 hours at 35° C. but in Examples 1-2 to 1-14 they were removed under reduced pressure for 2 hours at 35–50° C. as necessary. The $^{31}$P NMR spectrum chemical shift (δ) of each phosphorazolide compound and its methanol reaction product (OMe form) (external standard: $(CH_3O)_3P$=140 ppm, measured with a 161.7 MHz NMR measuring apparatus), the van der Waals volume sum for the substituents $R^{2'}$ and $R^{3'}$ {substituent volume $(R^{2'}+R^{3'})$} and the monosubstitution selectivity as defined by equation (F) above were determined in the same manner as Example 1-1. Each phosphorazolide compound was also used to synthesize the corresponding thymidine or cytidine eicosamer in a DNA automatic synthesizer by solid phase reaction according to the standard protocol of the amidite method, in the same manner as Example 1-1, and the average condensation yield (solid phase synthesis condensation yield) was determined. These values are shown in Table 1-1 and Table 1-2.

Comparative Examples 1-1 and 1-2

The compounds for Comparative Example 1-1 and Comparative Example 1-2 listed in Table 1-2 were produced by the same procedure as Example 1-1, and were evaluated in the same manner as Example 1-1, giving the results shown in Table 1-2.

The compounds of Examples 1-2 to 1-13 and Comparative Examples 1-1 and 1-2 are phosphorazolide compounds represented by the following formula (1-22) wherein $A^1$ is a hydrogen atom and $R^1$ is a 4,4'-dimethoxytrityl group in the formula (I-1) above.

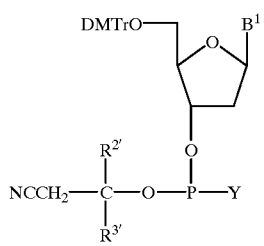

(1-22)

wherein DMTr represents a 4,4'-dimethoxytrityl group and $B^{40}$, $R^{2'}$, $R^{3'}$ and Y are the same as in the formula (I-1) above.

The compounds of Examples 1-14 is phosphorazolide compounds represented by the following formula (1-23) wherein $R^1$ is a succinyl group having polyethylene glycol methyl ether residue (number-average molecular weight (Mn) 2000) at one end in the formula (I-1) above.

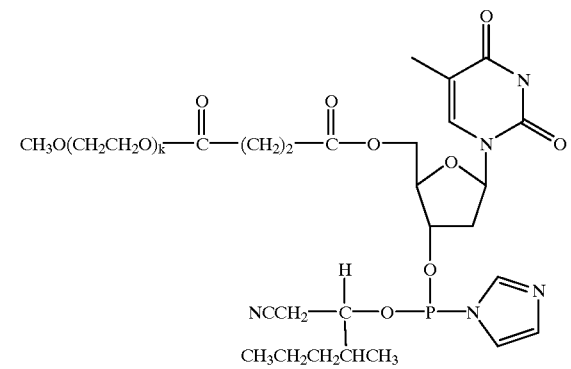

(1-23)

TABLE 1-1

Physical property and reactivity data for DNA synthesis reagents

| No. | $B^1$ | $R^{2'}$ | $R^{3'}$ | Y | $^{31}$P NMR δ value for compound (I-1) (ppm) | $^{31}$P NMR δ value for OMe form (ppm) | Substituent volume ($R^{2'} + R^{3'}$) (Å$^3$) | Monosubstitution selectivity (%) | Solid phase synthesis condensation yield (%) |
|---|---|---|---|---|---|---|---|---|---|
| Example 1-1 | T | H | n-C$_3$H$_7$ | 4-MeIm | 123.0, 125.4 | 138.8, 138.9, 139.3, 139.5 | 49.36 | 92 | 97.5 |
| Example 1-2 | T | H | i-C$_3$H$_7$ | Im | 124.5, 124.9, 125.0, 128.1 | 139.4, 139.6, 140.0, 140.2 | 49.88 | 95 | |
| Example 1-3 | T | H | i-C$_3$H$_7$ | 4-MeIm | 124.5, 124.9, 125.0, 128.1 | | 49.88 | | 97.9 |
| Example 1-4 | T | H | t-C$_4$H$_9$ | 2-MeIm | 127.9, 128.2, 128.4, 130.8 | 140.5, 140.8, 141.3, 141.7 | 64.27 | | 97.1 |
| Example 1-5 | T | H | t-C$_4$H$_9$ | 4-MeIm | 127.9, 128.2, 128.4, 130.8 | 140.5, 140.8, 141.3, 141.7 | 64.27 | 98 | 97.2 |
| Example 1-6 | T | H | C$_6$H$_5$ | 4-MeIm | | 137.9, 138.2, 138.9, 139.1 | 73.16 | 87 | 97.3 |
| Example 1-7 | T | H | CH(CH$_3$)—CH$_2$CH$_2$CH$_3$ | 4-MeIm | 123.2, 123.7, 124.1, 124.3, 124.9, 125.7, 128.1, 128.6 | 139.2, 139.3, 139.4, 139.6, 139.7, 140.0, 140.2, 140.4 | 76.19 | 96 | 98.0 |
| Example 1-8 | T | CH$_3$ | i-C$_4$H$_9$ | 4-MeIm | 115.0, 116.4, 118.0, 118.1 | 133.5, 133.6, 134.2 | 78.29 | 98 | 97.2 |

TABLE 1-2

Physical property and reactivity data for DNA synthesis reagents

| No. | $B^1$ | $R^{2'}$ | $R^{3'}$ | Y | $^{31}$P NMR δ value for compound (I-1) (ppm) | $^{31}$P NMR δ value for OMe form (ppm) | Substituent volume ($R^{2'} + R^{3'}$) (Å$^3$) | Monosubstitution selectivity (%) | Solid phase synthesis condensation yield (%) |
|---|---|---|---|---|---|---|---|---|---|
| Example 1-9 | T | H | C(C$_2$H$_5$)$_2$—CH$_2$CHCH$_2$ | Im | 127.1, 129.8, 130.5, 133.8 | 140.9, 141.2, 141.7, 142.3 | 114.39 | 98 | 98.0 |
| Example 1-10 | T | H | C(C$_2$H$_5$)$_2$—CH$_2$CHCH$_2$ | 4-MeIm | 127.3, 129.2, 130.4, 133.3 | 140.8, 141.1, 141.6, 142.1 | 114.39 | 98 | 98.2 |

TABLE 1-2-continued

Physical property and reactivity data for DNA synthesis reagents

| No. | $B^1$ | $R^{2'}$ | $R^{3'}$ | Y | $^{31}P$ NMR δ value for compound (I-1) (ppm) | $^{31}P$ NMR δ value for OMe form (ppm) | Substituent volume ($R^{2'} + R^{3'}$) (Å$^3$) | Monosubstitution selectivity (%) | Solid phase synthesis condensation yield (%) |
|---|---|---|---|---|---|---|---|---|---|
| Example 1-11 | $C^{Bz}$ | H | $C(C_2H_5)_2$—$CH_2CHCH_2$ | 4-MeIm | 127.5, 130.9, 131.5, 134.6 | 141.0, 141.1, 141.9, 142.1 | 114.39 | 99 | 96.8 |
| Example 1-12 | $A^{Bz}$ | H | $C(C_2H_5)_2$—$CH_2CHCH_2$ | 4-MeIm | 129.8, 130.2, 131.4, 134.2 | 140.8, 141.6, 142.0, 142.2 | 114.39 | >97 | |
| Example 1-13 | $G^{iBu}$ | H | $C(C_2H_5)_2$—$CH_2CHCH_2$ | 4-MeIm | | 140.9, 141.1, 141.5, 142.4 | 114.39 | 98 | |
| Example 1-14 | (mPEG T*) | H | $C(C_2H_5)_2$—$CH_2CHCH_2$ | Im | 127.5, 128.0 130.5, 132.7 | | 114.39 | >98 | |
| Comparative Example 1-1 | T | H | H | 4-MeIm | | 138.5, 138.6 | 8.34 | 83 | 93.0 |
| Comparative Example 1-2 | T | H | $C_2H_5$ | 4-MeIm | 123.0, 125.5 | 138.6, 138.7, 139.1 | 36.65 | | 92.5 |
| Example 3-1 | $C^{mPEG}$ | H | $C(C_2H_5)_2$—$CH_2CHCH_2$ | Im | (Compound I-3) 127.4, 130.8 131.5, 134.3 | | 114.39 | 99 | |

*)$R^1$ is a succinyl group having a polyethyleneglycol methyl ether residue (mPEG portion Mn 2000) at one end.

(In Tables 1-1 and 1-2, T in column $B^1$ represents a 1-thyminyl group, $C^{Bz}$ represents a 1-(N-4-benzoylcytosinyl) group, $A^{Bz}$ represents a 9-(N-6-benzoyladeninyl) group, $G^{iBu}$ represents a 9-(N-2-isobutyrylguaninyl) group, and $C^{mPEG}$ represents 1-cytosinyl group N-protected with a functional group having a methoxypolyethylene glycol chain (Mn=350).)

The structures of substituents $R^{2'}$, $R^{3'}$ and Y are as shown in Table 1-3.

TABLE 1-3

The abbreviations in the columns for substituents $R^{2'}$, $R^{3'}$ and Y in Tables 1-1 and 1-2 represent the following structures.

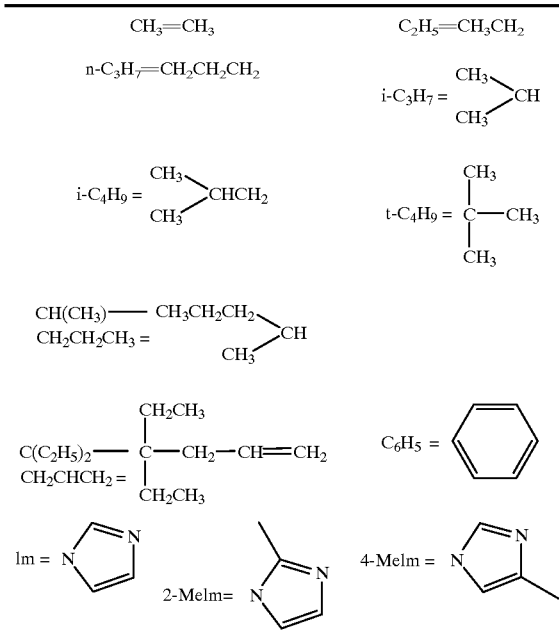

As clearly shown by the examples and comparative examples in Tables 1-1 and 1-2, in the case of the conventional phosphoric protective group where $R^{2'}=R^{3'}=H$ (Comparative Example. 1-1), using the reaction solution directly for solid phase synthesis of the DNA oligomer in situ results in an average condensation yield of at most 93.0%, and it is therefore not useful as an in situ DNA synthesis reagent. In comparison, however, the phosphorazolide compounds of Example 1-1 and Examples 1-3 to 1-11 were all 96.8% or higher. The +3% difference in yield has a major effect when the compounds are used as intermediate starting materials for chemical synthesis of DNA oligomers. Thus, when the phosphorazolide compounds of the invention are used as intermediate starting materials for chemical synthesis of DNA oligomers, they can be used as in situ DNA synthesis reagents without isolation and purification.

It is also clear from Tables 1-1 and 1-2 that the average condensation yields for solid phase synthesis of DNA oligomers tends to be higher with higher monosubstitution selectivity when producing each DNA synthesis reagent, and that there is also a rather good correlation with the sum of the van der Waals volumes of substituents $R^{2'}$ and $R^{3'}$.

In other words, among the compounds represented by the formula (I-1) above, those wherein the sum of the van der Waals volumes of substituents $R^{2'}$ and $R^{3'}$ is at least 49 (angstroms)$^3$ are particularly useful as in situ DNA synthesis reagents.

Example 2-1

Synthesis of monoalkylamino-type phosphoramidite compound represented by the following formula (2-21), wherein $A^1$ is a hydrogen atom, $B^1$ is a 1-thyminyl group, $R^{2'}$ is a hydrogen atom, $R^{3'}$ is a Tert-butyl group, $R^1$ is a 4,4'-dimethoxytrityl group and Y is an isopropylamino group in the Formula (I-2) above.

(2-21)

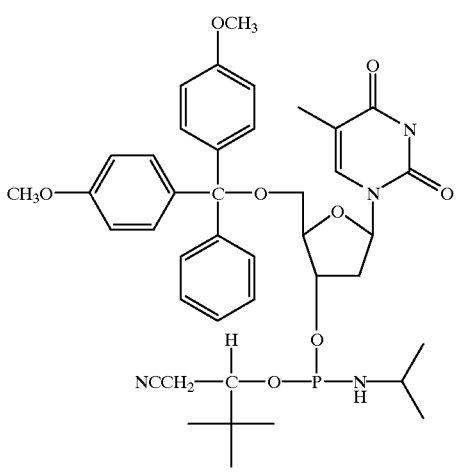

To toluene (5 ml) there were added 0.332 g (1.46 mmol) of 2-cyano-1-tert-butylethoxydichlorophosphine and 0.495 g (3.21 mmol) of trimethylsilyl-4-methylimidazole under an argon atmosphere at room temperature, and reaction was conducted for 5 minutes. After by-product chlorotrimethylsilane and toluene were removed under reduced pressure for 10 minutes at room temperature, the residual toluene and excess trimethylsilyl-4-methylimidazole were removed under reduced pressure for 2 hours at 40° C. to obtain 2-cyano-1-tert-butylethoxybis(4-methylimidazolyl) phosphine as a colorless transparent oil. Under an argon atmosphere at room temperature, this 2-cyano-1-tert-butylethoxybis(4-methylimidazolyl)phosphine was dissolved in 2.9 ml of chloroform-d, and the solution (0.5 M) was added to 0.794 g (1.46 mmol) of 5'-O-(4,4'-dimethoxytrityl)thymidine that had been dried under reduced pressure for 2 hours. Upon reaching homogeneity, the mixture was allowed to stand overnight for reaction to obtain a nucleotide derivative represented by the formula (2-22) below. The $^{31}$P NMR of the obtained compound (external standard: $(CH_3O)_3P$=140 ppm, $CDCl_3$) δ was 127.9, 128.2, 128.4, 130.8 ppm (measuring the $^{31}$P NMR spectrum with a 161.7 MHz NMR measuring apparatus).

(2-22)

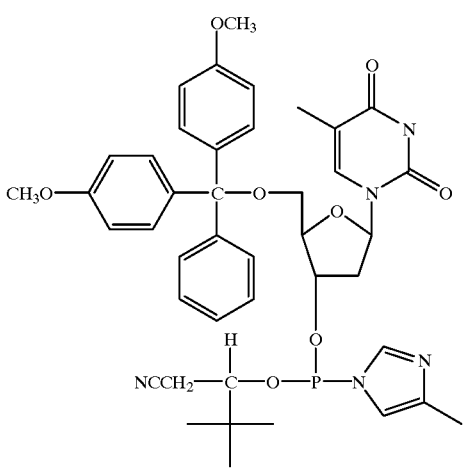

To the reaction solution obtained above there was added 0.086 g (1.46 mmol) of isopropylamine at room temperature for reaction, to obtain a quantitative amount of a monoalkylamino-type phosphoramidite derivative represented by the formula (2-21) above, as the target compound. The $^{31}$P NMR of the obtained product (external standard: $(CH_3O)_3P$=140 ppm, $CDCl_3$) δ was 141.8, 142.4, 144.5, 145.8 ppm (measuring the $^{31}$P NMR spectrum with a 161.7 MHz NMR measuring apparatus).

Application Example 2-1

Synthesis of d (TTTTTTTTTTTTTTTTTTTT) (thymidine eicosamer) in a DNA automatic synthesizer by the solid phase method, Using the monoalkylamino-type phosphoramidite compound represented by the Formula (2-21) Above.

A monoalkylamino-type phosphoramidite compound was produced in the same manner as Example 2-1, except that after dissolving 5'-O-(4,4'-dimethoxytrityl)thymidine in 1,4-dioxane, the solution was subjected to azeotropic dehydration and acetonitrile was used as the reaction solvent with 2-cyano-1-tert-butylethoxybis(4-methylimidazolyl) phosphine, at a concentration of 0.1 M.

The 0.1 M acetonitrile reaction solution of the compound was used directly as the starting material to synthesize a thymidine eicosamer in a DNA automatic synthesizer by solid phase reaction according to the protocol of the amidite method, using tetrazole as the catalyst. The resulting reaction product mixture was analyzed by reverse phase HPLC and found to have an average condensation yield of 99.1%.

Examples 2-2 to 2-8

The monoalkylamino-type and dialkylamino-type phosphoramidite compounds of Examples 2-2 to 2-8 listed in Tables 2-1 and 2-2 were produced by the same procedure as Example 2-1. The $^{31}$P NMR spectrum chemical shift (δ) of each monoalkylamino-type or dialkylamino-type phosphoramidite compound {the formula (I-2) above} and its precursor nucleotide derivative {the formula (I-1') above} (external standard: $(CH_3O)_3P$=140 ppm, measured with a 161.7 MHz NMR measuring apparatus)} and the van der Waals volume sum for the substituents $R^{2'}$ and $R^{3'}$ {substituent volume $(R^{2'}+R^{3'})$} are shown in Table 2-1. A 0.1 M acetonitrile reaction solution containing each monoalkylamino-type or dialkylamino-type phosphoramidite compound was also used directly as a starting material to synthesize the corresponding thymidine, cytidine or adenosine eicosamer in a DNA automatic synthesizer by solid phase reaction according to the standard protocol of the amidite method, using tetrazole as the catalyst, and the average condensation yields (solid phase synthesis condensation yields) listed in Table 2-1 were obtained. The structures of substituents $R^{3'}$, Y and X in Table 2-1 are as shown in the following Table 2-2.

The monoalkylamino-type and dialkylamino-type phosphoramidite compounds listed as Examples 2-2 to 2-8 are compounds represented by the following formula (2-23) wherein $A^1$ is a hydrogen atom and $R^1$ is a 4,4'-dimethoxytrityl group in the formula (I-2) above.

(2-23)

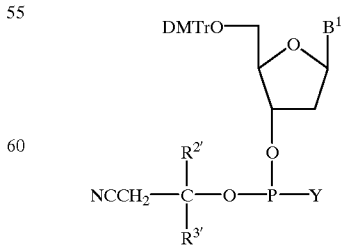

wherein DMTr represents a 4,4'-dimethoxytrityl group and $B^1$, $R^{2'}$, $R^{3'}$ and Y are the same as in the formula (I-2) above.

TABLE 2-1

Physical, property and reactivity data for DNA synthesis reagents

| No. | B¹ | R²' | R³' | X | Compound (I-1') $^{31}$P NMR δ value (ppm) | Y | Compound (I-2) $^{31}$P NMR δ value (ppm) | Substituent volume (R²' + R³') (Å³) | Solid phase synthesis condensation yield (%)* |
|---|---|---|---|---|---|---|---|---|---|
| Example 2-1 | T | H | t-C₄H₉ | 4-MeIm | 127.9, 128.2, 128.4, 130.8 | HN(i-C₃H₇) | 141.8, 142.4, 144.5, 145.8 | 64.27 | 99.1 |
| Example 2-2 | A$^{Bz}$ | H | n-C₃H₇ | 4-MeIm | 124.2, 124.7, 125.5, 126.9 | HN(t-C₄H₉) | 140.4, 141.4, 142.2, 144.1 | 49.36 | 98.3 |
| Example 2-3 | T | H | i-C₃H₇ | 4-MeIm | 124.5, 124.9, 125.0, 128.1 | HN(i-C₃H₇) | 141.3, 141.4, 142.6, 143.9 | 49.88 | 99.0 |
| Example 2-4 | C$^{Bz}$ | H | CH(CH₃)—CH₂CH₂CH₃ | 4-MeIm | 123.1, 124.1, 124.7, 125.3, 126.2, 126.6, 128.8, 129.6 | HN(c-C₆H₁₁) | 140.7, 141.0, 141.3, 141.7, 142.6, 143.2, 143.7, 144.2 | 76.19 | 98.5 |
| Example 2-5 | A$^{Bz}$ | H | n-C₅H₁₁ | 4-MeIm | 123.7, 124.1, 125.5, 126.8 | HN(n-C₄H₉) | 140.3, 141.1, 142.3 | 75.52 | 97.9 |
| Example 2-6 | T | H | CH(CH₃)—CH₂CH₂CH₃ | Im | 123.2, 123.7, 124.1, 124.3, 124.9, 125.7, 128.1, 128.6 | HN(i-C₄H₉) | 141.0, 141.2, 141.3, 141.6, 141.8, 142.6, 143.7, 144.0 | 76.19 | 99.0 |
| Example 2-7 | A$^{Bz}$ | H | i-C₄H₉ | 4-MeIm | 124.7, 124.8 125.3, 126.9 | HN(neo-C₅H₁) | 140.7, 141.7, 141.8, 143.1 | 64.48 | 97.6 |
| Example 2-8 | T | H | CH(CH₃)—CH₂CH₂CH₃ | 4-MeIm | 122.9, 123.4, 123.8, 124.1 124.7, 125.6, 128.5, 129.1 | N(CH₃)₂ | 146.3, 146.6, 146.7, 147.1, 147.4, 148.1, 148.2, 148.8 | 76.19 | |

*)Average condensation yield when compound (I-2) was used as an in situ DNA synthesis reagent.
(In Table 2-1, T in column B¹ represents a 1-thyminyl group, C$^{Bz}$ represents a 1-(N-4-benzoylcytosinyl) group and A$^{Bz}$ represents a 9-(N-6-benzoyladeninyl) group.)

TABLE 2-2

The abbreviations in the columns for substituents R³', X and Y in Table 2-1 represent the following structures.

n-C₃H₇=CH₃CH₂CH₂ i-C₃H₇ = (CH₃)₂CH i-C₄H₉ = (CH₃)₂CHCH₂ t-C₄H₉ = (CH₃)₃C—CH₃ n-C₅H₁₁=CH₃CH₂CH₂CH₂CH₂

CH(CH₃)—CH₃CH₂CH₂
CH₂CH₂CH₃ = (CH₃)CH

HN(i-C₃H₇) = (CH₃)₂CHNH

HN(n-C₄H₉)=CH₃CH₂CH₂CH₂NH

HN(i-C₄H₉) = (CH₃)₂CHCH₂NH

HN(t-C₄H₉) = HN—C(CH₃)₃

HN(neo-C₅H₁₁) = HNCH₂—C(CH₃)₃

HN(c-C₆H₁₁) = HN—C₆H₁₁ (cyclohexyl)

TABLE 2-2-continued

The abbreviations in the columns for substituents $R^{3'}$, X and Y in Table 2-1 represent the following structures.

Im = 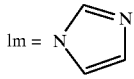     4-MeIm = 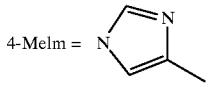

Example 3-1

Synthesis of compound represented by the following formula (3-1), wherein $B^{1'}$=cytosine derivative, $R^{2'}$ hydrogen Atom, $R^{3'=1,1}$-diethyl-3-butenyl group, $R^1$=4,4'-dimethoxytrityl group, $A^1$=hydrogen atom, Y=imidazolyl Group and A=1,4-phenylene Group in the formula (I-3) above.

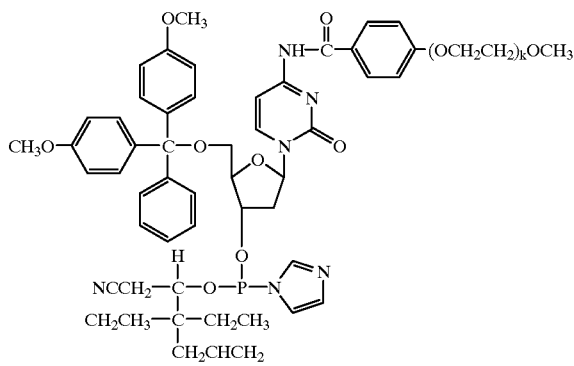

(3-1)

To a toluene solution (5 ml) containing 2-cyano-1-(1,1-diethyl-3-butenyl) ethoxydichlorophosphine (350 mg, 1.25 mmol) there was added trimethylsilylimidazole (0.40 ml, 2.75 mmol) under an argon atmosphere at room temperature, and reaction was conducted for 5 minutes. After by-product chlorotrimethylsilane and toluene were removed under reduced pressure for 10 minutes at room temperature, the residual toluene and excess trimethylsilylimidazole were removed under reduced pressure for 2 hours at 55° C. to obtain 2-cyano-1-(1,11-diethyl-3-butenyl) ethoxybisimidazolylphosphine as a colorless transparent oil. The $^3$P NMR of the compound (161.7 MHz, external standard: $(CH_3O)_3P$=140 ppm, $CDCl_3$) was δ=109.3 ppm.

This 2-cyano-1-(1,1-diethyl-3-butenyl)ethoxy bisimidazolylphosphine was dissolved in chloroform-d (2.5 ml) to make a 0.50 M solution, and under an argon atmosphere at room temperature, this was added to a 5'-O- and base-protected-2'-deoxycytidine-polyethylene glycol derivative (number-average molecular weight (Mn) of polyethylene glycol monomethyl ether (mPEG) portion (abbreviated mPEG portion Mn, and so on)=350, compound of the formula (3-3) where $B^{1'}$=cytosine derivative, $R^1$=4,4'-dimethoxytrityl, $A^1$=hydrogen and A=1,4-phenylene, 1.20 g, 1.25 mmol) that had been dried under reduced pressure for 2 hours under an argon atmosphere at room temperature. Upon reaching homogeneity, the mixture was allowed to stand overnight for reaction to obtain the target phosphorazolide compound (I-3, Y=imidazolyl, in situ DNA synthesis reagent). The $^{31}$P NMR of the obtained compound (161. 7 MHz, external standard: $(CH_3O)_3P$=140 ppm, $CDCl_3$) was δ=134.3, 131.5, 130.8, 127.4 ppm.

The monosubstitution selectivity of the reaction was 99% as determined in the same manner as Example 1-1. The data for the 31P NMR spectrum and monosubstitution selectivity are shown in Table 1-2.

Example 3-2

Synthesis of compound of the formula (I-3) above where $B^{1'}$= thymine derivative, $R^{2'}$=hydrogen atom, $R^{3'}$=isopropyl group, $R^1$=4,4'-dimethoxytrityl group. $A^1$=hydrogen atom, Y=4-methylimidazolyl group and A=1.4-phenylene group.

2-cyano-1-isopropylethoxydichlorophosphine (196 mg, 0.92 mmol), trimethylsilyl-4-methylimidazole (0.31 ml, 2.02. mmol) and a 5'-O- and base-protected-thymidine-polyethylene glycol derivative (mPEG portion Mn=350, compound of the formula (3-3) where $B^{1'}$=thymine derivative, $R^1$=4,4'-dimethoxytrityl, $A^1$ =hydrogen atom and A=1,4-phenylene, 1.19 g, 1.23 mmol) were used in the same method as Example 3-1 to obtain the target phosphorazolide compound (I-3, Y=4-methylimidazolyl, in situ DNA synthesis reagent). The $^{31}$P NMR of the obtained compound (161.7 MHz, external standard: $(CH_3O)_3P$=140 ppm, $CDCl_3$) was δ138.2, 127.9, 124.4 ppm.

Example 3-3

Synthesis of compound of the formula (I-3) above where $B^{1'}$=adenine derivative, $R^{2'}$=hydrogen atom, $R^{3'}$=tert-butyl group, $R^1$=4,4-dimethoxytrityl group, $A^1$=hydrogen atom, Y=imidazolyl group and A=1,4-phenylene Group.

2-cyano-1-tert-butylethoxydichlorophosphine (240 mg, 1.05 mmol), trimethylsilylimidazole (0.34 ml, 2.32 mmol) and a 5'-O- and base-protected-2'-deoxyadenosine-polyethylene glycol derivative (mPEG portion Mn=350, compound of the formula (3-3) where $B^{1'}$=adenine derivative, $R^1$=4,4$^1$-dimethoxytrityl, $A^1$=hydrogen atom and A=1,4-phenylene, 1.41 g, 1.40 mmol) were used in the same method as Example 3-1 to obtain the target phosphorazolide compound (I-3, Y=imidazolyl, in situ DNA synthesis reagent). The $^{31}$P NMR of the obtained compound (161.7 MHz, external standard: $(CH_3O)_3P$ 140 ppm, $CDCl_3$) was δ132.1, 129.2, 128.9, 128.5 ppm.

Example 3-4

Synthesis of compound represented by the formula (3-4), wherein $B^{1'}$=guanine derivative, $R^{2'}$=hydrogen atom, $R^{3'}$=1,1-diethyl-3-butenyl group, $R^1$=4,4'-dimethoxytrityl group, $A^1$=hydrogen atom, Y=imidazolyl group and A=4-substituted benzyl group in the formula (I-3) above.

(3-4)

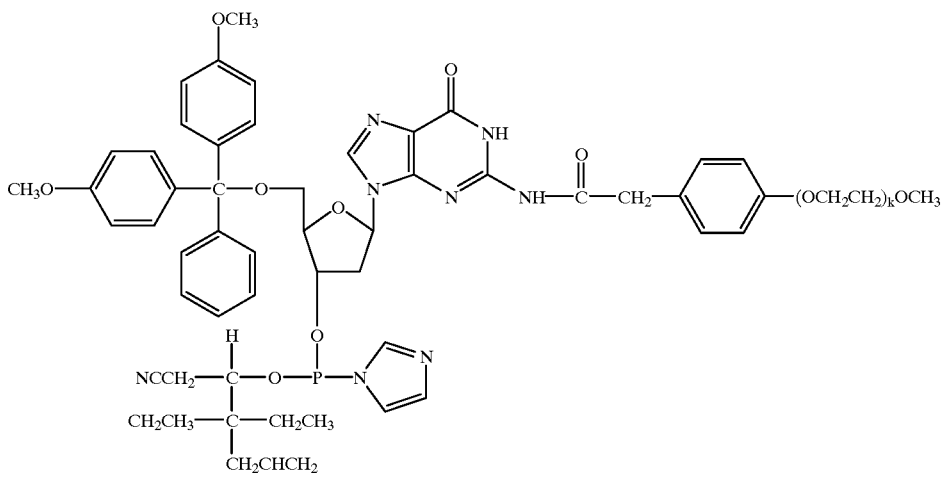

2-cyano-1-(1,1-diethyl-3-butenyl) ethoxydichlorophosphine (379 mg, 1.34 mmol), trimethylsilylimidazole (0.43 ml, 2.96 mmol) and a 5'-O- and base-protected-2'-deoxyguanosine-polyethylene glycol derivative (mPEG portion Mn=350, compound of the formula (3-3) where $B^{1'}$=guanine derivative, $R^1$=4,4'-dimethoxytrityl, $A^1$=hydrogen atom and A=4-substituted benzy, 1.62 g, 1.56 mmol) were used according to the same method as Example 3-1 to obtain the target phosphorazolide compound (I-3, Y=imidazolyl, in situ DNA synthesis reagent). The $^{31}$P NMR of the obtained compound (161.7 MHz, external standard: $(CH_3O)_3P$=140 ppm, $CDCl_3$) was δ=132.5, 131.6, 128.6, 128.4 ppm.

Example 3-5

Synthesis of compound of the formula (I-3) above where $B^{1'}$=guanine derivative, $R^{2'}$=hydrogen atom, $R^{3'}$=1,1-diethyl-3-butenyl group, $R^1$=4,4'-dimethoxytrityl group, $A^1$ hydrogen atom, Y=imidazolyl group and A=methylene group.

2-cyano-1-(1,1-diethyl-3-butenyl) ethoxydichlorophosphine (383 mg, 1.43 mmol), trimethylsilylimidazole (0.46 ml, 3.14 mmol) and a 5'-O- and base-protected-2'-deoxyguanosine-polyethylene glycol derivative (mPEG portion Mn=350, compound of the formula (3-3) where $B^{1'}$=guanine derivative, $R^1$=4,4'-dimethoxytrityl, $A^1$=hydrogen atom and A=methylene, 1.50 g, 1.56 mmol) were used according to the same method as Example 3-1 to obtain the target phosphorazolide compound (I-3, Y=imidazolyl, in situ DNA synthesis reagent). The $^{31}$P NMR of the obtained compound (161.7 MHz, external standard: $(CH_3O)_3P$=140 ppm, $CDCl_3$) was δ=132.4, 129.0, 128.5, 128.4 ppm.

Application Example 3-1

A chloroform-d solution (2 ml) containing a base-protected- 2'-deoxycytidine-polyethylene glycol derivative (mPEG portion Mn350, compound of the formula (3-3) where $B^{1'}$=cytosine derivative, $R^1$=$A^1$=hydrogen atom and A=1,4-phenylene, 650 mg, 1 mmol) was added to a chloroform-d reaction solution (2.0 ml, approximately 1 mmol) of the phosphorazolide compound (in situ DNA synthesis reagent) obtained in Example 3-1, under an argon atmosphere at 0° C., and the mixture was allowed to stand overnight at 4° C. for reaction to obtain a dimer. According to $^{31}$P NMR, the selectivity of the coupling reaction with 5' hydroxy group of the 2nd nucleoside was 5' hydroxyl/3' hydroxyl=92/8. The $^{31}$P NMR of the obtained compound (161.7 MHz, external standard: $(CH_3O)_3P$=140 ppm, $CDCl_3$) was δ=141.7, 141.0, 140.8, 140.4 ppm.

When a portion of the reaction solution (2 ml, total weight: 2.95 g, approximately 0.5 mmol) was measured out and added to anhydrous diethyl ether (30 ml) while stirring, a white solid precipitated within 2–5 minutes. After an additional 10 minutes of vigorous stirring, the mixture was allowed to stand overnight at 4° C. The ether was removed by decantation, and the residue was washed 3 times with anhydrous ether (5 ml). Measurement of the $^{31}$P NMR of the residue that has been vacuum-dried gave the same spectrum obtained above, confirming that the target dimer had been obtained (882 mg, 88% yield).

Application Example 3-2

A chloroform/pyridine mixed solution (1/2 (v/v), 5 ml) containing $N^6$-benzoyl-2'-deoxyadenosine (890 mg, 2.5 mmol) was added to a chloroform reaction solution (5 ml, approximately 2.5 mmol) of the phosphorazolide compound (in situ DNA synthesis reagent) obtained in Example 3-1, under an argon atmosphere at 0° C., and the mixture was allowed to stand overnight at 4° C. for reaction for dimerization. Elemental sulfur (160 mg, 5 mmol) that had been already dried under reduced pressure for at least 3 hours was added into the reaction solution at room temperature, and the mixture was stirred for 12 hours. The solvent was removed under reduced pressure below room temperature, and the residue was redissolved in chloroform (20 ml) and purified by silica gel column chromatography (chloroform/methanol=100/3) to obtain the target dimer (thiophosphoric acid triester) (3.43 g, 88% yield). The $^{31}$P NMR of the obtained compound (161.7 MHz, external standard: $(CH_3O)_3P$=140 ppm, $CDCl_3$) was δ=66.3, 66.0, 65.6 ppm. A chloroform/pyridine mixed solution (1/2 (v/v), 5 ml) containing N-isobutyryl-2'-deoxyguanosine (890 mg, 2.5 mmol) was used in the same manner to obtain the target dimer (thiophosphoric acid triester) (3.15 g, 81% yield). The $^{31}$P NMR of the obtained compound (161.7 MHz, external standard: $(CH_3O)_3P$=140 ppm, $CDCl_3$) was δ=66.6, 66.2, 65.8, 65.4 ppm.

The compounds of the formula (I-3') above will now be explained in greater detail, with the understanding that these examples are not limitative. In Examples 3'-1 to 3'-6, the polyethylene glycol monomethylether used had a number average molecular weight of 350, and in Example 3'-7 it had a number average molecular weight of 2,000.

Example 3'-1

Synthesis of nucleoside compound (mPEG portion Mn=350) represented by the formula (3'-1) where $A^1$, $R^1$ and $R^4$ are all hydrogen atoms, $B^{1'}$ is a cytosine derivative and A is 1,4-phenylene in the formula (I-3')

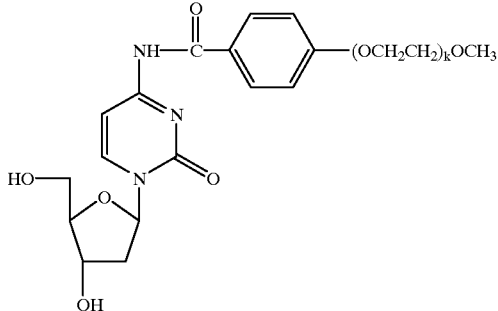

(3'-1)

2'-deoxycytidine monohydrochloride (13.18 g, 52 mmol) that had been subjected to azeotropic dehydration with pyridine (2×20 ml) under an argon gas stream was suspended in anhydrous pyridine (120 ml) and cooled to 0° C. Chlorotrimethylsilane (19.0 ml, 150 mmol) was added and the mixture was stirred for 15 minutes. The benzoyl chloride-monomethoxypolyethylene glycol; $CH_3O(CH_2CH_2O)_kC_6H_4COCl$ {34.9 mmol, mPEG portion Mn=350; $^1$H-NMR (400 MHz, CDCl$_3$, TMS) δ8.07 (d, J=8.8Hz,2H,ArH), 6.99 (d, J=8.8 Hz,2H,ArH), 4.23 (t, J=4.8 Hz,2H,ArOCH$_2$), 3.89 (t, J=4.8 Hz,2H,OCH$_2$), 3.79–3.51 (m), 3.38(s,3H,OCH$_3$) ppm} prepared by the reaction of benzoic acid-monomethoxypolyethylene glycol (C. J. van Staveren, et al., J. Am. Chem. Soc., 110, 4994 (1988)) with thionyl chloride, was dissolved in anhydrous pyridine (80 ml) under an argon gas stream, and was added to the previously prepared reaction solution and stirred at room temperature for 2 hours. After cooling to 0° C., distilled water ((10 ml) was added to the reaction mixture , and after concentration to approximately 1/2, concentrated ammonium hydroxide (20 ml) was added at 0° C. and the mixture was stirred for 20 minutes. The solvent was removed under reduced pressure, a saturated sodium bicarbonate aqueous solution (200 ml) was added, and extraction was performed with chloroform (3×100 ml). The organic layer was washed with water a (2×200 ml) and dried over anhydrous sodium sulfate. After filtration, the filtrate was condensed under reduced pressure and the residue was purified by silica gel column chromatography (chloroform/methanol=100/5) to obtain the target PEG-modified 2'-deoxycytidine represented by the formula (3'-1) (18.85 g, 82.4% yield). The $^1$H-NMR of the obtained compound (400 MHz, CDCl$_3$, TMS) was δ=9.30 (brs,1H,NH), 8.41 (d, J=7.2 Hz,1H,H6), 7.83 (d, J=7.6 Hz,2H,ArH), 7.48 (br,1H,H5), 6.92 (d, J=7.6 Hz,2H,ArH), 6.29–6.10 (m,1H,H1'), 5.07 (brs,1H), 4.74–4.40 (br,2H), 4.27–4.00 (m,3H), 4.00–3.42 (m), 3.36 (s,3H,OCH$_3$), 2.70–2.50 (m,1H,H2"), 2.35–2.18 (m,1H,H2') ppm.

Example 3'-2

Synthesis of nucleoside compound (mPEG portion Mn=350) represented by the formula (3'-2) where $A^1$, $R^1$ and $R^4$ are all hydrogen atoms, $B^{1'}$ is a adenine derivative and A is 1,4-phenylene in the formula (I-3').

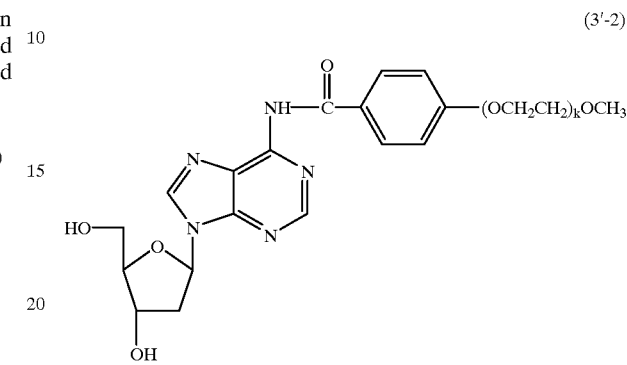

(3'-2)

2'-deoxyadenosine (5.025 g, 20 mmol) that had been subjected to azeotropic dehydration with pyridine (2×20 ml) was suspended in anhydrous pyridine (50 ml) under an argon gas stream and cooled to 0° C. Chlorotrimethylsilane (12.7 ml, 100 mmol) was added and the mixture was stirred for 15 minutes at room temperature. The benzoyl chloride-monomethoxypolyethylene glycol $CH_3O(CH_2CH_2O)_kC_6H_4COCl$ (21.3 mmol, mPEG portion Mn=350) was dissolved in anhydrous pyridine (50 ml) under an argon gas stream, and was added to the previously prepared reaction solution and stirred overnight. After recooling to 0° C., distilled water (10 ml) was added to the reaction mixture, and after concentration to approximately 1/2, concentrated ammonium hydroxide (20 ml), was added at 0° C. and the mixture was stirred for 15 minutes. The solvent was removed under reduce pressure, a saturated sodium bicarbonate aqueous solution (100 ml) was added, and extraction was performed with chloroform (3×100 ml). The organic layer was washed with saturated brine (100 ml) and dried over anhydrous sodium sulfate. After filtration, the filtrate was condensed under reduced pressure and the residue was purified by silica gel column chromatography (chloroform/methanol=100/3→100/5) to obtain the target PEG-modified 2'-deoxyadenosine represented by the formula (3'-2) (5.50 g, 39.1% yield). The $^1$H-NMR of the obtained compound (400 MHz, CDCl$_3$, TMS) was δ=9.42 (s,1H,NH), 8.68 (s,1H,H8), 8.19 (s,1H,H2), 7.97 (d, J=8.4 Hz,2H,ArH), r 6.97 (d, J=8.4 Hz,2H,ArH), 6.47–6.36 (m,1H,H$_1$'), 5.79–5.65 (m,1H), 4.74 (br,1H), 4.30–4.03 (m,4H), 3.97–3.43 (m), 3.36 (s,3H, OCH$_3$), 2.96–2.83 (m,1H,H2"), 2.45–2.35 (m,1H,H2') ppm.

Example 3'-3

Synthesis of nucleoside compound (mPEG portion Mn=350) represented by the formula (3'-3) where $R^1$ is 4,4'-dimethoxytrimethyl, $A^1$ and $R^4$ are hydrogen atoms, $B^{1'}$ is a adenine derivative and A is 1,4-phenylene in the formula (I-3').

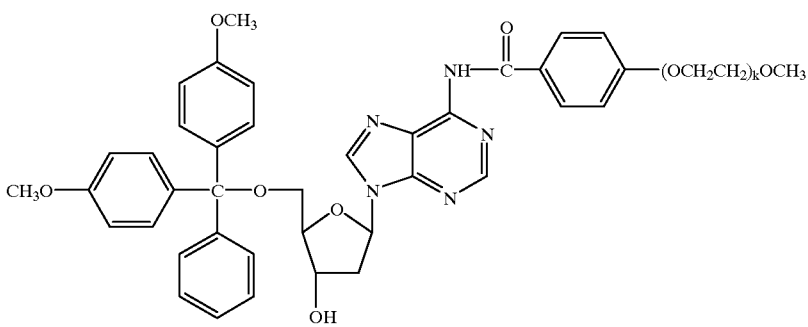

(3'-3)

The PEG-modified 2'-deoxyadenosine represented by the formula (3'-2) that was obtained in Example 3'-2 (4.643 g, 6.54 mmol, mPEG portion Mn=350) that had been subjected to azeotropic dehydration with pyridine (2×20 ml) was dissolved in anhydrous pyridine (30 ml) under an argon gas stream and cooled to 0° C. 4,4 '-dimethoxytrityl chloride (3.0 g, 9.0 mmol) was added and the mixture was stirred for 75 minutes at room temperature. Methanol (5 ml) was added to the reaction mixture, and the solvent was removed under reduced pressure. A saturated sodium bicarbonate aqueous solution (50 ml) was added, extraction was performed with chloroform (3×50 ml), and the organic layer was washed with water (50 ml) and dried over anhydrous sodium sulfate. After filtration, the filtrate was condensed under reduced pressure and the residue was purified by silica gel column chromatography (chloroform/methanol=100/3) to obtain the PEG-modified 5'-O-dimethoxytrityl-2'-deoxyadenosine represented by the formula (3'-3) (4.97 g, 75.7% yield). The $^1$H-NMR of the obtained compound (400 MHz, CDCl$_3$, TMS) was δ=9.45 (brs,1H,NH), 8.66 (s,1H,H8), 8.16 (s,1H, H2), 7.97 (d, J=8.4 Hz,2H,ArH), 7.42–7.08 (m,9H,ArH), 6.94 (d, J=8.4 Hz,2H,ArH), 6.73 (d, J=8.8 Hz,4H,ArH), 6.48 (t, J=6.4 Hz,1H,H1'), 4.98–4.62 (m,2H), 4.30–4.08 (m,3H), 3.95–3.42 (m), 3.34 (s,3H,OCH$_3$), 2.90–2.75 (m,1H,H2''), 2.68–2.46 (m,1H,H2') ppm.

Example 3'-4

Synthesis of nucleoside compound (mPEG portion Mn=350) represented by the formula (3'-4) where A$^1$, R$^1$ and R$^4$ are all hydrogen atoms, B$^{1'}$ is a thymine derivative and A is 1,4-phenylene in the formula (I-3').

(3'-4)

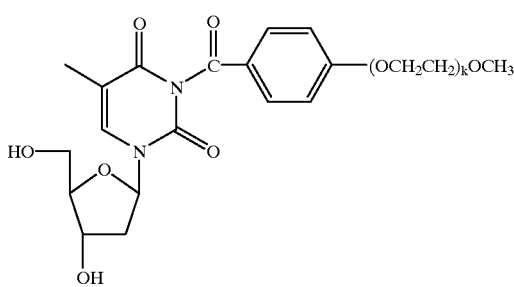

Thymidine (3.03 g, 12.5 mmol) that had been subjected to azeotropic dehydration with pyridine (2×20 ml) was suspended in anhydrous pyridine (40 ml) under an argon gas stream, and diisopropylethylamine (10.9 ml, 62.5 mmol) was added. Chlorotrimethylsilane (4.0 ml, 31.25 mmol) was added and the mixture was stirred for 30 minutes at room temperature. Benzoyl chloride-monomethoxypolyethylene glycol CH$_3$O(CH$_2$CH$_2$O)$_k$C$_6$H$_4$COCl (10.6 mmol, mPEG portion Mn=350) was dissolved in anhydrous pyridine (5 ml) under an argon gas stream, and was added to the previously prepared reaction solution and stirred overnight. After recooling to 0° C., a saturated potassium dihydrogen phosphate aqueous solution (40 ml) was added to the reaction mixture, and extraction was performed with chloroform (3×100 ml). The organic layer was washed with a saturated sodium bicarbonate aqueous solution (3×100 ml) and with water (100 ml) and dried over anhydrous sodium sulfate. After filtration, the filtrate was condensed under reduced pressure and the residue was purified by silica gel column chromatography (chloroform/methanol=100/3→100/5) to obtain the target PEG-modified thymidine represented by the formula (3'-4) (6.73 g, 91.5% yield). The $^1$H-NMR of the obtained compound (400 MHz, CDCl$_3$, TMS) was δ=7.86 (d, J=8.8 Hz,2H,ArH), 7.73 (s,1H,H6), 6.98 (d, J=8.8 Hz,2H,ArH), 6.21 (m,1H,H1'), 4.39 (br,1H), 4.19 (t, J=4.4 Hz,2H,ArOCH$_2$), 3.97–3.41 (m), 3.37 (s,3H, OCH$_3$), 2.38–2.12 (m,2H,H2' and H2''), 1.9 (s,3H,CH$_3$) ppm.

Example 3'-5

Synthesis of nucleoside compound (mPEG portion Mn=350) represented by the formula (3'-5) where R$^1$ is 4,4'-dimethoxytrityl, A$^1$ and R$^4$ are hydrogen atoms, B$^{1'}$ is a thymine derivative and A is 1,4-phenylene in the formula (I-3').

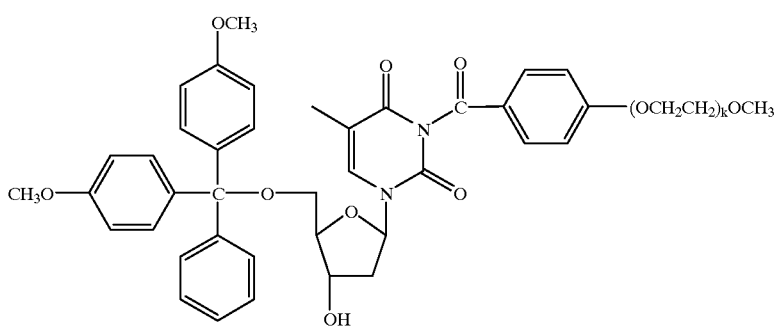

(3'-5)

The PEG-modified thymidine represented by the formula (3'-4) that was obtained in Example 3'-4 (8.30 g, 12.0 mmol) and had been subjected to azeotropic dehydration with pyridine (2×20 ml) was dissolved in anhydrous pyridine (50 ml) under an argon gas stream and cooled to 0° C. 4,4-dimethoxytrityl chloride (5.0 g, 15.0 mmol) was added and the mixture was stirred for 3 hours at room temperature. Methanol (5 ml) was added to the reaction mixture, and the solvent was removed under reduced pressure. A saturated sodium bicarbonate aqueous solution (100 ml) was added, extraction was performed with chloroform (3×100 ml), and the organic layer was washed with saturated brine (100 ml) and with water (100 ml), and then dried over anhydrous sodium sulfate. After filtration, the filtrate was condensed under reduced pressure and the residue was purified by silica gel column chromatography (chloroform/methanol=100/3) to obtain the PEG-modified 5'-O-dimethoxytrityl-thymidine represented by the formula (3'-5) (7.20 g, 60% yield). The $^{1}$H-NMR of the obtained compound (400 MHz, CDCl$_3$, TMS) was δ=7.85 (d, J=8.8 Hz,2H,ArH), 7.73 (s,1H,H6), 7.41 (d, J=7.2 Hz,2H,ArH), 7.38–7.20 (m,7H,ArH), 6.93 (d, J=8.8 Hz,2H,ArH), 6.84 (d, J=7.2 Hz,4H,ArH), 6.37 (t, J=6.8 Hz,1H,H1'), 4.55 (br,1H), 4.15 (t, J=4.8 Hz,2H, ArOCH$_2$), 4.03 (br,1H), 3.84 (t, J=4.8 Hz,2H,OCH$_2$), 3.78 (s,6H,ArOCH$_3$), 3.72–3.41 (m), 3.35 (s,3H,OCH$_3$), 2.42–2.25 (m,2H,H2' and H2"), 1.43 (s,3H,CH$_3$) ppm.

Example 3'-6

Synthesis of nucleoside compound (mPEG portion Mn 350) represented by the formula (3'-6) where $R^1$ is 4,4'-dimethoxytrityl, $A^1$ and $R^4$ are hydrogen atoms, $B^{1'}$ is a guanine derivative and A is methylene in the formula (I-3').

2'-Deoxyguanosine (2.85 g, 10 mmol) that had been subjected to azeotropic dehydration with pyridine (2×20 ml) was suspended in anhydrous pyridine (40 ml) at 0° C. under an argon gas stream, chlorotrimethylsilane (6.3 ml, 50 mmol) was added and the mixture was stirred for 30 minutes at room temperature. Thoroughly dried glycolic acid-monomethoxypolyethylene glycol (4.16 g, 10 mmol, mPEG portion Mn 350) separately prepared according to Staveren, et al.'s method (see C. J. van Staveren, et al., J. Am., Chem. Soc. 110, 4994 (1988)) was dissolved in anhydrous acetonitrile (20 ml) under an argon gas atmosphere, triethylamine (1.0 ml, 10 mmol) and pivaloyl chloride (1.23 ml, 10 mmol) were added at room temperature and the mixture was stirred for 30 minutes. This reaction solution was added to the previously prepared nucleoside solution and stirred for 3. The reaction solution was cooled to 0° C., distilled water (5 ml) was added to the reaction mixture, and after removing the solvent under reduced pressure to approximately 1/2, concentrated ammonium hydroxide (5 ml) was added at 0° C. and the mixture was stirred for 15 minutes. The solvent was removed under reduced pressure, saturated brine (50 ml) was added, and extraction was performed with chloroform (4×50 ml). The organic layer was washed with saturated brine (100 ml) and dried over anhydrous sodium sulfate. The solvent of the solution was removed under reduced pressure and the residue was subjected to azeotropic distillation with pyridine (3×20 ml), after which it was dissolved in anhydrous pyridine (50 ml), 4,4'-dimethoxytrityl chloride (3.38 g, 10.0 mmol) was added at 0° C. and the mixture was stirred for 75 minutes at room! temperature. Methanol (5 ml) was added to the reaction mixture, and the solvent was removed under reduced pressure. A saturated sodium bicarbonate aqueous solution (100

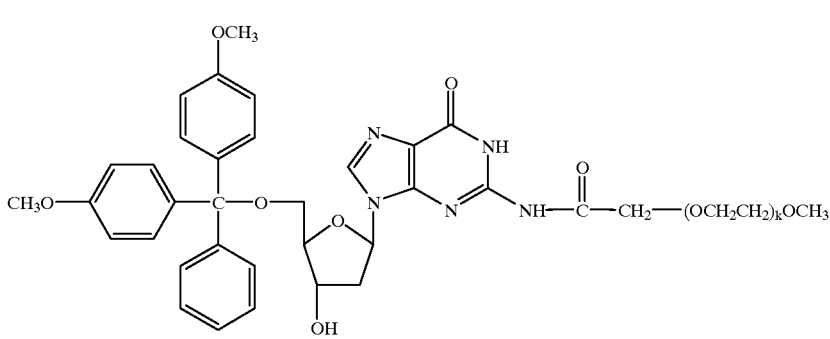

(3'-6)

ml) was added, extraction was performed with chloroform (3×100 ml), and the organic layer was washed with saturated brine (100 ml) and with water (100 ml), and then dried over anhydrous sodium sulfate. After filtration, the filtrate was condensed under reduced pressure and the residue was purified by silica gel column chromatography (chloroform/methanol=100/3) to obtain the PEG-modified 5'-O-dimethoxytrityl-2'-deoxyguanosine (5.94 g, 61% yield). The $^1$H-NMR of the obtained compound(400 MHz, CDCl$_3$, TMS) was δ=11.95 (brs,1H,NH), 10.02 (brs,1H,NH), 8.32 (s,1H,H8), 6.29 (t, J=4.4 Hz,1H,H1'), 5.05–4.60 (br,3H), 4.26 (s,1H,CH$_2$), 4.12–3.42 (m), 3.37 (s,1H,CH$_3$), 2.69–2.42 (m,2H,H2' and H2") ppm.

Example 3'-7

Synthesis of nucleoside compound where $A^1$, $R^1$ and $R^4$ are all hydrogen atoms, $B^{1'}$ is a cytosine derivative and A is 1,4-phenylene in the formula (I-3'), and introduction of monomethoxypolyethylene glycol-modified form (mPEG portion Mn 2000) into 2'-deoxycytidine nucleic acid base.

2'-deoxycytidine monohydrochloride (3.955 g, 15 mmol) that had been subjected to azeotropic dehydration with pyridine (2×20 ml) was suspended in anhydrous pyridine (40 ml) and cooled to 0° C. under an argon gas stream. Chlorotrimethylsilane (9.5 ml, 75 mmol) was added and the mixture was stirred for 20 minutes. Benzoyl chloride-monomethoxypolyethylene glycol CH$_3$O(CH$_2$CH$_2$O)$_k$C$_6$H$_4$COCl (11.8 mmol, mPEG portion Mn=2000) prepared according to the method shown in Example 3'-1 was dissolved in anhydrous pyridine (50 ml) under an argon gas stream, and was added to the previously prepared reaction solution and stirred at room temperature for 2.5 hours. After cooling to 0° C., distilled water (10 ml) was added to the reaction mixture, and after removing the solvent under reduced pressure for concentration to approximately 1/2, it was recooled to 0° C., concentrated ammonium hydroxide (10 ml) was added and the mixture was stirred for 15 minutes. The solvent was removed under reduced pressure, a saturated sodium bicarbonate aqueous solution (100 ml) was added, and extraction was performed with chloroform (3×100 ml). The organic layer was washed. with water (2×100 ml) and dried over anhydrous sodium sulfate. After filtration, the filtrate was condensed under reduced pressure and the residue was purified by silica gel column chromatography (chloroform/methanol=100/2→100/5) to obtain the PEG-modified 2'-deoxycytidine (5.470 g, 20% yield). The $^1$H-NMR of the obtained compound (400 MHz, CDCl$_3$, TMS) was δ=9.00 (brs,1H,NH), 8.46 (d, J=8.0 Hz,1H,H6), 7.87 (d, J=8.8 Hz,2H,ArH), 7.52 (br,1H,H5), 6.98 (d, J=8.8 Hz,2H,ArH), 6.22 (t, J=5.6 Hz,1H,H1'), 4.58–4.50 (br,2H), 4.36–4.15 (m,3H), 4.10–3.41 (m), 3.38 (s,3H,OCH$_3$), 2.62–2.52 (m,1H,H2"), 2.37–2.23 (m,1H,H2') ppm.

Example 5-1

Synthesis of nucleotide dimer block represented by the formula (5-15) below wherein m=n=0, $R^2$=hydrogen atom, $R^3$=1,1-diethyl-3-butenyl group, $R^1$=4,4'-dimethoxytrityl group, $B^1$=B=9-(N-6-benzoyladeninyl) group, $A^1$=$A^4$=hydrogen atom and X' sulfur atom in the formula (IV).

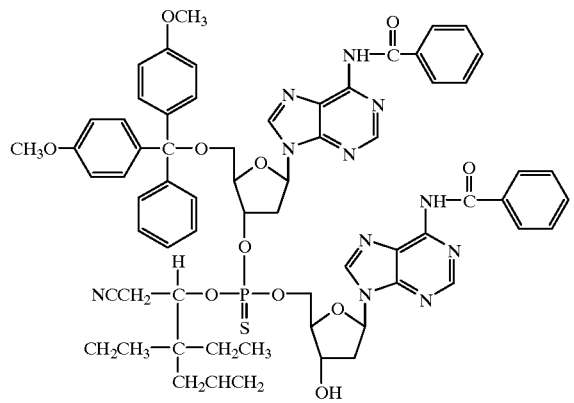

(5-15)

a) Synthesis of nucleotide represented by the formula (5-16) below wherein n=0, $R^{2'}$ hydrogen atom, $R^{3'}$1,1-diethyl-3-butenyl group, $R^1$=4,4'-dimethoxytrityl group, $B^1$=9-(N-6-benzoyladeninyl) group, $A^1$=hydrogen atom and Y=imidazolyl group in the formula (I-4).

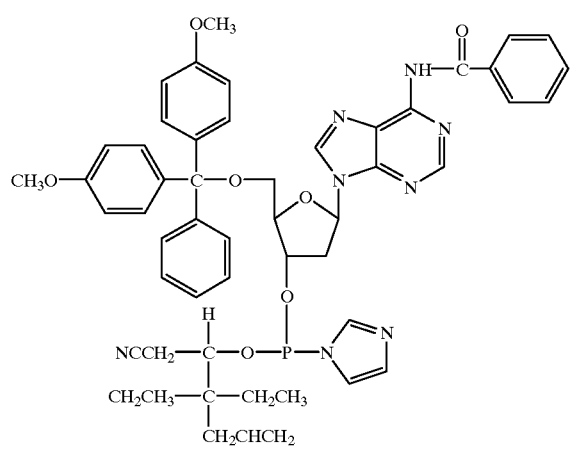

(5-16)

To toluene (3 ml) there were added 0.578 g (2.05 mmol) of 2-cyano-1-(1,1-diethyl-3-butenyl)ethoxydichlorophosphine and 0.632 g (4.50 mmol) of 1-(trimethylsilyl)imidazole under an argon atmosphere at room temperature, and reaction was conducted for 10 minutes. After by-product chlorotrimethylsilane and toluene were removed under reduced pressure for 25 minutes at room temperature, the residual toluene and excess 1-(trimethylsilyl)imidazole were removed under reduced pressure for 2 hours at 55° C. to obtain 2-cyano-1-(1,1-diethyl-3-butenyl)ethoxybisimidazolyl phosphine as a colorless transparent oil. This was dissolved in 4.1 ml of a mixed solution of chloroform-d and chloroform, and the solution (0.5 M) was added at –3.5° C. under an argon atmosphere to 1.414 g (2.15 mmol) of N$^6$-benzoyl-5'-O-(4, 4'-dimethoxytrityl)-2'- deoxyadenosine that had been subjected to azeotropic dehydration with 5 ml of 1,4-dioxane at room temperature for one hour. Upon reaching homogeneity, the mixture was allowed to stand overnight at 4° C. for reaction to obtain the target nucleotide derivative. The $^{31}$P NMR {external standard: (CH$_3$O)$_3$P=140 ppm, CDCl$_3$} was δ; 129.5, 130.3, 131.1, 134.3 ppm (measuring the $^{31}$P NMR spectrum with a 161.7 MHz NMR measuring apparatus).

Synthesis of nucleotide represented by the formula (5-17) below wherein m=n=0, $R^{2'}$=hydrogen atom, $R^{3'}$=1,1-diethyl-3-butenyl group, $R^1$=4,4'-dimethoxytrityl group, $B^1=B^4$=9-(N-6-benzoyladeninyl) group and $A^1=A^4$=hydrogen atom in the formula (III).

promoting the side reaction represented by the formula (5-18) below and producing the by-product compound represented by the formula (5-19) below.

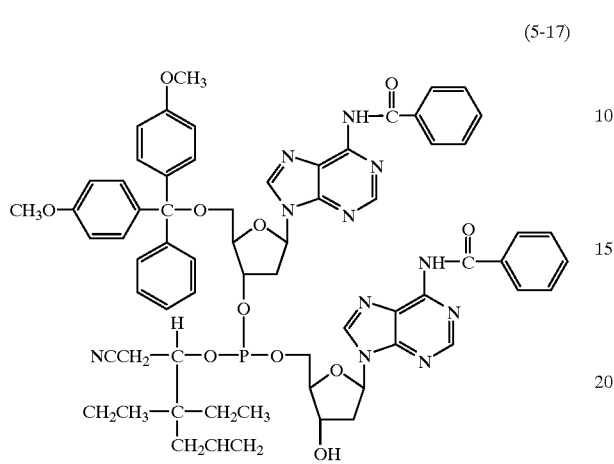

(5-17)

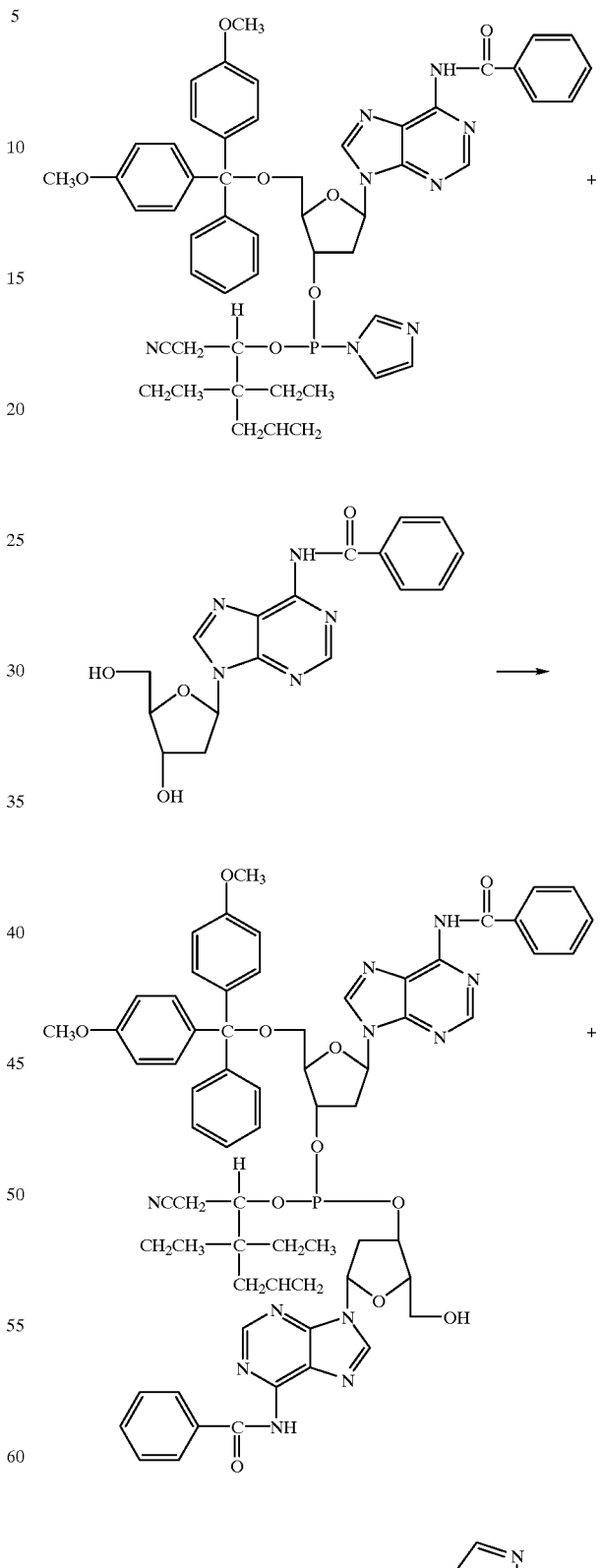

After dissolving 0.841 g (2.37 mol) of $N^6$-benzoyl-2'-deoxyadenosine with m=0, $B^4$=9-(N-$^6$-benzoyladeninyl) group and $A^4$ =hydrogen atom in the formula (II) above in 9 ml of pyridine, the mixture was subjected to azeotropic dehydration at room temperature for 1.2 hours. After repeating this procedure twice, the mixed solution of chloroform-d and chloroform containing the nucleotide derivative synthesized in a) above was added at −42° C. under an argon atmosphere to a solution of $N^6$-benzoyl-2'-deoxyadenosine in 9.6 ml of pyridine. After slowly returning the reaction solution to 4° C., it was reacted at 4° C. overnight to obtain the target nucleotide diner block precursor. The $^{31}$P NMR {external standard: $(CH_3O)_3P$=140 ppm, $CDCl_3$:py=1:2.3 (volume ratio)} was δ; 140.0, 141.1,.141.3, 141.7 ppm (measuring the $^{31}$P NMR spectrum with a 161.7 MHz NMR measuring apparatus).

c)-Production of nucleotide dimer block represented by the formula (5-15).

To the reaction solution of the nucleotide dimer block precursor synthesized in b) above there was added 0.099 g (3.09 mmol) of elemental sulfur, and the mixture was stirred for reaction under an argon atmosphere at room temperature. The $^{31}$P NMR spectrum of the reaction system was measured, and upon confirming completion of the reaction, separatory extraction was performed with chloroform and the organic layer was washed with a saturated sodium bicarbonate aqueous solution and dried over anhydrous sodium sulfate. After filtering off the sodium sulfate, the filtrate was condensed under reduced pressure to obtain a residue which was isolated and purified by silica gel column chromatography {eluent:chloroform:methanol= 100:1→100:5 (volume ratio)}. The isolation yield was 88%. The $^{31}$P NMR {external standard:$(CH_3O)_3$P140 ppm, $CDCl_3$:py=1:2.3 (volume ratio)} was δ; n65.2, 65.5, 65.8, 65.9 ppm (measuring the $^{31}$P NMR spectrum with a 161.7 MHz NMR measuring apparatus). Rf 0.48 {silica gel plate, chloroform:methanol=7:1 (volume ratio)} d) Selectivity of the coupling reaction of nucleotide derivative represented by the formula (5-16) with 5'-hydroxyl of $N^6$-benzyl-2'-deoxyadenosine.

When a nucleotide block precursor is produced according to b) above, the 3' hydroxyl of $N^6$-benzoyl-2'-deoxyadenosine reacts with the nucleotide derivative (5-16), -continued (5-19)

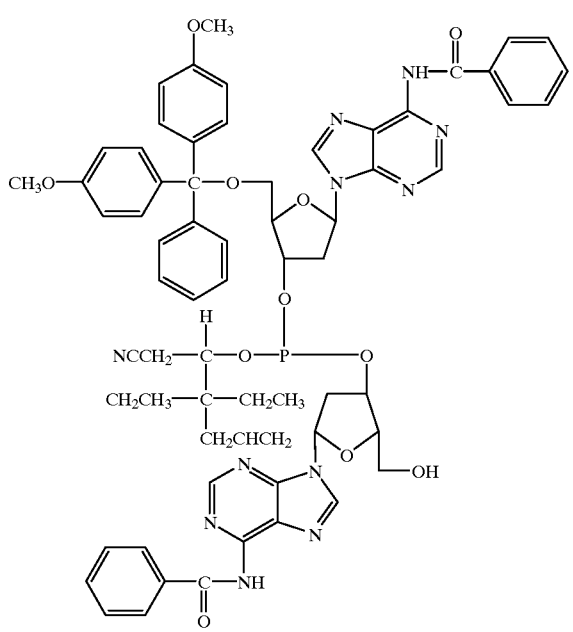

In b) above, the $^{31}$P NMR spectrum of the reaction solution was measured after completion of the reaction, and the selectivity of the coupling reaction with the 5' hydroxy group (hereunder "5' selectivity") was defined according to the following equation (E)

$$(5'\text{ selectivity})(\%) = \{(17)/((17)+(19))\} \times 100 \quad (E)$$

where (17) and (19) represent the respective molar composition ratios of compounds (5-17) and (5-19) in the reaction solution as determined by the $^{31}$P NMR spectra. The resulting 5' reactivity was 94%.

Examples 5-2 to 5-19

Nucleotide dimer blocks for Examples 5-2 to 5-19 listed in Tables 5-1 and 5-2 and their precursor nucleotides were synthesized by the same procedure as Example 5-1.

Y in the formula (5-7) was an imidazolyl group.

The nucleotide dimer blocks for Examples 5-2 to 5-19 were compounds represented by the formula (5-20) below wherein m=n=0, $A^1$ and $A^4$ are hydrogen atoms, X' is a sulfur atom and $R^1$ is a 4,4'-dimethoxytrityl group in the formula (IV), and the corresponding nucleotides are compounds represented by the formula (5-21) wherein m=n=0, $A^1$ and $A^4$ are hydrogen atoms, and $R^1$ is a 4,4'-dimethoxytrityl group in the formula (III) The structures of $R^{2'}$ and $R^{3'}$ in Tables 5-1 and 5-2 are as shown in Table 5-3. The values in parentheses in columns $B^1$ and $B^4$ of Tables 5-1 and 5-2 represent the reaction equivalent ratios with respect to the charged organooxydichlorophosphine (5-I) for the nucleosides in the same column, while in the dimerization reaction solvent column, $CDCl_3$+Py represents a mixed solvent of chloroform-d:pyridine=1:2.3 (volume ratio), $CHCl_3$+Py represents a mixed solvent of chloroform:pyridine=1:2.3 (volume ratio), Py-$d_5$+Py represents a mixed solvent of pyridine-$d_5$ and pyridine, and $CD_3CN+CH_3CN$ represents a mixed solvent of acetonitrile-$d_5$ and acetonitrile. The values in the $^{31}$P NMR δ value (ppm) for compound (III) column are the values measured in a $CDCl_3$ solution for Examples 5-1 to 5-6, 5-9 to 5-11 and 5-13 to 5-14, in a Pyridine-$d_5$ solution for Example 5-7, and in a $CD_3CN$ solution for Example 5-8. The values in the $^{31}$P NMR δ value (ppm) for compound (IV) column are the values measured in the dimerization reaction solvent solution for Examples 5-1 to 5-4 and Examples 5-11 to 5-14, and after removing the dimerization reaction solvent under reduced pressure and dissolving the residue in $CDCl_3$ for Examples 5-15 to 5-19. The Rf values for compound (IV) are all values obtained upon development with a mixed solvent of chloroform:methanol=7:1 (volume ratio) on a silica gel plate.

TABLE 5-1

Data for nucleotide dimer blocks

| No. | $R^{2'}$ | $R^{3'}$ | tuent volume ($R^{2'}$ + $R^{3'}$) (Å$^3$) | $B^1$ | $B^4$ | Dimerization reaction solvent | $^{31}$P NMR δ value for compound (III) (ppm) | $^{31}$P NMR δ value for compound (IV) (ppm) | 5' select-ivity (%) | Isolation yield for compound (IV) (%) | Rf value for compound (IV) |
|---|---|---|---|---|---|---|---|---|---|---|---|
| Example 5-1 | H | C($C_2H_5$)$_2$—CH$_2$CHCH$_2$ | 114.39 | $A^{Bz}$ (1.05) | $A^{Bz}$ (1.15) | $CDCl_3$ + Py | 140.0, 141.1, 141.3, 141.7 | 65.2, 65.5, 65.8, 65.9 | 94 | 88 | 0.48 |
| Example 5-2 | H | C($C_2H_5$)$_2$—CH$_2$CHCH$_2$ | 114.39 | T (1.03) | T (1.1) | $CDCl_3$ + Py | 140.6, 140.7, 141.0, 141.8 | 65.3, 65.4, 66.2, 66.4 | >91 | | 0.46 |
| Example 5-3 | H | C($C_2H_5$)$_2$—CH$_2$CHCH$_2$ | 114.39 | $C^{Bz}$ (1.03) | $C^{Bz}$ (1.1) | $CDCl_3$ + Py | 140.8, 141.0, 141.7 | 65.6, 66.1, 66.2 | 92 | | 0.50 |
| Example 5-4 | H | C($C_2H_5$)$_2$—CH$_2$CHCH$_2$ | 114.39 | $G^{iBu}$ (1.03) | $G^{iBU}$ (1.1) | $CDCl_3$ + Py | 140.7, 141.3, 142.0, 142.8 | 64.9, 65.7, 66.1, 66.3 | 96 | | 0.43, 0.27 |
| Example 5-5 | H | C($C_2H_5$)$_2$—CH$_2$CHCH$_2$ | 114.39 | $A^{Bz}$ (1.03) | $A^{Bz}$ (1.0) | $CDCl_3$ + Py | 139.9, 141.3, 141.4, 141.6 | | 93 | | |
| Example 5-6 | H | C($C_2H_5$)$_2$—CH$_2$CHCH$_2$ | 114.39 | T (1.03) | $T^{Bz}$ (1.0) | $CDCl_3$ + Py | 141.3, 142.1, 142.4(br) | | 87 | | |
| Example 5-7 | H | C($C_2H_5$)$_2$—CH$_2$CHCH$_2$ | 114.39 | T (1.03) | $T^{Bz}$ (1.0) | Py-d5 + Py | 142.4, 143.0(br) 143.3, 143.4(br) | | 88 | | |
| Example 5-8 | H | C($C_2H_5$)$_2$—CH$_2$CHCH$_2$ | 114.39 | T (1.05) | $T^{Bz}$ (1.0) | $CD_3CN$ + $CH_3CN$ | 142.3, 143.1, 143.3, 144.0 | | >82 | | |
| Example 5-9 | H | C($C_2H_5$)$_2$—CH$_2$CHCH$_2$ | 114.39 | T (1.03) | $T^{Bz}$ (1.0) | $CDCl_3$ + $CHCl_3$ | 142.3, 142.5, 142.8 | | >77 | | |

TABLE 5-2

Data for nucleotide dimer blocks

| No. | $R^{2'}$ | $R^{3'}$ | Substituent volume ($R^{2'} + R^{3'}$) (Å³) | $B^1$ | $B^4$ | Dimerization reaction solvent | $^{31}$P NMR δ value for compound (III) (ppm) | $^{31}$P NMR δ value for compound (IV) (ppm) | 5' selectivity (%) | Isolation yield for compound (IV) (%) | Rf value for compound (IV) |
|---|---|---|---|---|---|---|---|---|---|---|---|
| Example 5-10 | H | t-C₄H₉ | 64.27 | T (1.03) | T$^{Bz}$ (1.0) | CDCl₃ + Py | 141.0, 141.3, 141.6(br), 141.7(br) | | >79 | | |
| Example 5-11 | H | i-C₃H₇ | 49.88 | T (1.03) | T (1.5) | CDCl₃ + Py | 138.7, 139.0, 139.3 | 64.7, 64.8, 65.2 | >84 | 77 | 0.45 |
| Example 5-12 | H | t-C₄H₉ | 64.27 | T (1.03) | T (2.0) | CDCl₃ + Py | | 66.2, 66.3, 66.6, 66.9 | 88 | 84 | 0.45 |
| Example 5-13 | H | t-C₄H₉ | 64.27 | C$^{Bz}$ (1.03) | C$^{Bz}$ (2.0) | CDCl₃ + Py | 140.6, 140.9, 141.1, 141.2 | 65.7, 65.8, 65.9 | 85 | | 0.51 |
| Example 5-14 | CH₃ | i-C₄H₉ | 78.29 | C$^{Bz}$ (1.04) | C$^{Bz}$ (1.1) | CHCl₃ + Py | 133.6, 133.7, 134.0, 134.2 | 55.9, 56.2, 56.4 | 88 | | 0.51 |
| Example 5-15 | H | t-C₄H₉ | 64.27 | T (1.02) | G$^{iBu}$ (1.1) | CHCl₃ + Py | | 65.6, 66.1, 66.2 | 97 | 90 | 0.42 |
| Example 5-16 | H | t-C₄H₉ | 64.27 | A$^{Bz}$ (1.03) | G$^{iBu}$ (1.2) | CHCl₃+ Py | | 65.4, 65.9, 66.0, 66.2 | 96 | 80 | 0.38 |
| Example 5-17 | H | t-C₄H₉ | 64.27 | T (1.03) | A$^{Bz}$ (1.2) | CHCl₃ + Py | | 65.7, 66.0, 66.3, 66.5 | 87–92 | | 0.47 |
| Example 5-18 | H | t-C₄H₉ | 64.27 | A$^{Bz}$ (1.03) | T (1.2) | CHCl₃ + Py | | 65.8, 66.3, 66.6 | 81–87 | 74 | 0.48 |
| Example 5-19 | H | t-C₄H₉ | 64.27 | T (1.03) | C$^{An}$ (1.2) | CHCl₃ + Py | | 65.8, 66.0, 66.2, 66.5 | 86 | | 0.49 |
| Example 6-1 | H | C(C₂H₅)₂—CH₂CHCH₂ | 114.39 | C$^{mPEG}$ (1.0) | A$^{Bz}$ (1.0) | CHCl₃ + Py | | 65.6, 66.0, 66.3 | | 88 | |

(In Tables 5-1 and 5-2, T in columns $B^1$ and $B^4$ represents a 1-thyminyl group, $T^{Bz}$ represents a 1-(N-3-benzoylthyminyl) group, $C^{Bz}$ represents a 1-(N-4-benzoylcytosinyl) group, $C^{An}$ represents a 1-(N-4-anisoylcytosinyl) group, $A^{Bz}$ represents a 9-(N-6-benzoyladeninyl) group, $A^{Bz2}$ represents a 9-(N-6, N-6-bisbenzoyladeninyl) group, $G^{iBu}$ represents a 9-(N-2-isobutyrylguaninyl) group.), and $C^{mPEG}$ represents 1-cytosinyl group N-protected with a functional group having a methoxypolyethylene glycol chain.)

TABLE 5-3

The abbreviations in the columns for substituent $R^{3'}$ in Tables 5-1 and 5-2 represent the following structures.

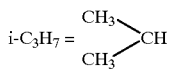
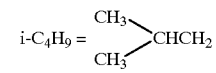

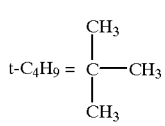
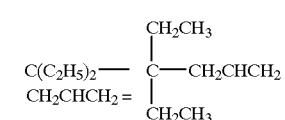

(5-20)

TABLE 5-3-continued

The abbreviations in the columns for substituent $R^{3'}$ in Tables 5-1 and 5-2 represent the following structures.

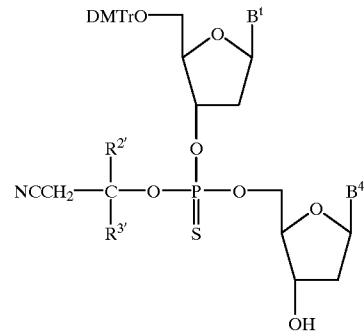

wherein DMTr represents a 4,4'-dimethoxytrityl group and $B^1$, $B^4$, $R^{2'}$ and $R^{3'}$ are the same as in the formula (IV) above.

(5-21)

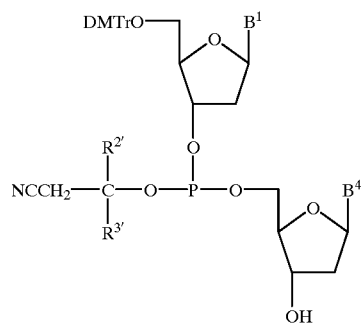

wherein DMTr is the same as in the formula (5-20) above, and $B^1$, $B^4$, $R^{2'}$ and $R^{3'}$ are the same as in the formula (IV) above.

Example 5-20

Synthesis of nucleotide trimer block represented by the formula (5-22) below wherein m=0, n=1, $R^2=R^{2'}$=hydrogen atom, $R^3$=tert-butyl group, $R^{3'}$=1,1-diethyl-3-butenyl group, $R^1$=4,4'-dimethoxytrityl group, $B^1=B^2=B^4$=1-thyminyl group, $A^1=A^2A^4$=hydrogen atom and X=X'=sulfur atom in the formula (IV).

(5-22)

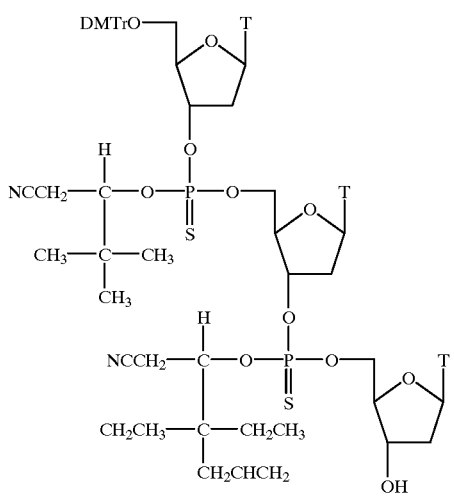

where T represents a 1-thyminyl group and DMTr is the same as in the formula (5-20).

a) Synthesis of nucleotide precursor represented by the formula (I-4).

Synthesis was carried out in the same manner as Example 5-1, except that before the reaction, the procedure of dissolving 1.2 equivalents of the nucleotide diner block represented by (5-IV) of the formula (5-14) above with respect to the charged organooxydichlorophosphine (5-I) into 1,4-dioxane and azeotropic dehydration was repeated twice, and the concentration of the reaction solution was adjusted to 0.3 M. Y in the formula (5-7) was an imidazolyl group, and the nucleotide derivative represented by the formula (5-23) was synthesized.

The $^{31}$P NMR (external standard: $(CH_3O)_3P$=140 ppm, $CDCl_3$) was δ; 126.8, 127.4, 128.1, 128.9, 129.2, 129.5, 129.8, 131.6, 132.2, 132.6, 132.9, 133.7 ppm (The $^{31}$P NMR spectrum was measured with a 161.7 MHz NMR measuring apparatus. The δ values were for the 3'-terminal trivalent phosphorus atom.)

(5-23)

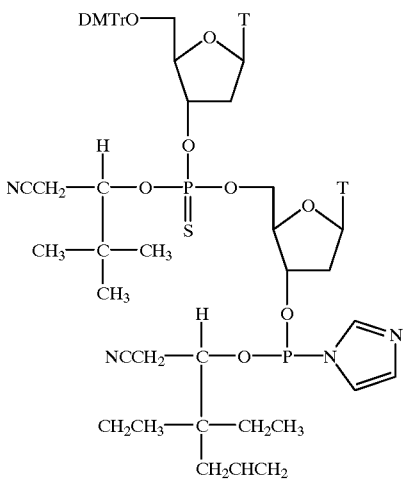

where T is the same as in the formula (5-22) and DMTr is the same as in the formula (5-20).

b) Synthesis of nucleotide represented by the formula (III).

The nucleotide trimer block precursor represented by the formula (5-24) was synthesized in the same manner as Example 5-1, except that 1.2 equivalents of the 3'-O- and 5'-O-unprotected nucleoside derivative represented by the formula (II) (thymidine in this example) was reacted with respect to the charged organooxydichlorophosphine (5-I), and the reaction concentration was adjusted to 0.1 M or lower (chloroform-d:pyridine 1:2 or greater (volume ratio)).

The 5' selectivity for the condensation reaction was >94%.

(5-24)

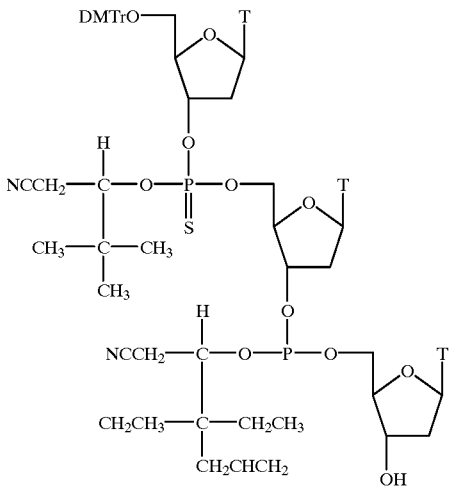

where T is the same as in the formula (5-22) and DMTr is the same as in the formula (5-20).

c) Synthesis of nucleotide trimer block represented by the formula (5-22).

The synthesis was carried out in the same manner as Example 5-1.

$^{31}$P NMR {external standard: $(CH_3O)_3P$=140 ppm, $CDCl_3$}: Measurement was made with 9 peaks in the range of 65.7–66.7 ppm (measuring the $^{31}$P NMR spectrum with a 161.7 MHz NMR measuring apparatus).

The Rf value was 0.43 {silica gel plate, developing solvent: chloroform:methanol=7:1 (volume ratio)}

Example 5-21

Synthesis of nucleotide trimer block represented by the formula (5-25) below wherein m=0, n=1, $R^2$=$R^{2'}$=hydrogen atom, $R^3$=1,1-diethyl-3-butenyl group, $R^{3'}$=tert-butyl group, $R^1$=4,4'-dimethoxytrityl group, $B^1$=$B^2$=$B^4$=1-thyminyl group, $A^1$=$A^2$=$A^4$=hydrogen atom and X=X'=sulfur atom in the formula (IV).

(5-25)

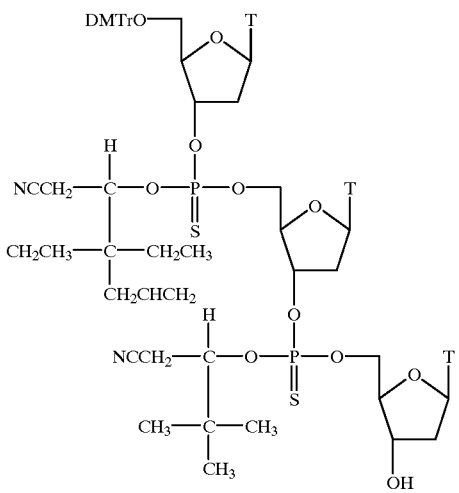

where T is the same as in the formula (5-22) and DMTr is the same as in the formula (5-20).

Production was carried out in the same manner as Example 5-1, except that 1.03 equivalents of the 5'-O- and base-protected nucleotide derivative represented by (5-IV) of the formula (5-14) above and 1.2 equivalents of the 3'-O- and 5'-O unprotected nucleotide derivative represented by the formula (II) above were each reacted with the charged organooxydichlorophosphine (5-I). Y in the formula (5-8) was an imidazolyl group.

a) Synthesis of nucleotide trimer block precursor represented by the formula (5-26) below.

$^{31}$P NMR {external standard: $(CH_3O)_3P$=140 ppm, $CDCl_3$:py=1:2.3 (volume ratio)}: Measurement was made with 13 peaks in the range of δ: 140.3–142.2 ppm (measuring the $^{31}$P NMR spectrum with a 161.7 MHz NMR measuring apparatus. The δ values were for the trivalent phosphorus atom (phosphite) on the 3'-terminal side of the two internucleotide bonds.)

(5-26)

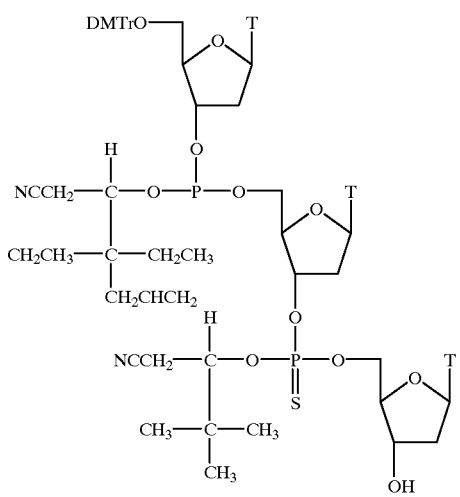

where T is the same as in the formula (5-22) and DMTr is the same as in the formula (5-20).

b) Synthesis of nucleotide trimer block represented by the formula (5-25). $^{31}$P NMR {external standard: $(CH_3O)_3P$= 140 ppm, $CDCl_3$:py=1:2.3 (volume ratio)}: Measurement was made with 13 peaks in the range of δ: 65.0–66.3 ppm (measuring the $^{31}$P NMR spectrum with a 161.7 MHz NMR measuring apparatus).

The Rf value was 0.44 {silica gel plate, developing solvent: chloroform:methanol=7:1 (volume ratio)} c) HPLC analysis of phosphorothioate-type nucleotide trimer represented by the formula (5-27) below obtained by removing phosphoric acid protecting groups of nucleotide trimer block represented by the formula (5-25) synthesized according to b) above.

(5-27)

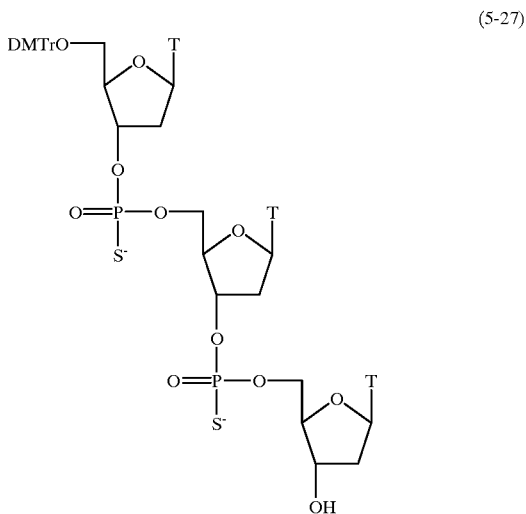

where T is the same as in the formula (5-22) and DMTr is the same as in the formula (5-20).

After dissolving approximately 1 mg of the nucleotide trimer block represented by the formula (5-25) in a few drops of pyridine, a few drops of concentrated ammonium hydroxide were added and the mixture was allowed to stand overnight at room temperature to remove the phosphoric acid protecting groups to obtain the phosphorothioate-type nucleotide trimer represented by the formula (5-27). The residue obtained by removing the ammonia and solvent under reduced pressure was dissolved in a 0.1 N-pH 7.2 triethylamine-acetic acid buffer. solution and subjected to HPLC analysis.

The HPLC analysis was carried out using a 4.6 mm$\phi$×150 mm Wakopak ws-DNA column (Wako Junyaku, KK.) as the reverse phase column (ODS column) and 0.1 N-pH 7.2 triethylamine-acetic acid buffer solution and acetonitrile as the eluent. The gradient used for the analysis was acetonitrile/buffer solution=5/95→45/55 (20 min), the detection wavelength of the UV detector used for analysis was 260 nm, and the analysis temperature was 40° C.

The retention times ($t_R$) for the obtained compounds were 21.6 (splitting of the tip into two) and 22.1 minutes (splitting into a total of three due to inclusion of diastereomers). The HPLC analysis results matched those for the phosphorothioate-type nucleotide trimer represented by the formula (5-27) which was synthesized according to the usual phosphoramidite method.

Example 5-22

Synthesis of tetrathymidine nucleotide represented by the following formula (5-28) below wherein n=m=1, $R^2=R^{2'}=R^{2''}$=hydrogen atom, $R^3=R^{3'}=R^{3''}$=tert-butyl group, $R^1$=4,4'-dimethoxytrityl group, $B^1=B^2=B^3=B^4$=1-thyminyl group, $A^1=A^2=A^3=A^4$=hydrogen atom and X=X'=X=sulfur atom in the formula (IV).

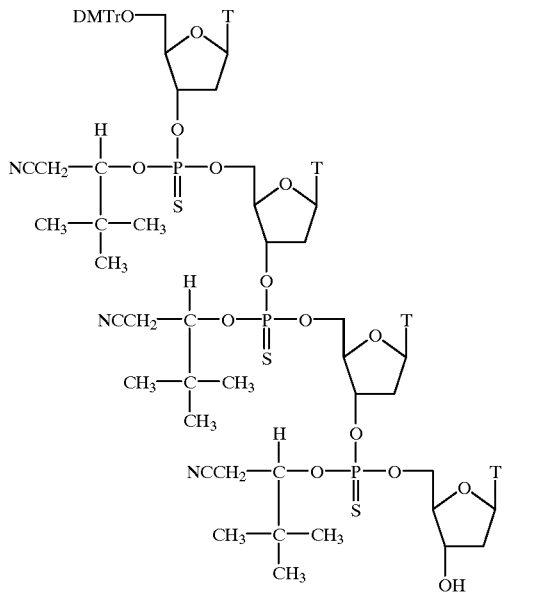

(5-28)

A chloroform solution (0.7 ml) containing a phosphorylating agent ((5-III): $R^{2'}$=hydrogen atom, $R^{3'}$=tert-butyl group, Y=imidazolyl group) (0.33 mmol) synthesized by the same method as described in Example 5-1 was added to the 5.'-O-protected thymidine dinucleotide ((IV): n=m=0, $R^{2'}$=hydrogen atom, $R^{3'}$=tert-butyl group, $R^1$=4,4'-dimethoxytrityl group, $B^1=B^4$=1-thyminyl group, $A^1=A^4$=hydrogen atom, X'=sulfur atom) (0.29 g, 0.3 mmol) synthe-sized in Example 5-12 while cooling on ice, and reaction was conducted at room temperature for one hour. The solution was then added to a pyridine solution (1.5 ml) containing dithymidine nucleotide ((II): m-1, $R^{2''}$=hydrogen atom, $R^{3''}$=tert-butyl group, $B^3=B^4$=1-thyminyl group, $A^3=A^4$=hydrogen atom, X''=sulfur atom) (0.22 g, 0.33 mmol) and benzotriazole (0.07 g, 0.6 mmol) while cooling on ice. The reaction temperature was slowly returned to room temperature, and after reaction for one hour at that temperature, elemental sulfur (0.02 g, 0.6 mmol) was added and the reaction mixture was stirred for one hour at room temperature. The reaction product was washed with a 5% sodium bicarbonate aqueous solution and with saturated brine, and then the solvent was removed under reduced pressure. The residue was subjected to silica gel column chromatography to obtain tetrathymidine nucleotide (yield: 0.48 g, 87%; Rf 0.38 (chloroform/methanol=10/1)).

Example 5-23

Synthesis of hexathymidine nucleotide represented by the following formula (5-29) below wherein n=3, m=1, $R^2=R^{2'}=R^{2''}$=hydrogen atom, $R^3=R^{3'}R^{3''}$=tert-butyl group, $R^1$=4,4'-dimethoxytrityl group $B^1=B^2=B^3=B^4$=-thyminyl group, $A^1=A^2=A^3=A^4$=hydrogen atom and X=X'=X''=sulfur atom in the formula (IV).

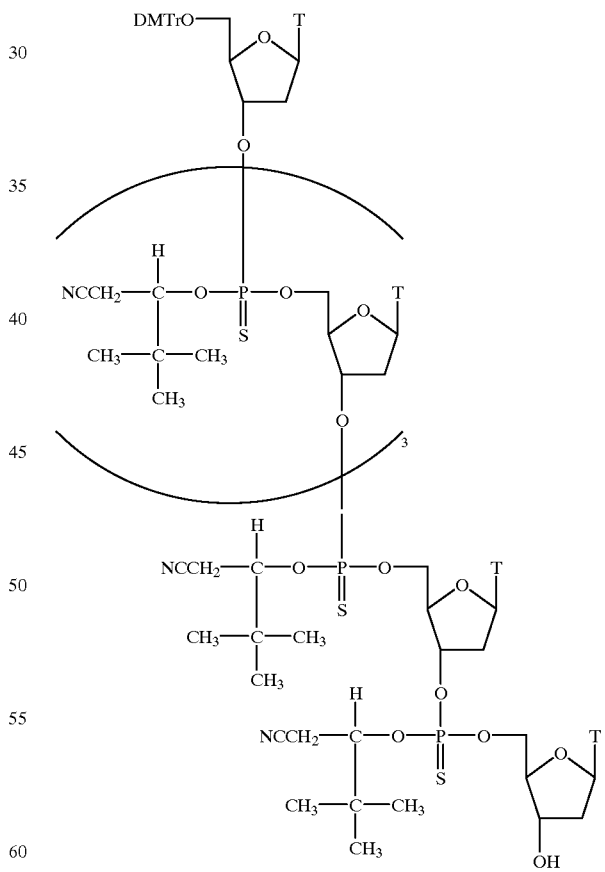

(5-29)

A phosphorylating agent ((5-III): $R^{2'}$=hydrogen atom, $R^{3'}$=tert-butyl group, Y=imidazolyl group) (0.28 mmol) synthesized by the same method as described in Example 5-1 and the 5'-O-protected tetrathymidine nucleotide ((IV): n=m=1, $R^2=R^{2'}=R^{2''}$=hydrogen atom, $R^3R^{3'}=R^{3''}$=tert-butyl group, $R^1$=4,4'-dimethoxytrityl group, $B^1=B^2=B^3=B^4$=1-thyminyl group, $A^1=A^2=A^3=A^4$=hydrogen atom, X=X'=X''=sulfur atom) (0.46 g, 0.25 mmol) synthesized in Example 5-22 were reacted in chloroform (0.6 ml) in the same manner as Example 5-22. The solution was then added to a pyridine solution (1.3 ml) containing dithymidine nucleotide ((II): m=1, $R^{2''}$=hydrogen atom, $R^{3''}$=tert-butyl group, $B^3=B^4$=1-thyminyl group, $A^3=A^4$=hydrogen atom, X''=sulfur atom) (0.19 g, 0.28 mmol) and benzotriazole (0.067 g, 0.56 mmol) while cooling on ice, for reaction in the same manner as Example 5-22. Elemental sulfur (0.018 g, 0.56 mmol) was then added and the reaction was carried out in the same manner as Example 5-22, after which the same after-treatment as in Example 5-22 was performed to obtain hexathymidine nucleotide (yield: 0.57 g, 85%; Rf 0.35 (chloroform/methanol=10/1)).

Example 5-24

Production of heptathymidine nucleotide represented by the following formula (5-30) below wherein $R^1$=succinyl group ester bonded with the hydroxy group of the polyethyleneglycol methyl ether (mPEG) residue at one side in the formula (IV) above.

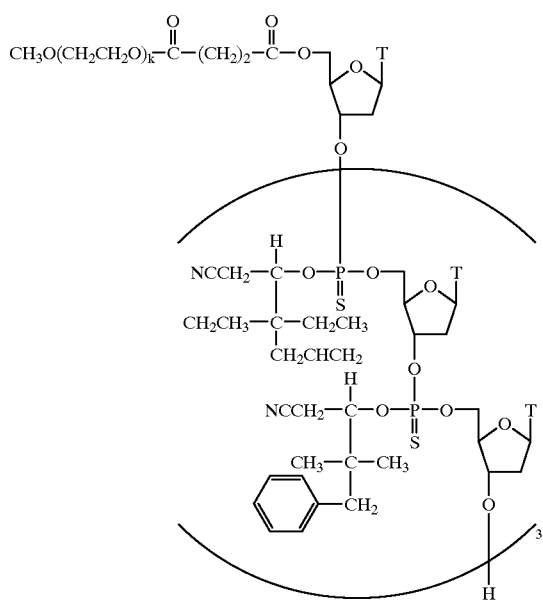

(5-30)

A chloroform solution (0.5 ml) containing a phosphorylating agent ((5-III): $R^2$ hydrogen atom, $R^{3'}$=1,1-diethyl-3-butenyl group, Y=imidazoyl group) (0.22 mmol) synthesized by the same method as described in Example 5-1 was added to thymidine (0.46 g, 0.2 mmol) protected at the 5' end with a succinyl group ester bonded with the hydroxyl group of the mPEG (Mn=2000) at one side, while cooling on ice, and reaction was conducted at room temperature for one hour. To this solution there was then added a pyridine solution (1.2 ml) containing dithymidine nucleotide ((II): m1, $R^{2''}$=hydrogen atom, $R^{3'}$=1,1-dimethyl-2-phenylethyl group, $B^3=B^4$=1-thyminyl group, $A^3=A^4$=hydrogen atom, X''=sulfur atom) (0.16 g, 0.22 mmol) and benzotriazole (0.04 g, 0.3 mmol) while cooling on ice. After reaction at room temperature for one hour, triethylsilylimidazole (0.009 g, 0.05 mmol) was added, and reaction was conducted at room temperature for 30 minutes. To this reaction mixture there was then added a mixed solvent (20 ml) of diethylether/2-propanol (4/1), the mixture was cooled on ice, and the supernatant liquid was discarded. To the residue there was added diethylether (20 ml), and the mixture was cooled on ice. The supernatant liquid was discarded, and the residue was dried under reduced pressure.

To this after addition of a chloroform solution containing a phosphorylating agent ((5-III): $R^{2'}$=hydrogen atom, $R^{3'}$= 1,1-diethyl-3-butenyl group, Y=imidazolyl group) (0.22 mmol), a pyridine solution (1.0 ml) containing dithymidine nucleotide ((II): m=1, $R^{2''}$=hydrogen atom, $R^{3''}$=1,1-dimethyl-2-phenylethyl group, $B^3=B^4$=1-thyminyl group, $A^3=A^4$=hydrogen atom, X''=sulfur atom) (0.16 g, 0.22 mmol) and benzotriazole (0.04 g, 0.3 mmol) was added, and the same reaction as above was carried out. This was followed by addition of triethylsilylimidazole (0.009g, 0.05mmol) for reaction in the same manner as above. The reaction product was washed with a mixed solvent (20 ml) of diethylether/2-propanol (4/1) and diethylether in the same manner as above, and the residue was dried under reduced pressure.

To this after addition of a chloroform solution containing a phosphorylating agent ((5-III): $R^{2'}$=hydrogen atom, $R^{3'}$= 1,1-diethyl-3-butenyl group, Y=imidazolyl group) (0.22 mmol), a pyridine solution (1.0 ml) containing dithymidine nucleotide ((II): m=1, $R^{2''}$=hydrogen atom, $R^{3''}$=1,1-dimethyl-2-phenylethyl group, $B^3=B^4$=1-thyminyl group, $A^3=A^4$=hydrogen atom, X''=sulfur atom) (0.16 g, 0.22 mmol) and benzotriazole (0.04 g, 0.3 mmol) was added, and the same reaction as above was carried out. This was followed by addition of triethylsilylimidazole (0.009 g, 0.05 mmol) for reaction in the same manner as above. The reaction product was washed with a mixed solvent (20 ml) of diethylether/2-propanol (4/1) and diethylether in the same manner as above, and the residue was dried under reduced pressure.

This residue was dissolved in a mixed solvent (2 ml) of chloroform/pyridine (1/2). After adding imidazole (0.14 g, 2 mmol) and elemental sulfur (0.06 g, 1.9 mmol) thereto, reaction was conducted at room temperature for 5 hours. The reaction mixture was washed with 5% sodium bicarbonate and saturated brine, and then the solvent was removed under reduced pressure. The residue was subjected to silica gel column chromatography to obtain the target heptathymidine nucleotide with a mPEG residue at the 5' end (yield: 0.87 g, 81%; Rf 0.35(chloroform/methanol=10/1)).

This heptathymidine nucleotide with a mPEG residue at the 5' end was treated with a mixed solution of pyridine/28% ammonia solution (1/1) at 60° C. for 2 hours. The results of HPLC analysis and the retention time for the product matched those of a heptathymidine nucleotide synthesized by the phosphoramidite method.

Example 5-25

Production of nucleotide derivative represented by the following formula (5-31), wherein n=1, $R^2=R^{2'}$=2 hydrogen atom, $R^3=R^{3'}$=tert-butyl group, $R^1$=4,4'-dimethoxytrityl group, $B^1=B^2$=1-thyminyl group, $A^1=A^2$=hydrogen atom, Y=triazolyl group and X=sulfur atom in the formula (I-4) above.

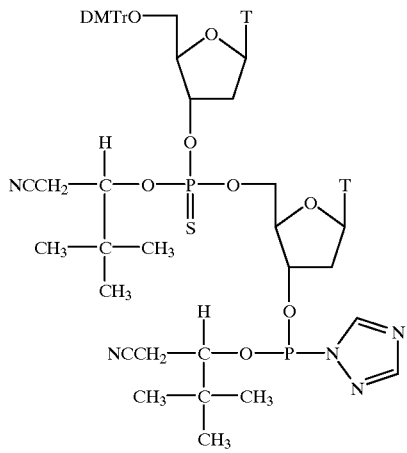

(5-31)

2-cyano-1-(tert-butyl)ethoxy dichlorophosphine 0.091 g (0.399 mmol) and 1-(trimetylsilyl)-1,2,4-triazole 0.124 g (0.878 mmol) were reacted by the same manner as Example 5-1 to obtain 2-cyano-1-(tert-butyl)ethoxy bistriazolylphosphine. This was added to 5'-O-protected dithymidine nucleotide ((IV): m=n=0, $R^{2'}$=hydrogen atom, $R^{3'}$=tert-butyl group, $R^1$=4,4'-dimethoxytrityl group, $B^1$=$B^4$=1-thyminyl group, $A^1$=$A^4$ =hydrogen atom, X'=sulfur atom) 0.393 g (0.403 mmol), which was synthesized by the same procedure in Example 5-2, at −60° C., and the target nucleotide derivative was synthesized in the same manner as Example 5-20.

The monosubstitution selectivity for the phosphorylation reaction was 91%.

$^{31}$P NMR {external standard; $(CH_3O)_3P$=140 ppm, $CDCl_3$} was δ; 120.6, 121.7, 122.0, 123.9, 124.7, 125.1, 125.2, 126.3, 126.4, 126.5, 126.7, 126.8, 127.5 ppm. (The $^{31}$P NMR spectrum was measured with a 161.7 MHz NMR measuring apparatus. The δ values were for the 3'-terminal trivalent phosphorus atom.)

Example 5-26

Production of tritymidine nucleotide derivative represented by the following formula (5-32), wherein n=1, m=0, $R^2$=$R^{2'}$=hydrogen atom, $R^3$=$R^{3'}$=tert-butyl group. $R^1$=4,4'-dimethoxytrityl group, $B^1$=$B^2$=$B^4$=1-thyminyl group, $A^1$=$A^2$=$A^4$=hydrogen atom, X=X'=oxygen atom in the formula (IV) above.

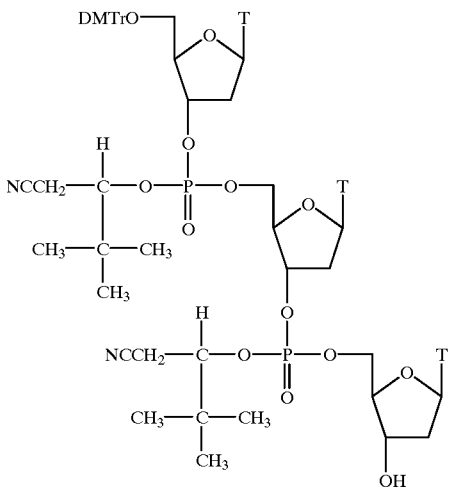

(5-32)

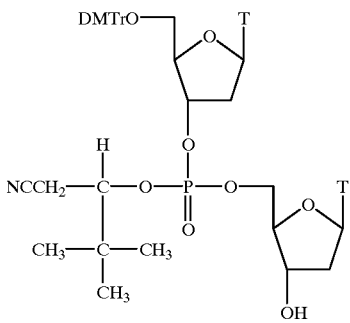

(5-33)

A chloroform solution (12ml) containing a 2-cyano-1-(tert-butyl)ethoxy bisimidazolyl phosphine (phosphorylation agent; 4.619 mmol), which was synthesized by the same manner as Example 5-1, was added to 5'-O-protected dithymidine nucleotide ((IV): m=n=0, $R^{2'}$= hydrogen atom, $R^{3'}$=tert-butyl group, $R^1$=4,4'-dimethoxytrityl group, $B^1$=$B^4$=1-thyminyl group, $A^1$=$A^4$= hydrogen atom, X'=oxygen atom) represented by the above formula (5-33), 4.425 g (4.619 mmol) while cooling on ice, and reaction was conducted at room temperature for 2 hours. This reaction mixture was added to a pyridine solution (24 ml) containing tymidine (1.343 g, 5.542 mmol) while ice cooling on ice, and reaction was conducted at room temperature for 2 hours. To this there was added iodine (1.524 g, 6.00 mmol), which was dissolved in tetrahydrofuran (15 ml) and water (1 ml), while cooling on ice, the reaction was conducted at room temperature for 20 minutes. After washing the reaction mixture with 5% sodium hydrogen-sulfite aqueous solution and saturated brine, the solvent of the organic layer was removed under reduced pressure. The residue was purified by silica gel column chromatography to obtain the target trithymidine nucleotide (5.1 g, 81% yield) represented by the formula (5-32) above.

Example 6-1

Synthesis of dinucleotide compound represented by the formula (6-1), where m=n=0, $R^1$ is 4,4'-dimethoxytrityl, $A^1$, $A^4$ and $R^{2'}$ are hydrogen atoms, $R^{3'}$ is 1,1-diethyl-3-butenyl, X' is a sulfur atom, $B^1$ is a 1-cytosinyl group N-protected with a functional group having a methoxypolyethylene glycol chain represented by the formula —C(=O)—A—(OCH$_2$CH$_2$)$_k$OCH$_3$ (number average molecular weight (Mn)=350), A is 1,4-phenylene and B$^4$ is N-benzoyladeninyl, in the formula (IV).

(6-1)

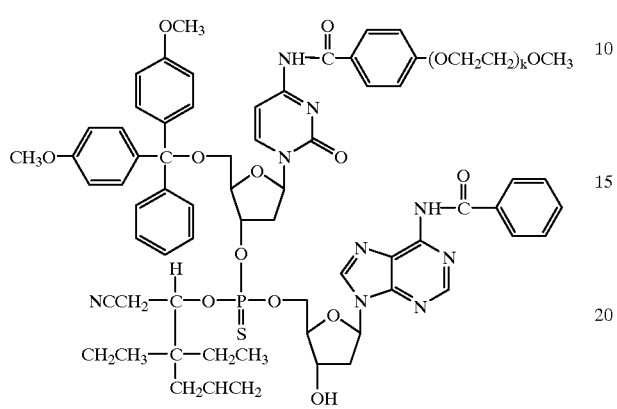

A chloroform/pyridine mixed solution (1/2 (v/v), 5 ml) containing 890 mg (2.5 mmol) of N$^6$-benzoyl-2'-deoxyadenosine was added to a solution of chloroform (5 ml) containing an approximately 2.5 mmol of the nucleotide compound (phosphorazolide compound in situ DNA synthesis reagent) represented by the formula (3-1) above that was synthesized in the same manner as Example 3-1, under an argon atmosphere at 0° C., and the mixture was allowed to stand overnight at 4° C. for reaction. After 160 mg (5 mmol) of elemental sulfur that had been already dried under reduced pressure for at least 3 hours was added to the reaction solution at room temperature, the mixture was stirred for 12 hours for reaction. The solvent was removed under reduced pressure below room temperature, and the residue was redissolved in 20 ml of chloroform and purified by 5 silica gel column chromatography (eluent: chloroform/methanol=100/3 (v/v)) to obtain 3.43 g of the target dinucleotide compound represented by the formula (6-1) (88% yield). The $^{31}$P NMR of the obtained compound (161.7 MHz, CDCl$_3$, external standard: (CH$_3$O)$_3$P=140 ppm) was δ=65.6, 66.0, 66.3 ppm. The data for the $^{31}$P NMR spectrum and isolation yield are shown in Table 5-2.

After dissolving 1.0 g of the dinucleotide compound with a methoxypolyethylene glycol chain obtained in this manner in 5 ml of chloroform, 50 ml of diethyl ether was added thereto while mixing, and a white precipitate deposited. After allowing the reaction system to stand overnight the diethyl ether was removed by decantation, and then after washing the residue three times by decantation with 5 ml of diethyl ether, it was dried under reduced pressure to obtain 0.97 g of a white solid (97% yield). The $^{31}$P NMR spectrum thereof matched that of the aforementioned dinucleotide compound. That is, the dinucleotide compound with a methoxypolyethylene glycol chain represented by the formula (6-1) was recovered at a high yield by the above-mentioned reprecipitation method.

After dissolving 1.30 g of this dinucleotide compound in 40ml of 2-propanol at 50–55° C., it was allowed to stand overnight at 4° C. to obtain 1.04 g of a white solid in the same manner as the aforementioned reprecipitation (80% yield). That is, the dinucleotide compound with a methoxypolyethylene glycol chain represented by the formula (6-1) was recovered at a high yield by the above-mentioned recrystallization method.

What is claimed is:

1. A nucleotide compound represented by the following formula (I):

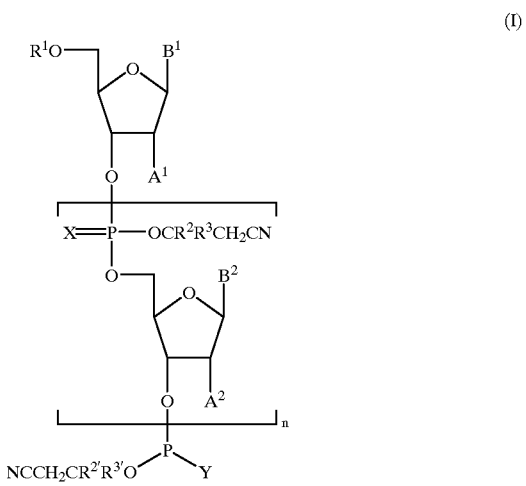

wherein R$^1$ represents a protective group or an organic group represented by the formula —C(=O)—A'—(OCH$_2$CH$_2$)$_k$OCH$^3$ in which k represents an integer of 3 or more, and A' is a divalent organic group; R$^2$, R$^{2'}$, R$^3$ and R$^{3'}$ each represents a hydrogen atom or an alkyl, cycloalkyl, aryl or aralkyl group which may contain a hetero-atom and R$^2$, R$^{2'}$, R$^3$ and R$^{3'}$ may be the same or different; B$^1$ and B$^2$ each represents a base, optionally, protected by a protective group common in nucleotide chemistry or B' which represents —B$^{1'}$—C(=O)—A—(OCH$_2$CH$_2$)$_k$OCH$_3$ in which B$^{1'}$ represents one of the groups represented by the

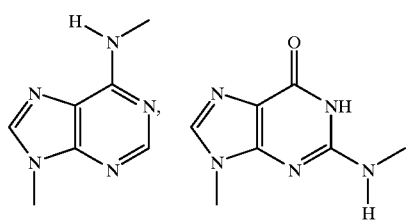

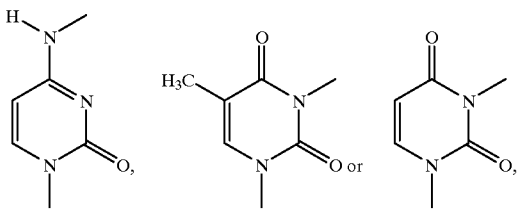

k represents an integer of 3 or more, A is a divalent group and represents an arylene group or an alkylene group having a straight or branched chain which may contain a heteroatom; X represents an oxygen atom or a sulfur atom; Y represents an azolyl group, a monoalkylamino group represented by $HNR^5$ in which $R^5$ is an alkyl group or a cycloalkyl group, a dialkylamino group or a saturated nitrogenous heterocyclic ring; $A^1$ and $A^2$ each represents a hydrogen atom, a hydroxyl group, an alkoxy group or a trialkylsilyloxy group; and n represents 0 or an integer of 1 to 100; excluding the case wherein at least one of the combinations of $R^2$ and $R^3$ and of $R^{2'}$ and $R^{3'}$ being a hydrogen atom and hydrogen atom, a hydrogen atom and a methyl group, a hydrogen atom and an ethyl group, a methyl group and a methyl group, a methyl group and an ethyl group or an ethyl group and an ethyl group.

2. A compound according to claim 1, wherein the sum of van der Waals volumes of $R^2$ and $R^3$ and sum of van der Waals volumes of $R^{2'}$ and $R^{3'}$ in formula (I) are respectively 49 cubic angstroms or larger, and Y is an imidazolyl group, a 2-methylimidazolyl group, a 4-methylimidazolyl group or a triazolyl group.

3. A compound according to claim 1, wherein said compound is represented by the following formula (I-1):

(I-1)

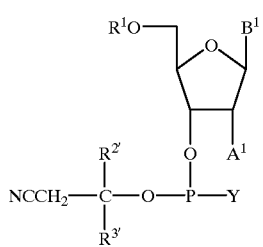

wherein $B^1$ represents a base, optionally, protected by a protective group common in nucleotide chemistry; and Y represents an azolyl group.

4. A compound according to claim 3, wherein the sum of van der Waals volumes of $R^{2'}$ and $R^{3'}$ in formula (I-1) is at least 49 cubic angstroms and Y is an imidazolyl group, a 2-methylimidazolyl group or a 4-methylimidazolyl group.

5. A compound according to claim 1, wherein said compound is represented by the following formula (I-2):

(I-2)

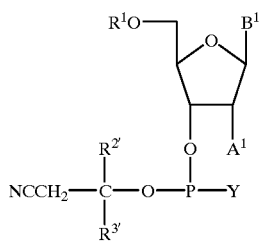

wherein $B^1$ represents a base, optionally, protected by a protective group common in nucleotide chemistry; and Y represents either a monoalkylamino group represented by $HNR^5$ in which $R^5$ represents an alkyl group or a cycloalkyl group or a dialkylamino group.

6. A monoalkylamino type phosphoramidite compound according to claim 5, wherein the sum of van der Waals volumes of $R^{2'}$ and $R^{3'}$ in formula (I-2) is at least 49 cubic angstroms.

7. A compound according to claim 1, wherein said compound is represented by the following formula (I-3):

(I-3)

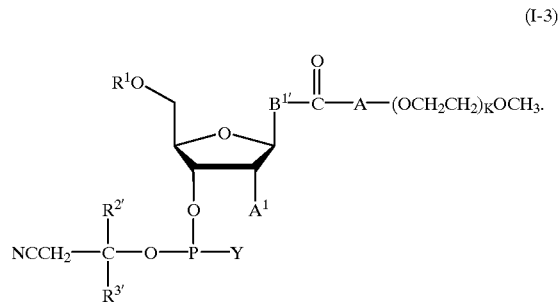

8. A compound according to claim 7, wherein the sum of Van der Waals volumes of $R^{2'}$ and $R^{3'}$ in formula (I-3) is at least 49 cubic angstroms.

9. A nucleoside compound represented by the following formula (I-3'):

(I-3')

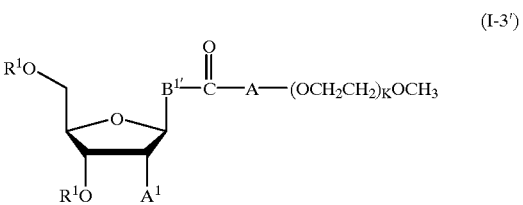

wherein $R^1$ represents a protective group or an organic group represented by the formula $-C(=O)-A'-(OCH_2CH_2)_kOCH_3$ in which k represents an integer of 3 or more, $R^4$ represents a hydrogen atom or a protective group commonly used in nucleotide chemistry, A is a divalent group and represents an arylene group or an alkylene group having a straight or branched chain which may contain a hetero-atom; $A^1$ represents a hydrogen atom, a hydroxyl group, an alkoxy group or a trialkylsilyloxy group; and $B^{1'}$ represents one of the groups represented by one of the following formula (1):

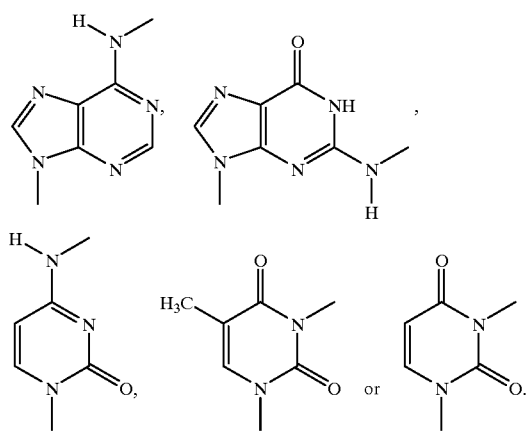

10. A method for producing a nucleotide block oligonucleotide represented by the following formula (IV) which comprises reacting a nucleotide derivative represented by formula (I-4) with a 3'-O- and 5'-O-unprotected nucleoside derivative or nucleotide derivative represented by formula (II) or reacting them in the presence of an optionally selected activating agent and oxidizing or sulfurizing a trivalent phosphorus atom of the resulting nucleotide represented by the following formula (III) to a pentavalent phosphorus atom:

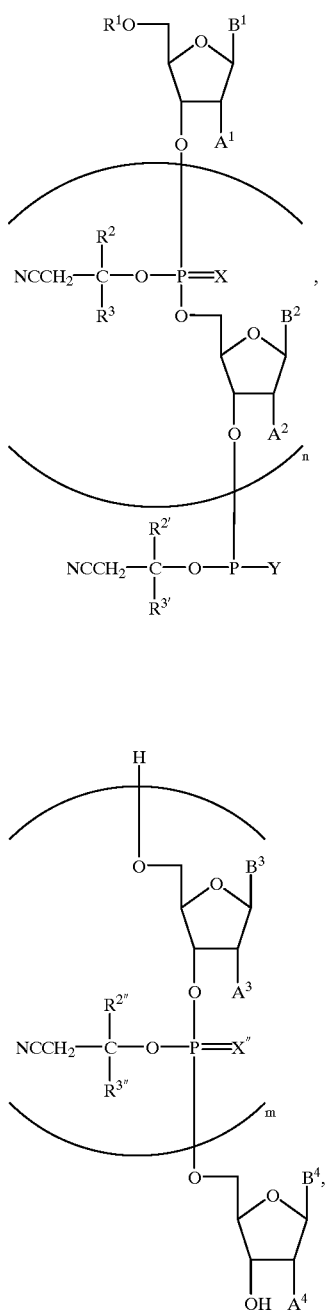

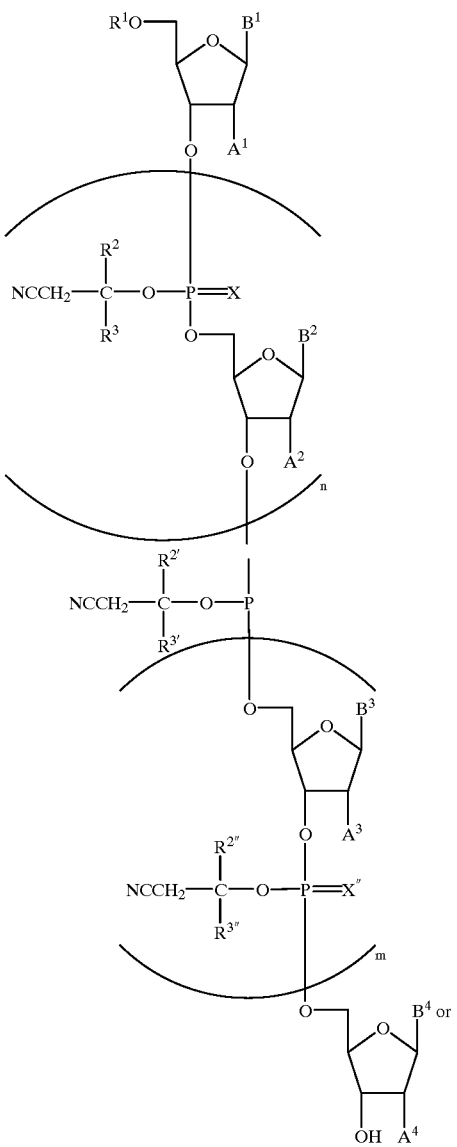

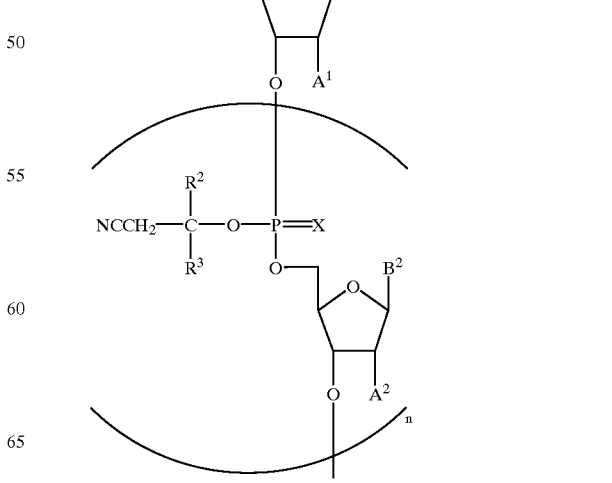

-continued

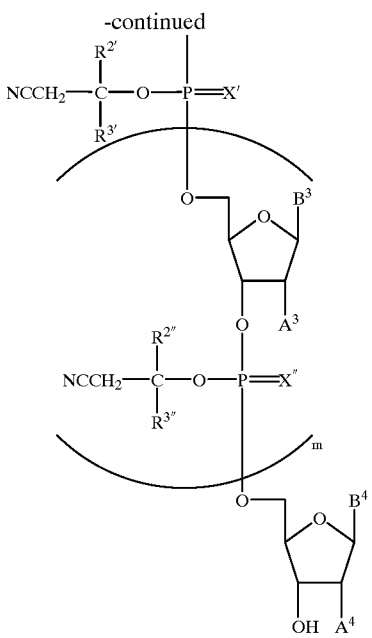

wherein the above formulas (I-4), (II), (III) and (IV), $R^1$ represents a protective group or an organic group represented by the formula —C(=O)—A'—(OCH$_2$CH$_2$)$_k$OCH$_3$ in which k represents an integer of 3 or more, and A' represents a divalent organic group; $R^2$, $R^{2'}$, $R^{2''}$, $R^3$, $R^{3'}$ and $R^{3''}$ each represents a hydrogen atom or an alkyl, cycloalkyl, aryl or aralkyl group which may contain a hetero-atom and $R^2$, $R^{2'}$, $R^{2''}$, $R^3$, $R^{3'}$ and $R^{3''}$ may be the same or different; $B^1$, $B^2$, $B^3$ and $B^4$ each represents a base, optionally, protected by a protective group common in nucleotide chemistry or B' which represents —B$^{1'}$—C(=O)—A—(OCH$_2$CH$_2$)$_k$OCH$_3$ in which $B^{1'}$ represents one of the groups represented by the formula (1):

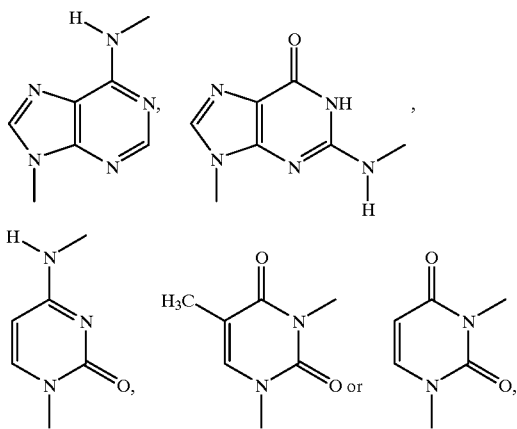

k represents an integer of 3 or more, A is a divalent group and represents an arylene group or an alkylene group having a straight or branched chain which may contain a hetero-atom; X, $X^1$ and X" each represents an oxygen atom or a sulfur atom; Y represents an azolyl group; $A^1$, $A^2$, $A^3$ and $A^4$ each represents a hydrogen atom, a hydroxyl group, an alkoxy group or a trialkylsilyloxy group; and m and n each represents 0 or an integer of 1 to 100; excluding the case wherein at least one of the combinations of $R^2$ and $R^3$, of $R^{2'}$ and $R^{3'}$ and of $R^{2''}$ and $R^{3''}$ being a hydrogen atom and a hydrogen atom, a hydrogen atom and a methyl group, a hydrogen atom and an ethyl group, a methyl group and a methyl group, a methyl group and an ethyl group or a ethyl group and ethyl group.

11. A method for producing a nucleotide block or an oligonucleotide according to claim 10, wherein the sum of van der Waals volumes of $R^2$ and $R^3$, the sum of van der Waals volumes of $R^{2'}$ and $R^{3'}$, and the sum of van der Waals volumes of $R^{2''}$ and $R^{3''}$ in the nucleoside derivative or nucleotide derivative are respectively at least 49 cubic angstroms, and X is an imidazolyl group, 2-methylimidazolyl group, 4-methylimidazolyl group or triazolyl group.

12. A nucleotide derivative represented by the formula (III) according to claim 10.

13. A nucleotide block or oligonucleotide represented by the formula (IV) according to claim 10.

14. A nucleotide derivative represented by the formula (III) according to claim 11.

15. A nucleotide block or oligonucleotide represented by the formula (IV) according to claim 11.

16. A nucleotide compound according to claim 1, wherein said nucleotide excludes the combination of $R^2$ and $R^3$ representing a hydrogen atom and a hydrogen atom, a hydrogen atom and a methyl group, a hydrogen atom and an ethyl group, a methyl group and a methyl group, a methyl group and an ethyl group or an ethyl group and an ethyl group.

17. A method according to claim 10, wherein formula (III) excludes the combination of $R^2$ and $R^3$ from representing a hydrogen atom and a hydrogen atom, a hydrogen atom and a methyl group, a hydrogen atom and an ethyl group, a methyl group and a methyl group, a methyl group and an ethyl group or an ethyl group and an ethyl group.

18. A nucleotide compound according to claim 1, wherein the nucleotide excludes the combination of $R^{2'}$ and $R^{3'}$ from representing a hydrogen atom and a hydrogen atom, a hydrogen atom and a methyl group, a hydrogen atom and an ethyl group, a methyl group and a methyl group, a methyl group and an ethyl group or an ethyl group and an ethyl group.

19. A method according to claim 10, wherein formula (III) excludes the combination of $R^{2'}$ and $R^{3'}$ from representing a hydrogen atom and a hydrogen atom, a hydrogen atom and a methyl group, a hydrogen atom and an ethyl group, a methyl group and a methyl group, a methyl group and an ethyl group or an ethyl group and an ethyl group.

20. A method according to claim 10, wherein formula (III) excludes the combination of $R^{2''}$ and $R^{3''}$ from representing a hydrogen atom and a hydrogen atom, a hydrogen atom and a methyl group, a hydrogen atom and an ethyl group, a methyl group and a methyl group, a methyl group and an ethyl group or an ethyl group and an ethyl group.

21. A nucleotide according to claim 1, wherein said nucleotide $R^{2'}$ and $R^{3'}$ are selected from the group consisting of a hydrogen atom, a methyl group, an ethyl group, an n-propyl group, an isopropyl group, an isobutyl group, a sec-butyl group, a tert-butyl group, an n-pentyl group, a 1-methylbutyl group, a 1-ethylpropyl group, a cyclohexyl group, a n-nonyl group, 2-phenyletayl group, a 2-(methylthio)ethyl group, a phenyl group, a 1,1-diethyl-3-butenyl group and 1,1-dimethyl-2-phenylethyl group, provided that the combination of $R^{2'}$ and $R^{3'}$ does not represent a hydrogen atom and hydrogen atom, a hydrogen atom and a methyl group, a hydrogen atom and an ethyl group, a methyl group and a methyl group, a methyl group and an ethyl group or an ethyl group and an ethyl group.

* * * * *